US011512312B2

(12) United States Patent
Mootha et al.

(10) Patent No.: US 11,512,312 B2
(45) Date of Patent: Nov. 29, 2022

(54) TREATMENT OF FUCHS' ENDOTHELIAL CORNEAL DYSTROPHY

(71) Applicant: The Board of Regents of the University of Texas System, Austin, TX (US)

(72) Inventors: Venkateswara V. Mootha, Coppell, TX (US); David R. Corey, Dallas, TX (US); Jiaxin Hu, Coppell, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/492,522

(22) PCT Filed: Mar. 9, 2018

(86) PCT No.: PCT/US2018/021729
§ 371 (c)(1),
(2) Date: Sep. 9, 2019

(87) PCT Pub. No.: WO2018/165541
PCT Pub. Date: Sep. 13, 2018

(65) Prior Publication Data
US 2021/0139894 A1 May 13, 2021

Related U.S. Application Data

(60) Provisional application No. 62/560,472, filed on Sep. 19, 2017, provisional application No. 62/469,952, filed on Mar. 10, 2017.

(51) Int. Cl.
| | | |
|---|---|---|
| *C07H 21/04* | (2006.01) | |
| *C12N 15/113* | (2010.01) | |
| *A61K 9/00* | (2006.01) | |
| *A61K 31/7105* | (2006.01) | |
| *C12N 15/11* | (2006.01) | |

(52) U.S. Cl.
CPC .......... *C12N 15/113* (2013.01); *A61K 9/0048* (2013.01); *A61K 31/7105* (2013.01); *C12N 15/11* (2013.01); *C12N 2310/11* (2013.01); *C12N 2310/20* (2017.05); *C12N 2310/315* (2013.01); *C12N 2310/321* (2013.01); *C12N 2310/3231* (2013.01); *C12N 2310/3515* (2013.01)

(58) Field of Classification Search
None
See application file for complete search history.

(56) References Cited

U.S. PATENT DOCUMENTS

| 2013/0225659 A1 | 8/2013 | Bennett |
| 2015/0291958 A1 | 10/2015 | Albaek et al. |
| 2016/0317528 A1 | 11/2016 | Koizumi et al. |

FOREIGN PATENT DOCUMENTS

| WO | WO 2011/097388 | 8/2011 |
| WO | WO 2016/060919 | 4/2016 |
| WO | WO 2017/004616 | 1/2017 |
| WO | WO 2017/060317 | 4/2017 |
| WO | WO 2017/185054 | 10/2017 |

OTHER PUBLICATIONS

Soragni, Elisabetta, et al. "RNA toxicity in corneal endothelial tissue in Fuchs dystrophy." Investigative Ophthalmology & Visual Science 56.7 (2015): 1171-1171).*
Batra et al., "Elimination of Toxic Microsatellite Repeat Expansion RNA by RNA-Targeting Cas9," *Cell*, 170(5): 899-912, 2017.
Brook et al., "Molecular basis of myotonic dystrophy: expansion of a trinucleotide (CTG) repeat at the 3' end of a transcript encoding a protein kinase family member," *Cell*, 68(4):799-808, 1992.
Du et al., "RNA toxicity and missplicing in the common eye disease Fuchs endothelial corneal dystrophy," *Journal of Biological Chemistry*, 290(10):5979-5990, 2015.
Extended European Search Report issued in European Application No. 18764253.3, dated Dec. 11, 2020.
Hu et al., "Allele-selective inhibition of huntingtin expression by switching to an miRNA-like RNAi mechanism," *Chem. Biol.*, 17:1183-1188, 2010.
Hu et al., "Allele-selective inhibition of mutant atrophin-1 expression by duplex and single-stranded RNAs," *Biochemistry*, 53:4510-4518, 2014.
Hu et al., "Allele-specific silencing of mutant huntingtin and ataxin-3 genes by targeting expanded CAG repeats in mRNAs," *Nat. Biotechnol.*, 27(5):478-484, 2009.
Hu et al., "Exploring the effect of sequence length and composition on allele-selective inhibition of human huntingtin expression by single-stranded silencing RNAs," *Nucleic Acid Therapeutics*, 24:199-209, 2014.
Hu et al., "Oligonucleotides targeting TCF4 triplet repeat expansion inhibit RNA roci and mis-splicing in Fuchs' dystrophy," *Human Molecular Genetics*, 27(6):1015-1026, 2018.
Liu et al., "c9orf72 Disease-Related Foci Are Each Composed of One Mutant Expanded Repeat RNA," *Cell Chem Biol.*, 24(2):141-148, 2017.
Luther et al., "TGC repeats in intron 2 of the TCF4 gene have a good predictive power regarding to Fuchs endothelial corneal dystrophy," *Klin Monbl Augenheilkd*, 233(2):187-194, 2016.
Mahadevan et al., "Myotonic dystrophy mutation: an unstable CTG repeat in the 3' untranslated region of the gene," *Science*, 255: 1253-1255, 1992.
Mootha et al., "Association and familial segregation of CTG 18.1 trinucleotide repeat expansion of TCF4 gene in Fuchs' endothelial corneal dystrophy," *Investigative Ophthalmology & Visual Science*, 55:33-42, 2014.
Mootha et al., "Fuchs' Endothelial Corneal Dystrophy and RNA Foci in Patients With Myotonic Dystrophy," *Investigative ophthalmology & visual science*, 58, 4579-4585, 2017.

(Continued)

*Primary Examiner* — Kimberly Chong
(74) *Attorney, Agent, or Firm* — ParkerHighlander PLLC

(57) ABSTRACT

Described are compounds and methods useful in the treatment of Fuchs' Endothelial Corneal Dystrophy (FECD).

22 Claims, 19 Drawing Sheets
Specification includes a Sequence Listing.

(56) References Cited

OTHER PUBLICATIONS

Mootha et al., "TCF4 triplet repeat expansion and nuclear RNA foci in Fuchs' endothelial corneal dystrophy," *Invest Ophthalmol Vis Sci*, 56(3):2003-2011, 2015.

Mootha et al., "TCF4 triplet repeat expansion in Fuchs' endothelial corneal dystrophy: an ideal oligonucleotide therapeutic target for a common human disease," RNA & Oligonucleotide Therapeutics Meeting, Cold Spring Harbor, Abstract, Mar. 2017.

Mootha et al., "TCF4 triplet repeat expansion in Fuchs' endothelial corneal dystrophy: an ideal oligonucleotide therapeutic target for a common human disease," RNA & Oligonucleotide Therapeutics Meeting, Cold Spring Harbor, Presentation, Mar. 2017.

Nelles et al., "Programmable RNA Tracking in Live Cells with CRISPR/Cas9," *Cell*, 165(2):P488-496, 2016.

PCT International Preliminary Report on Patentability issued in International Application No. PCT/US2018/021729, dated Sep. 19, 2019.

PCT International Search Report and Written Opinion issued in International Application No. PCT/US2018/021729, dated Jul. 19, 2018.

Pendergraff et al., "Locked nucleic acid gapmers and conjugates potently silence ADAM33, an asthma-associated metalloprotease with nuclear-localized mRNA," *Molecular Therapy: Nucleic Acids*, 8:158-168, 2017.

Sobczak et al., "RNA interference targeting CUG repeats in a mouse model of myotonic dystrophy," *Molecular Therapy*, 21(2):380-387, 2013.

Van Agtmaal et al., "CRISPR/Cas9-Induced (CTG-CAG) n Repeat Instability in the Myotonic Dystrophy Type 1 Locus: Implications for Therapeutic Genome Editing," Molecular therapy: the journal of the American Society of Gene Therapy, 25:24-43, 2017.

Wieben et al., "A common trinucleotide repeat expansion within the transcription factor 4 (TCF4, E2-2) gene predicts Fuchs corneal dystrophy," *PloS One*, 7:e49083, 2012.

Wojtkowiak-Szlachcic et al., "Short antisense-locked nucleic acids (all-LNAs) correct alternative splicing abnormalities in myotonic dystrophy," *Nucleic Acids Research*, 43(6):3318-3331, 2015.

Xing et al., "Transethnic replication of association of CTG18.1 repeat expansion of TCF4 gene with Fuchs' corneal dystrophy in Chinese implies common causal variant," *Investigative Ophthalmology & Visual Science*, 55(11):7073-7078, 2014.

\* cited by examiner

| ID | Age | Sex | Ethnicity | CTG Repeat | % of Total Cells with Sense Foci | Number of Sense Foci per 100 Cells | % of Total Cells with Antisense Foci | Number of Antisense Foci per 100 Cells |
|---|---|---|---|---|---|---|---|---|
| Control | | | | | | | | |
| 2014.1670 | 45 | M | Black | 23,35 | 0.0 | 0.0 | 0.0 | 0.0 |
| CA052 | 75 | F | White | 12,17 | 0.0 | 0.0 | 0.0 | 0.0 |
| FECD | | | | | | | | |
| CA056 | 59 | F | White | 24,150 | 92.0 | 211 | 6.0 | 7.2 |
| VVM573 | 50 | F | White | 12,130 | 91.2 | 217 | 7.7 | 9.0 |
| VVM672 | 55 | F | White | 20,130 | 93.0 | 171 | 2.8 | 5.0 |
| CA105 | 58 | M | White | 12,130 | 82.8 | 195 | 7.1 | 8.0 |
| CA120 | 58 | F | White | 16,130 | 84.9 | 168 | 5.8 | 7.0 |
| AK009 | 61 | M | White | 18,130 | 79.7 | 171 | 8.3 | 13.0 |
| CA033 | 62 | M | White | 71,130 | 95.0 | 277 | 10.0 | 12.0 |
| CA063 | 64 | F | White | 12,74 | 92.3 | 210 | 6.2 | 7.0 |
| CA045 | 66 | F | White | 15,120 | 91.7 | 210 | 8.0 | 9.0 |
| CA026 | 67 | M | White | 12,67 | 85.0 | 160 | 5.0 | 6.0 |
| CA047 | 67 | M | White | 12,91 | 69.0 | 129 | 41.0 | 62.0 |
| CA054 | 68 | M | White | 12,79 | 90.0 | 272 | 6.0 | 6.7 |
| VVM513 | 70 | M | White | 12,88 | 93.7 | 212 | 6.1 | 7.0 |
| CA062 | 71 | F | White | 17,87 | 89.0 | 173 | 17.0 | 20.0 |
| CA027 | 71 | F | White | 12,74 | 86.3 | 143 | 27.0 | 13.0 |
| CA050 | 73 | F | White | 17,74 | 90.0 | 191 | 13.0 | 16.0 |
| CA048 | 74 | F | White | 12,54 | 62.0 | 127 | 12.6 | 20.0 |
| CA049 | 75 | F | White | 17,1000 | 81.0 | 144 | 15.0 | 17.0 |
| CA053 | 78 | F | White | 14,84 | 70.0 | 134 | 4.0 | 4.0 |
| VVM289 | 86 | F | White | 12,87 | 61.9 | 96 | 3.8 | 4.0 |

FIG. 2A

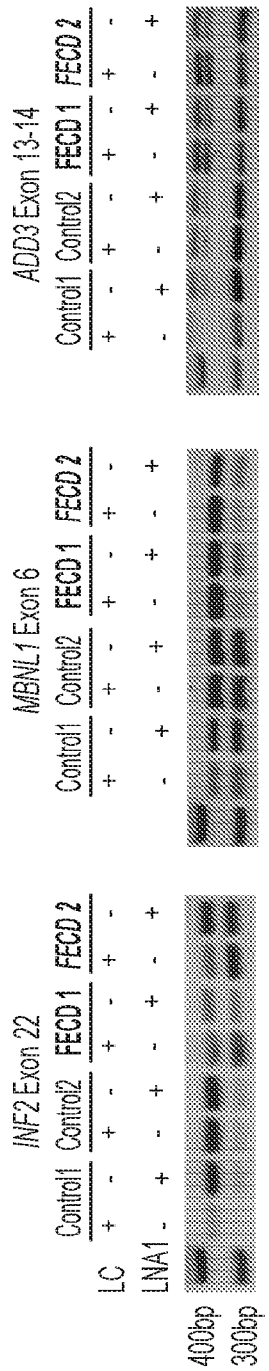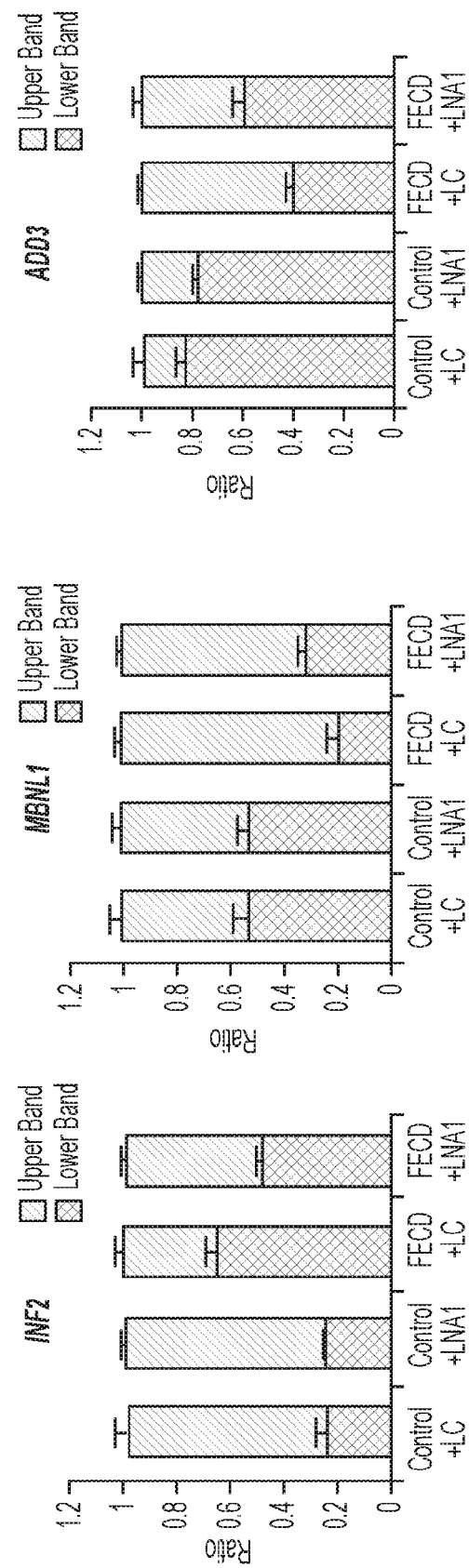
FIG. 4D
FIG. 4E

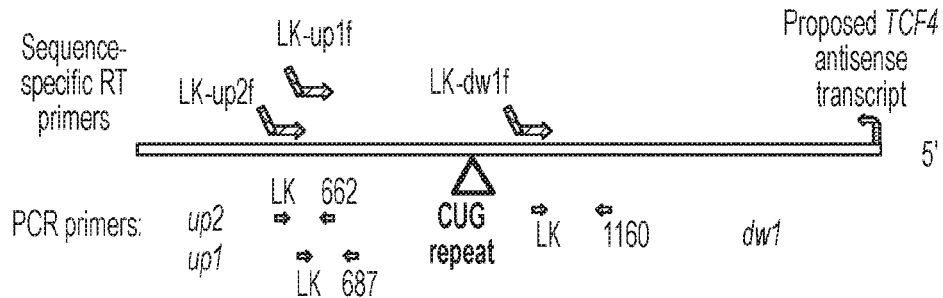

FIG. 5A

| Name | Sequence (5'-3') | |
|---|---|---|
| LK | CGACTGGAGCACGAGGACACTGA | (SEQ ID NO: 30) |
| LK-up1 | CGACTGGAGCACGAGGACACTGATG TGGAGTTTTACGGCTGTA | (SEQ ID NO: 31) |
| LK-up2 | CGACTGGAGCACGAGGACACTGAGT AGTCGTAGGATCAGCACAAAG | (SEQ ID NO: 32) |
| LK-dw1 | CGACTGGAGCACGAGGACACTGACA CTTTCTCCATTCGTTCCTTTG | (SEQ ID NO: 33) |
| up1 | R: ATGTCTGGGACTTGGTTTAGG | (SEQ ID NO: 34) |
| up2 | R: GGAAGCAAAGGGATGGAGAA | (SEQ ID NO: 35) |
| dw1 | R: TCTCTCTTTCACTCCCTCTCTC | (SEQ ID NO: 36) |

FIG. 5B

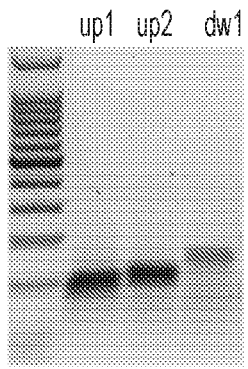

FIG. 5C

```
              1,610      1,620      1,630      1,640      1,650      1,660      1,670      1,680
TCF4 intron 2 CACACTTGTGGAGTTTACGGCTGTACTTGGTCCTTCTCCATCCCTTGCTTCCTTTCCTAAACCAAGTCCAGACATGT (SEQ ID NO: 37)
AS up2        CTTGTGGAGTTTACGGCTGTACTTGGTCCTTCTCCATCCCTTGCTT                             (SEQ ID NO: 38)
AS up1                                     TTGCTTCCTTTCCTAAACCAAGTCCCAGAC              (SEQ ID NO: 39)

1,070      1,080      1,090      1,100      1,110      1,120      1,130      1,140      1,150      1,160
TCF4 intron 2 GGAAGGTGTGCATTATCCACTAGATACCTCGAAGAAGAGGGAAACCAATTAGGTCGAAATAAATGCTGAAAGAGGAGTGAAAGAGAGTGA (SEQ ID NO: 40)
AS dw1        GGTGTCCATTATCCACTAGATACGTCGAAGAAGAGGGAAACCAATTAGGTCGAAATAAATGCTGGAGAGAGGGAGTGAAAGAGAGAGA   (SEQ ID NO: 41)

FIG. 5D
```

| Donor | Age | CTG Repeat |
|---|---|---|
| FECD Tissue 1 | 54 | 17, 110 |
| FECD Tissue 2 | 51 | 13, 130 |
| Control Tissue 1 | 55 | 13, 13 |
| Control Tissue 2 | 64 | 13, 19 |
FIG. 11A
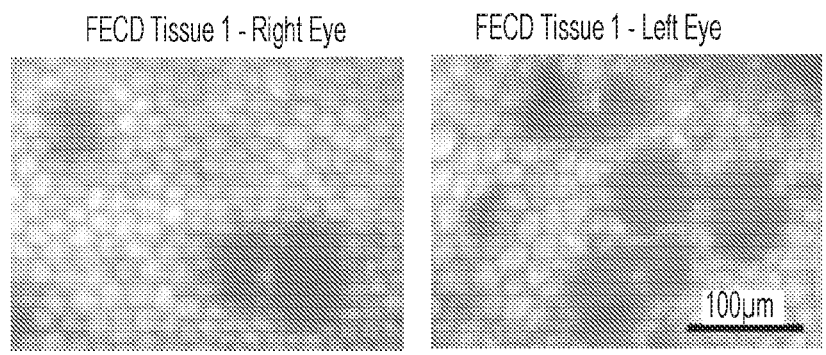
FIG. 11B
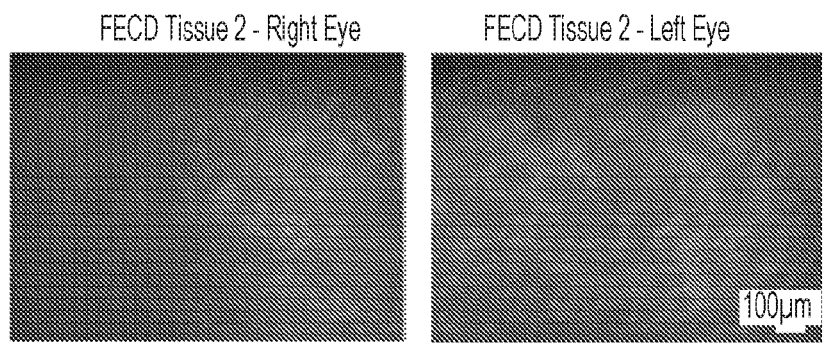
FIG. 11C

| siRNA | Sequence (AS/S) | SEQ ID NO: | Tm, °C | Target | Mismatch |
|---|---|---|---|---|---|
| CAG | CAGCAGCAGCAGCAGCAGCdTdT<br>dTdTCUCGUCGUCGUCGUCGUCG | 1<br>3 | 84.8 | CUG repeat | 0 |
| AGC | AGCAGCAGCAGCAGCAGCAdTdT<br>dTdTACGUCGUCGUCGUCGUCGU | 2<br>42 | >87 | CUG repeat | 0 |
| GCA | AGCAGCAGCAGCAGCAGCAdTdT<br>dTdTUCGUCGUCGUCGUCGUCGU | 2<br>4 | >87 | CUG repeat | 0 |
| CAG-P10 | CAGCAGCAGUAGCAGCAGCdTdT<br>dTdTCUCGUCGUCAUCGUCGUCG | 43<br>44 | 85.0 | CUG repeat | P10 |
| CAG-P1011 | AGCAGCAGUUGCAGCAGCdTdT<br>dTdTCUCGUCGUCAUCGUCGUC | 45<br>46 | 77.2 | CUG repeat | P10, 11 |
| CAG-P10mo | CAGCAGCAGUAGCAGCAGCdTdT<br>dTdTcUcGUcGUcAUcGUcGUcG | 47<br>48 | 84.6 | CUG repeat | P10 |
| CAG-P1011mo | AGCAGCAGUUGCAGCAGCdTdT<br>dTdTcUcGUcGUcAUcGUcGUcG | 49<br>50 | 79.0 | CUG repeat | P10, 11 |

FIG. 12A

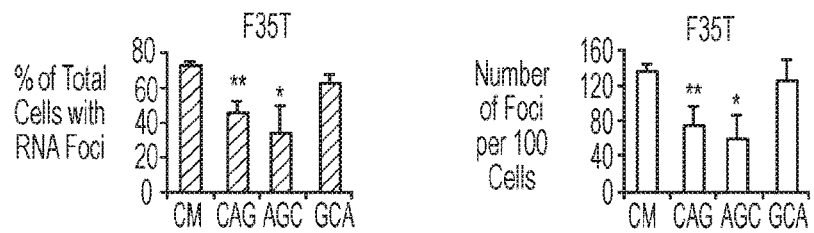

FIG. 12B

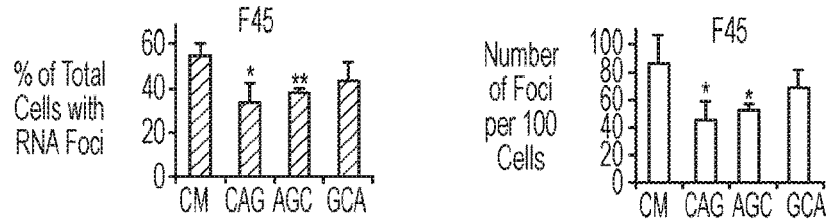

FIG. 12C

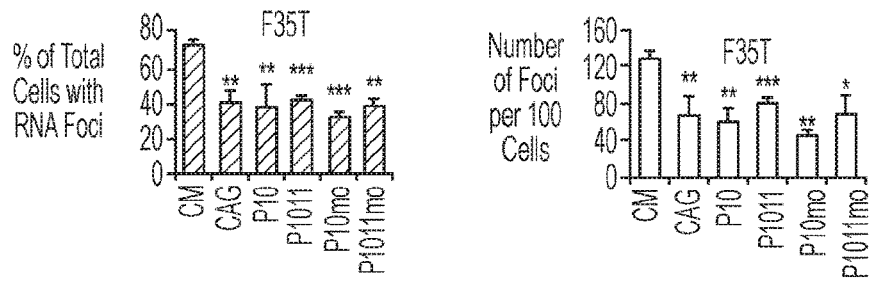

FIG. 12D

| Name | Sequence 5'-3' (SEQ ID NO:) | Target | Intron2 position | Mass observed/Calculated |
|---|---|---|---|---|
| Gap A | TGGAAGGCGGTTTGGA (51) | Intron2, upstream | 785-800 | 5425.55/5425.31 |
| Gap B | CCTGCCTAGGGCTACG (52) | Intron2, downstream | 978-993 | 5308.33/5308.31 |
| Gap C | CCCACTTGGAAGGCGG (53) | Intron2, upstream | 791-806 | 5371.50/5371.34 |
| Gap D | GGGAATTGAAGGCCAG (54) | Intron2, upstream | 216-231 | 5417.49/5417.33 |
| Gap E | TCAGACATGGCCAAGT (55) | Intron2, upstream | 315-330 | 5312.32/5312.28 |
| Gap F | CTGACATGTCTGGGAC (56) | Intron2, upstream | 677-692 | 5333.48/5333.29 |
| Gap G | GGACCAAGTACAGCCG (57) | Intron2, upstream | 627-642 | 5336.52/5336.31 |
| Gap rep | AGCAGCAGCAGCAGCA (58) | CUG repeat | | 6241.50/6241.04 |

FIG. 13A

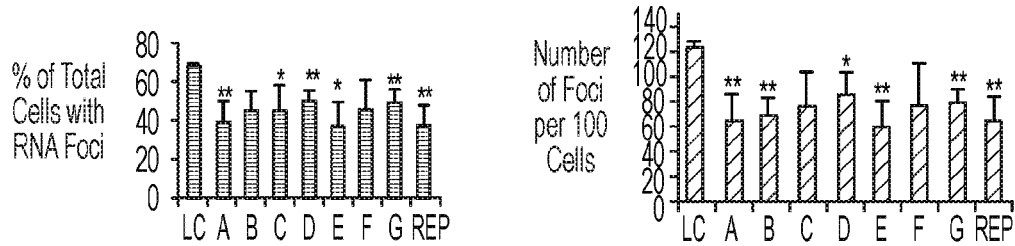

FIG. 13B

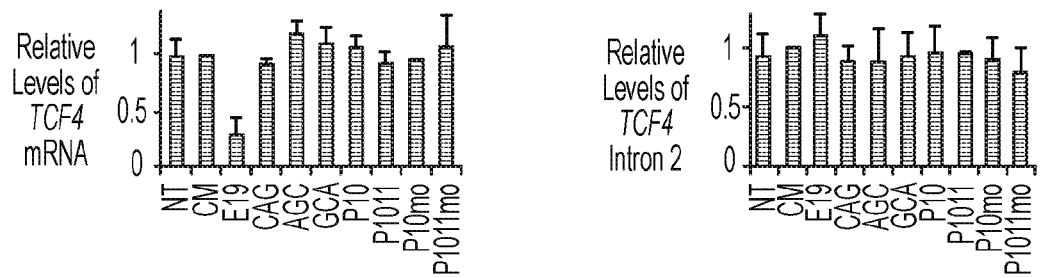

FIG. 14A

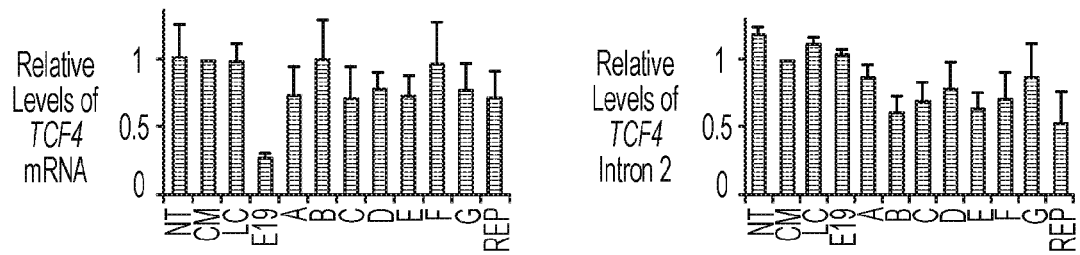

FIG. 14B

| LNA | Sequence 5'-3' | amount (nmol) | Mass observed/Calc | Target Position on Malat1 RNA | SEQ ID NO: |
|---|---|---|---|---|---|
| 220 | AAAATGGCGCTGCGCT | 62 | 5328.52/5328.28 | 68-83 | SEQ ID NO: 131 |
| 221 | TAAAATGGCGCTGCGC | 20 | 5343.57/5342.30 | 69-84 | SEQ ID NO: 132 |
| 222 | ATGGCGCTGCGCTTAA | 78 | 5305.56/5305.25 | 65-80 | SEQ ID NO: 133 |
| 223 | GGCGCTGCGCTTAAGA | 55 | 5344.5/5344.28 | 63-78 | SEQ ID NO: 134 |
| 224 | AGCTGCACTGTGCTGT | 58 | 5310.48/5310.26 | 3983-3998 | SEQ ID NO: 135 |
| 225 | AAGCTGCACTGTGCTG | 81 | 5319.49/5319.27 | 3984-3999 | SEQ ID NO: 136 |
| 226 | ATACTGCCAGGCTGGT | 82 | 5305.48/5305.25 | 4931-4946 | SEQ ID NO: 137 |
| 227 | CGTTAGCGCTCCTTCC | 83 | 5286.42/5386.24 | 2836-2851 | SEQ ID NO: 138 |
| 228 | AGGCTGGTTATGACTC | 107 | 5348.51/5348.30 | 4923-4938, m3341 | SEQ ID NO: 139 |
| 229 | CAGGCTGGTTATGACT | 106 | 5348.51/5348.30 | 4924-4939, m3342 | SEQ ID NO: 140 |
| LC | GCTATACCAGCGTCGTCAT | | | Non-complimentary control LNA | SEQ ID NO: 141 |

FIG.18A

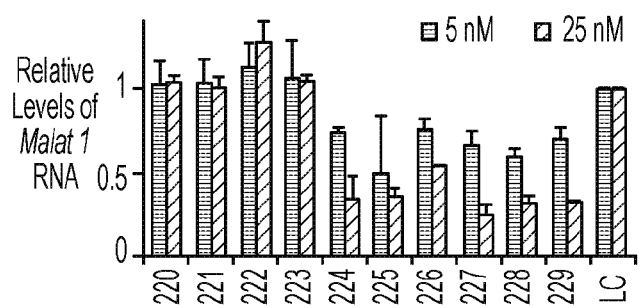

FIG.18B

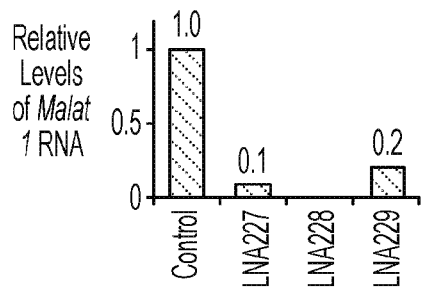

FIG.18C

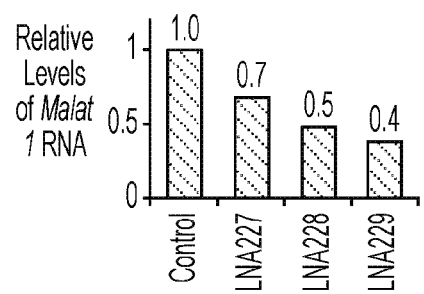

FIG.18D

SEQUENCE LISTING

<160> NUMBER OF SEQ ID NOS: 141

<210> SEQ ID NO 1

```
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
cagcagcagc agcagcagct t                                               21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
agcagcagca gcagcagcat t                                               21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
ttcucgucgu cgucgucguc g                                               21

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
ttucgucguc gucgucgucg u                                               21

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
tgacgatgag gacctgacac                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
gtctggggct tgtcactctt                                                 20

<210> SEQ ID NO 7
<211> LENGTH: 22
<212> TYPE: DNA
<213> ORGANISM: Artificial sequence
<220> FEATURE:
<223> OTHER INFORMATION: Synthetic primer

<400> SEQUENCE: 7
```
gagagaggga gtgaaagaga ga                                        22

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
ggcaatgtcc atttccatct                                           20

<210> SEQ ID NO 9
<211> LENGTH: 40
<212> TYPE: DNA
<213> ORGANISM: Artificial sequence
<220> FEATURE:
<223> OTHER INFORMATION: Synthetic primer

<400> SEQUENCE: 9
atttaggtga cactatagaa ctctgctcct cctgttcgac                     40

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
ttgattttgg agggatctcg                                           20

<210> SEQ ID NO 11
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 11
atttaggtga cactatagaa tgctaaaatg catcaccaac a                   41

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
gagccagtaa aatgtccact tg                                        22

<210> SEQ ID NO 13
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 13
atttaggtga cactatagaa tgttgcactt tctccattcg                     40

<210> SEQ ID NO 14
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 14
caggagagca atttgaagca                                               20

<210> SEQ ID NO 15
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 15
atttaggtga cactatagaa tgacgatgag gacctgacac                          40

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
aggatcagga gcttggtctg                                               20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tagggacgga caaagagctg                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ccacttgcca aagaagttgg                                               20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ttcacctcct gtgagcagtg                                               20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ttctccattc gttcctttgc                                               20
```

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
cactccctct ctctccagca                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gctctgactc agggaaggtg                                               20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
acgatgagga cctgacacca                                               20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gggcttgtca ctcttgaggt                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
agaaggcaga gcgtgagaag                                               20

<210> SEQ ID NO 26
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 26
cagcagcagc agcagcagc                                                19

<210> SEQ ID NO 27
<211> LENGTH: 19
<212> TYPE: DNA
<213> ORGANISM: Artificial sequence
<220> FEATURE:

<223> OTHER INFORMATION: Synthetic oligonucleotide

<400> SEQUENCE: 27
agcagcagca gcagcagca                                                19

<210> SEQ ID NO 28
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 28
gcagcagcag cagcagcag                                                19

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
agcagcagca gcagca                                                   16

<210> SEQ ID NO 30
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 30
cgactggagc acgaggacac tga                                           23

<210> SEQ ID NO 31
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 31
cgactggagc acgaggacac tgatgtggag ttttacggct gta                     43

<210> SEQ ID NO 32
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 32
cgactggagc acgaggacac tgagtagtcg taggatcagc acaaag                  46

<210> SEQ ID NO 33
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 33
cgactggagc acgaggacac tgacactttc tccattcgtt cctttg                  46

```
<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 34
atgtctggga cttggtttag g                                           21

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
ggaagcaaag ggatggagaa                                             20

<210> SEQ ID NO 36
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 36
tctctctttc actccctctc tc                                          22

<210> SEQ ID NO 37
<211> LENGTH: 80
<212> TYPE: DNA
<213> ORGANISM: Artificial sequence
<220> FEATURE:
<223> OTHER INFORMATION: Synthetic oligonucleotide

<400> SEQUENCE: 37
cacacttgtg gagttttacg gctgtacttg gtccttctcc atcccttTgc ttccttttcc   60
taaaccaagt cccagacatg                                             80

<210> SEQ ID NO 38
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 38
cttgtggagt tttacggctg tacttggtcc ttctccatcc ctttgctt               48

<210> SEQ ID NO 39
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 39
ttgcttcctt ttcctaaacc aagtcccaga c                                31

<210> SEQ ID NO 40
<211> LENGTH: 97
<212> TYPE: DNA
<213> ORGANISM: Artificial sequence
<220> FEATURE:
```

<223> OTHER INFORMATION: Synthetic oligonucleotide

<400> SEQUENCE: 40
ggaaggtgtg cattatccac tagatacgtc gaagaagagg gaaaccaatt agggtcgaaa    60
taaatgctgg agagagaggg agtgaaagag agagtga                             97

<210> SEQ ID NO 41
<211> LENGTH: 89
<212> TYPE: DNA
<213> ORGANISM: Artificial sequence
<220> FEATURE:
<223> OTHER INFORMATION: Synthetic oligonucleotide

<400> SEQUENCE: 41
ggtgtgcatt atccactaga tacgtcgaag aagagggaaa ccaattaggg tcgaaataaa    60
tgctggagag agagggagtg aaagagaga                                      89

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 42
ttacgucguc gucgucgucg u                                              21

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 43
cagcagcagu agcagcagct t                                              21

<210> SEQ ID NO 44
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 44
ttcucgucgu caucgucguc g                                              21

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
agcagcaguu gcagcagctt                                                20

<210> SEQ ID NO 46
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 46
ttcucgucgu caucgucguc g                    21

<210> SEQ ID NO 47
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 47
cagcagcagu agcagcagct t                    21

<210> SEQ ID NO 48
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 48
ttcucgucgu caucgucguc g                    21

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
agcagcaguu gcagcagctt                      20

<210> SEQ ID NO 50
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 50
ttcucgucgu caucgucguc g                    21

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
tggaaggcgg tttgga                          16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cctgcctagg gctacg                          16

<210> SEQ ID NO 53
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 53
cccacttgga aggcgg                                                    16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
gggaattgaa ggccag                                                    16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
tcagacatgg ccaagt                                                    16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ctgacatgtc tgggac                                                    16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
ggaccaagta cagccg                                                    16

<210> SEQ ID NO 58
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 58
agcagcagca gcagcagca                                                 19

<210> SEQ ID NO 59
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 59
agcagcagca gcagcagca                                                 19
```

```
<210> SEQ ID NO 60
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 60
ttagcagcag cagcagcagc a                                              21

<210> SEQ ID NO 61
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 61
ttagcagcag cagcagcagc att                                            23

<210> SEQ ID NO 62
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 62
agcagcagca gcagcagca                                                 19

<210> SEQ ID NO 63
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(2)
<223> OTHER INFORMATION: 2'-O-methylribonucleotide
<220> FEATURE:
<221> NAME/KEY: modified_base
<222> LOCATION: (18)..(19)
<223> OTHER INFORMATION: 2'-O-methylribonucleotide

<400> SEQUENCE: 63
ucgucgucgu cgucgucgu                                                 19

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (18)..(19)
<223> OTHER INFORMATION: 2'-O-methylribonucleotide

<400> SEQUENCE: 64
agcagcaguu gcagcagcuu                                                20

<210> SEQ ID NO 65
<211> LENGTH: 18
<212> TYPE: DNA
<213> ORGANISM: Artificial sequence
<220> FEATURE:
```

```
<223> OTHER INFORMATION: Synthetic oligonucleotide

<400> SEQUENCE: 65
ucgucgucaa cgucgucg                                                 18

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 2'-O-methylribonucleotide
<220> FEATURE:
<221> NAME/KEY: modified_base
<222> LOCATION: (2)..(2)
<223> OTHER INFORMATION: 2'-fluoro-2'-deoxyribonucleotide
<220> FEATURE:
<221> NAME/KEY: modified_base
<222> LOCATION: (3)..(20)
<223> OTHER INFORMATION: 2'-O-methylribonucleotide

<400> SEQUENCE: 66
agcagcaguu gcagcagcuu                                               20

<210> SEQ ID NO 67
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(15)
<223> OTHER INFORMATION: 2'-O-methylribonucleotide

<400> SEQUENCE: 67
ucgucgucaa cgucg                                                    15

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gcagcagcag cagcagcagc                                               20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gcagcagcag cagcagcagc                                               20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
```
cagcagcagc agcagcagca                                                    20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
ctgctgctgc tgctgctgct                                                    20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
tgctgctgct gctgctgctg                                                    20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gctgctgctg ctgctgctgc                                                    20

<210> SEQ ID NO 74
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 74
caccgagcag cagcagcagc agcag                                              25

<210> SEQ ID NO 75
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 75
aaacctgctg ctgctgctgc tgctc                                              25

<210> SEQ ID NO 76
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 76
caccggcagc agcagcagca gcagc                                              25

<210> SEQ ID NO 77
<211> LENGTH: 25
<212> TYPE: DNA

```
<213> ORGANISM: Artificial sequence
<220> FEATURE:
<223> OTHER INFORMATION: Synthetic oligonucleotide

<400> SEQUENCE: 77
aaacgctgct gctgctgctg ctgcc                                      25

<210> SEQ ID NO 78
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 78
caccgcagca gcagcagcag cagca                                      25

<210> SEQ ID NO 79
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 79
aaactgctgc tgctgctgct gctgc                                      25

<210> SEQ ID NO 80
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 80
gagggcctat ttcccatgat tcc                                        23

<210> SEQ ID NO 81
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 81
ctcttcttcg acgtatctag tgg                                        23

<210> SEQ ID NO 82
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 82
cactagatac gtcgaagaag agg                                        23

<210> SEQ ID NO 83
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 83
actagatacg tcgaagaaga ggg                                        23
```

<210> SEQ ID NO 84
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 84
ctgcctaggg ctacgtttcc tgg                                              23

<210> SEQ ID NO 85
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 85
gccccacttg gaaggcggtt tgg                                              23

<210> SEQ ID NO 86
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 86
ttgccaggaa acgtagccct agg                                              23

<210> SEQ ID NO 87
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 87
tccaaaccgc cttccaagtg ggg                                              23

<210> SEQ ID NO 88
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 88
aatccaaacc gccttccaag tgg                                              23

<210> SEQ ID NO 89
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 89
tggctttcgg aagttttgcc agg                                              23

<210> SEQ ID NO 90
<211> LENGTH: 23
<212> TYPE: DNA
<213> ORGANISM: Artificial sequence
<220> FEATURE:

<223> OTHER INFORMATION: Synthetic oligonucleotide

<400> SEQUENCE: 90
caggaaacgt agccctaggc agg                                    23

<210> SEQ ID NO 91
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 91
atccaaaccg ccttccaagt ggg                                    23

<210> SEQ ID NO 92
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 92
catcttacac caaactcatc tgg                                    23

<210> SEQ ID NO 93
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 93
atgaaagagc cccacttgga agg                                    23

<210> SEQ ID NO 94
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 94
cagcatgaaa gagccccact tgg                                    23

<210> SEQ ID NO 95
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 95
aaccaagtcc cagacatgtc agg                                    23

<210> SEQ ID NO 96
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 96
aattcatctc ctgacatgtc tgg                                    23

```
<210> SEQ ID NO 97
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 97
attcatctcc tgacatgtct ggg                                            23

<210> SEQ ID NO 98
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 98
tcctcttcta gaccttcttt tgg                                            23

<210> SEQ ID NO 99
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 99
gctgcaaagc tgcctgccta ggg                                            23

<210> SEQ ID NO 100
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 100
aaagagcccc acttggaagg cgg                                            23

<210> SEQ ID NO 101
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 101
ctcctgacat gtctgggact tgg                                            23

<210> SEQ ID NO 102
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 102
tccaaaagaa ggtctagaag agg                                            23

<210> SEQ ID NO 103
<211> LENGTH: 23
<212> TYPE: DNA
<213> ORGANISM: Artificial sequence
<220> FEATURE:
<223> OTHER INFORMATION: Synthetic oligonucleotide
```

<400> SEQUENCE: 103
acatgtctgg gacttggttt agg                                              23

<210> SEQ ID NO 104
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 104
tttttaatgc cagatgagtt tgg                                              23

<210> SEQ ID NO 105
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 105
ctgggacttg gtttaggaaa agg                                              23

<210> SEQ ID NO 106
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 106 cttttttgcag gctctgactc agg                                             23

<210> SEQ ID NO 107
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 107
tcagagcctg caaaaagcaa agg                                              23

<210> SEQ ID NO 108
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 108
tttttgcagg ctctgactca ggg                                              23

<210> SEQ ID NO 109
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 109
tgcaggctct gactcaggga agg                                              23

<210> SEQ ID NO 110
<211> LENGTH: 23

```
<212> TYPE: DNA
<213> ORGANISM: Artificial sequence
<220> FEATURE:
<223> OTHER INFORMATION: Synthetic oligonucleotide

<400> SEQUENCE: 110
aagtgcaaca agcagaaagg ggg                                              23

<210> SEQ ID NO 111
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 111
aaaagaaggt ctagaagagg agg                                              23

<210> SEQ ID NO 112
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 112
tagaccttct tttggagaaa tgg                                              23

<210> SEQ ID NO 113
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 113
ggctgcaaag ctgcctgcct agg                                              23

<210> SEQ ID NO 114
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 114
agaaagtgca acaagcagaa agg                                              23

<210> SEQ ID NO 115
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 115
ttcgttcctt tgcttttgc agg                                               23

<210> SEQ ID NO 116
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 116
```
aaagtgcaac aagcagaaag ggg                                              23

<210> SEQ ID NO 117
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 117
aaagccattt ctccaaaaga agg                                              23

<210> SEQ ID NO 118
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 118
gaaagtgcaa caagcagaaa ggg                                              23

<210> SEQ ID NO 119
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 119
gcaaaaagca aaggaacgaa tgg                                              23

<210> SEQ ID NO 120
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 120
tcttttggag aaatggcttt cgg                                              23

<210> SEQ ID NO 121
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 121
agaaggtcta gaagaggagg agg                                              23

<210> SEQ ID NO 122
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 122
gattttattt gtgtgttttg tgg                                              23

<210> SEQ ID NO 123
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 123
aggtctagaa gaggaggagg agg                                               23

<210> SEQ ID NO 124
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 124
tctagaagag gaggaggagg agg                                               23

<210> SEQ ID NO 125
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 125
agaggaggag gaggaggaga agg                                               23

<210> SEQ ID NO 126
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 126
ggaggaggag gaggagaagg agg                                               23

<210> SEQ ID NO 127
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 127
ggaggaggag gagaaggagg agg                                               23

<210> SEQ ID NO 128
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 128
ggaggaggag aaggaggagg agg                                               23

<210> SEQ ID NO 129
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 129
ggaggagaag gaggaggagg agg                                               23

```
<210> SEQ ID NO 130
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 130
ggagaaggag gaggaggagg agg                                              23

<210> SEQ ID NO 131
<211> LENGTH: 16
<212> TYPE: DNA
<213> ORGANISM: Artificial sequence
<220> FEATURE:
<223> OTHER INFORMATION: Synthetic oligo

<400> SEQUENCE: 131
aaaatggcgc tgcgct                                                      16

<210> SEQ ID NO 132
<211> LENGTH: 16
<212> TYPE: DNA
<213> ORGANISM: Artificial sequence
<220> FEATURE:
<223> OTHER INFORMATION: Synthetic oligo

<400> SEQUENCE: 132
taaaatggcg ctgcgc                                                      16

<210> SEQ ID NO 133
<211> LENGTH: 16
<212> TYPE: DNA
<213> ORGANISM: Artificial sequence
<220> FEATURE:
<223> OTHER INFORMATION: Synthetic oligo

<400> SEQUENCE: 133
atggcgctgc gcttaa                                                      16

<210> SEQ ID NO 134
<211> LENGTH: 16
<212> TYPE: DNA
<213> ORGANISM: Artificial sequence
<220> FEATURE:
<223> OTHER INFORMATION: Synthetic oligo

<400> SEQUENCE: 134
ggcgctgcgc ttaaga                                                      16

<210> SEQ ID NO 135
<211> LENGTH: 16
<212> TYPE: DNA
<213> ORGANISM: Artificial sequence
<220> FEATURE:
<223> OTHER INFORMATION: Synthetic oligo

<400> SEQUENCE: 135
agctgcactg tgctgt                                                      16

<210> SEQ ID NO 136
<211> LENGTH: 16
<212> TYPE: DNA
<213> ORGANISM: Artificial sequence
<220> FEATURE:
<223> OTHER INFORMATION: Synthetic oligo
```

```
<400> SEQUENCE: 136
aagctgcact gtgctg                                                       16

<210> SEQ ID NO 137
<211> LENGTH: 16
<212> TYPE: DNA
<213> ORGANISM: Artificial sequence
<220> FEATURE:
<223> OTHER INFORMATION: Synthetic oligo

<400> SEQUENCE: 137
atactgccag gctggt                                                       16

<210> SEQ ID NO 138
<211> LENGTH: 16
<212> TYPE: DNA
<213> ORGANISM: Artificial sequence
<220> FEATURE:
<223> OTHER INFORMATION: Synthetic oligo

<400> SEQUENCE: 138
cgttagcgct ccttcc                                                       16

<210> SEQ ID NO 139
<211> LENGTH: 16
<212> TYPE: DNA
<213> ORGANISM: Artificial sequence
<220> FEATURE:
<223> OTHER INFORMATION: Synthetic oligo

<400> SEQUENCE: 139
aggctggtta tgactc                                                       16

<210> SEQ ID NO 140
<211> LENGTH: 16
<212> TYPE: DNA
<213> ORGANISM: Artificial sequence
<220> FEATURE:
<223> OTHER INFORMATION: Synthetic oligo

<400> SEQUENCE: 140
caggctggtt atgact                                                       16

<210> SEQ ID NO 141
<211> LENGTH: 19
<212> TYPE: DNA
<213> ORGANISM: Artificial sequence
<220> FEATURE:
<223> OTHER INFORMATION: Synthetic oligo

<400> SEQUENCE: 141
gctataccag cgtcgtcat                                                    19
```

TREATMENT OF FUCHS' ENDOTHELIAL CORNEAL DYSTROPHY

PRIORITY CLAIM

The present application is a national phase application under 35 U.S.C. § 371 of International Application No. PCT/US2018/021729, filed Mar. 9, 2018, which claims benefit of priority to U.S. Provisional Application Ser. No. 62/560,472, filed Sep. 19, 2017, and U.S. Provisional Application Ser. No. 62/469,952, filed Mar. 10, 2017, the entire contents of each of which are hereby incorporated by reference in their entireties.

FEDERAL FUNDING SUPPORT CLAUSE

This invention was made with government support under grant numbers GM118103 and R01EY022161 awarded by the National Institutes of Health/National Eye Institute. The government has certain rights in the invention.

FIELD OF THE DISCLOSURE

The present disclosure relates to the fields of genetics, medicine and molecular biology. In particular, the disclosure relates to the targeting of nuclear foci in methods of treating Fuchs' Endothelial Corneal Dystrophy (FECD).

BACKGROUND

Fuchs' endothelial corneal dystrophy (FECD, MIM 136800) is an age-related degenerative disorder of the corneal endothelium. This genetic disease impacts one out of twenty whites in the United States over the age of forty (Lorenzetti et al., 1967). Over fourteen thousand corneal transplant procedures were performed in the U.S. for FECD in 2013 making it the leading indication for corneal transplantation (Eye Bank Statistical Report, 2013). The hallmark of FECD is premature senescence of the endothelium with diffuse thickening of the underlying basement membrane termed Descemet's membrane (Laing et al., 1981; Hogan et al., 1974; Chi et al., 1958). Focal excrescences of the Descemet's membrane visible by slit lamp biomicroscopy termed guttae are pathognomonic for the disorder when they reach confluence in the central cornea. In FECD, progressive loss of the endothelial cell density leads to corneal edema, scarring, and loss of vision.

Expanded trinucleotide repeats at the CTG18.1 locus in intron 2 of TCF4 are associated with FECD in a majority of whites with the disorder (Wieben et al., 2012; Mootha et al., 2014). One copy of the expanded CTG18.1 allele of greater than 40 CTG repeats confers more than a 30-fold increase in the risk for development of FECD in whites (Mootha et al., 2014). The triplet repeat expansion co-segregates with FECD in 52% (15/29) of white families with complete penetrance and an additional 10% (3/29) with incomplete penetrance (Mootha et al., 2014). Trans-ethnic studies including haplotype analysis and replication of the association with an odds ratio of 66.5 for each expanded CTG18.1 allele in a Singapore Chinese cohort with FECD helped provide additional human genetic evidence that the repeat expansion is a shared, common functional variant for FECD in Eurasian populations (Xing et al., 2014).

Expanded CUG repeat RNA ($CUG^{exp}$) accumulate as nuclear foci in the corneal endothelium of FECD subjects with the CTG18.1 triplet repeat expansion (Mootha et al., 2015; Du et al., 2015). RNA nuclear foci, a hallmark of toxic gain of function RNA, had been previously reported in rare, neurodegenerative disorders caused by simple repeat expansions. Rather than a primary mechanism of haploinsufficiency of TCF4 (Mootha et al., 2015), the triplet repeat expansion at the CTG18.1 locus may mediate endothelial dysfunction via aberrant gene splicing as a result of the mutant CUG RNA transcripts sequestering the splicing factor muscleblind-like 1 (Du et al., 2015). The CTG triplet repeat allele length is positively correlated with the Krachmer FECD grade of clinical severity (Soliman et al., 2015). Myotonic dystrophy type 1 patients with CTG expansions within the 3'-untranslated region of DMPK gene are also at increased risk for FECD and form $CUG^{exp}$-MBNL1 foci in corneal endothelium. (REF: Mootha, V. V., Hansen, B., Rong, Z., Mammen, P. P., Zhou, Z., Xing, C. and Gong, X. (2017) Fuchs' Endothelial Corneal Dystrophy and RNA Foci in Patients With Myotonic Dystrophy. *Investigative ophthalmology & visual science*, 58, 4579-4585.) Thus there are two distinct triplet repeats that converge on RNA foci and FECD, and it appearls likely that the foci are not bystanders but rather play a causal role for FECD.

SUMMARY

Thus, the present disclosure provides a method of reducing expanded CUG repeat RNA nuclear foci in a corneal endothelial cell comprising contacting a corneal endothelial cell having an expanded CUG repeat region with a oligonucleotide or oligonucleotide analog of 13 to 120 nucleotides in length and having a repeating tri-nucleobase sequence comprising CAG or targeting intronic CTG triplet repeat expansion in TCF4 or the 3' UTR of DMPK.

The oligonucleotide analog may comprise one or more chemically-modified nucleobases, such as a nuclease-resistant modification, such as a modified sugar moiety or a modified internucleoside linkage, such as a 4' to 2' bicyclic sugar moiety (such as a 4'-$CH_2$—O-2' or 4'-CH($CH_3$)—O-2' bicyclic sugar moiety), a tricyclic moiety, or a morpholino moiety (such as a phosphorodiamidate morpholino moiety) or a high-affinity sugar modification (such as a bicyclic sugar moiety or a 2'-modified sugar moiety).

A 4' to 2' bridge independently comprises from 2 to 4 linked groups independently selected from —[$C(R_a)(R_b)$]$_y$—, —$C(R_a)$=$C(R_b)$—, —$C(R_a)$=N—, —C(=$NR_a$)—, —C(=O)—, —C(=S)—, —O—, —Si($R_a$)$_2$—, —S(=O)$_x$—, and —N($R_1$)—; wherein x is 0, 1, or 2; y is 1, 2, 3, or 4; each $R_a$ and $R_b$ is, independently, H, a protecting group, hydroxyl, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_9$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_{20}$ aryl, substituted $C_5$-$C_9$ aryl, acyl (C(=O)—H), substituted acyl, a heterocycle radical, a substituted heterocycle radical, $C_1$-$C_6$ aminoalkyl, substituted $C_1$-$C_6$ aminoalkyl or a protecting group.

The 4' to 2' bridge may also independently comprise —[$C(R_c)(R_d)$]$_n$—, —[$C(R_c)(R_d)$]$_n$—O—, —$C(R_cR_d)$—N($R_e$)—O— or —$C(R_eR_d)$—O—N($R_e$)—, wherein each $R_c$ and $R_d$ is independently hydrogen, halogen, substituted or unsubstituted $C_1$-$C_6$ alkyl; and each $R_e$ is independently hydrogen or substituted or unsubstituted $C_1$-$C_6$ alkyl, such as wherein each 4' to 2' bridge is independently a 4'-(CH$_2$)$_2$-2',4'-(CH$_2$)$_3$-2',4'-CH$_2$—O-2',4'-CH(CH$_3$)—O-2', 4'-(CH$_2$)$_2$—O-2',4'-CH$_2$—O—N(R$_e$)-2' and 4'-CH$_2$—N(R$_e$)—O-2'-bridge.

The oligonucleotide or oligonucleotide analog may comprise terminal dT residues or 3' and/or 5' 2'-O-methyl modifications. The oligonucleotide or oligonucleotide analog may comprise a central mismatch (within bases 9-14) with a target sequence comprising said repeating tri-nucleobase sequence. The oligonucleotide or oligonucleotide analog may comprise a mismatch outside of the seed sequence (bases 2-8 within the guide strand complementary to the CUG target sequence). The oligonucleotide or oligonucleotide analog may comprise 4, 5, 6 or 7 repeats. The nucleosides may be linked by phosphate internucleoside linkages, such as wherein at least one of the phosphate internucleoside linkages is a phosphorothioate linkage. Each internucleoside linkage may be a phosphorothioate linkage. The oligonucleotide or oligonucleotide analog may comprise DNA nucleobases, RNA nucleobases or a mixture of DNA and RNA nucleobases. The oligonucleotide or oligonucleotide analog may a double-stranded RNA molecule, such as a siRNA or an shRNA. The siRNA may have strands of identical lengths, or different lengths. The siRNA may comprise one strand of 14-19 nucleotides in length and a second strand of 19-22 nucleotides in length. The siRNA may comprise at least one modified nucleotide, such as 2'-O-methyl-ribonucleotides, 2'-fluoro-ribonucleotides, 5'-vinylphosphonate, phosphorothioate linkage, or lipid conjugation. The siRNA may have every ribonucleotide modified, such as with 2'-O-methyl- and 2'-fluoro-ribonucleotides. The oligonucleotide or oligonucleotide analog may be a single-stranded DNA or RNA, such as an antisense molecule or a single-stranded RNA-like antisense molecule.

The cell may be contacted with said oligonucleotide or oligonucleotide analog at about 5-200 nM, or with about 1-5 µg of said oligonucleotide or oligonucleotide analog. The cell may be located in a subject suffering from Fuchs' endothelial corneal dystrophy. Contacting may comprise administering said oligonucleotide or oligonucleotide analog by direct administration into the eye. Contacting may also comprise administering said oligonucleotide or oligonucleotide analog more than once. The method may further comprise administering a second therapeutic agent to said subject. The oligonucleotide or oligonucleotide analog may be administered in a lipid formulation. The oligonucleotide may be administered systemically, such as topically, as with an eye drop, intracamerally, intravitreously, orally, intravenously, intraarterially, and intramuscularly, or may be administered intra-ocularly, including to the corneal endothelium. The oligonucleotide may be administered in a saline or buffered saline solution.

The oligonucleotide may be a guide RNA (gRNA) complementary to target DNA sequence followed by protospacer sequence motif (PAM) flanking the CTG18.1 locus in TCF4, and a gene editing construct is co-administered with said gRNA. The oligonucleotide may be a CUG repeat RNA targeting single guide RNA (sgRNA) comprising a poly-CAG spacer sequence, and a RNA targeting nuclease-dead Cas9 or other RNA targeting construct is co-administered with said sgRNA. The single guide RNA may comprise the sequence of any of SEQ ID NOs: 81-130. The single guide RNA may comprise the sequence CAG, or any of SEQ ID NOs: 68-73. Dual guide RNAs may be used to excise the (CTG,CAG)n DNA tract of TCF4 in corneal endothelial cells. Dual guide RNAs may comprise the sequence of any of SEQ ID NOs: 81-130. The oligonucleotide analog may be a peptide-nucleic acid (PNA), such as a PNA further comprising a cationic peptide. The oligonucleotide analog may be locked nucleic acid (LNA), such as a LNA further comprising a cationic peptide. The oligonucleotide may lack bases that recruit RNaseH. The oligonucleotide may recruit RNase H. The oligonucleotide may be administered more than once, such as at least about once every week.

The oligonucleotide may comprise a lipid. The oligonucleotide may be administered as a duplex with a complementary lipid-conjugated oligonucleotide. The lipid may be a biocleavable lipid. The biocleavable lipid may be conjugated to the oligonucleotide by a reducible linkage, nuclease-sensitive linkage, or protease-sensitive linkage. The lipid may be tocopheryl. The lipid may be cholesteryl. The lipid may be conjugated to an oligonucleotide by a phosphate, modified phosphate, amide, carbonate, carbamate, or triazole linkage.

The oligonucleotide may target repeat CUG RNA or intron 2 of TCF5 with CTG18.1 triplet repeat polymorphism. The oligonucleotide may target repeat CUG RNA or the 3' UTR of the DMPK gene with CTG triplit repeat polymorphism. Oligonucleotides targeting CUG RNA may comprise CAG sequences which target CUG repeats. Such RNAs may comprise the sequence of any of SEQ ID NOS: 1-4, 26-29, 43-50, or 51-80.

Provided herein is a method of treating a subject with Fuchs endothelial corneal dystrophy, comprising administering at least one oligonucleotide comprising at least two repeats of the sequence CAG to the subject. The method may further comprise administering at least one gene editing construct to the patient. Administration of the at least one gene editing construct may be concurrent or subsequent to administration of the at least one oligonucleotide. The gene editing construct may comprise a CRISPR-Cas9 or Cas12a construct, or an inactivated Cas9 or Cas12a construct.

Provided herein are compositions comprising an oligonucleotide comprising at least 2 CAG repeats, and an inactivated Cas9 or Cas12a construct. The oligonucleotide or oligonucleotide may be 13 to 25 nucleotides in length and at least 90% complementary to RNA sequences within intron 2 of TCF4 or the 3'-UTR of DMPK, and is designed to elicit cleavage of its RNA target by RNase H. The oligonucleotide may be hybridized to a complementary lipid-conjugated oligonucleotide. The oligonucleotide or oligonucleotide analog may comprise one or more chemically modified nucleobases, such as those to render the oligonucleotide nuclease-resistant, such as with a modified sugar moiety (i.e. a high-affinity sugar modification such as a bicyclic sugar moiety or a 2'-modified sugar moiety) or a modified internucleoside linkage. In some aspects, a bicyclic sugar moiety is a 4' to 2' bicyclic sugar moiety (such as a 4'-CH$_2$—O-2' or 4'-CH(CH$_3$)—O-2' bicyclic sugar moiety), a tricyclic moiety, or a morpholino moiety (such as a phosphorodiamidate morpholino moiety). Each 4' to 2' bridge may independently comprise from 2 to 4 linked groups independently selected from —[C(Ra)(Rb)]y-, —C(Ra)=C(Rb)—, —C(Ra)=N—, —C(=NRa)—, —C(=O)—, —C(=S)—, —O—, —Si(Ra)2-, —S(=O)x-, and —N(R1)-; wherein x is 0, 1, or 2; y is 1, 2, 3, or 4; each Ra and Rb is, independently, H, a protecting group, hydroxyl, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_9$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ1, NJ1J2, SJ1, N3, COOJ1, acyl (C(=O)—H), substituted acyl, CN, sulfonyl $(S(=O)_2$-J1), or sulfoxyl $(S(=O)$-J1); and each J1 and J2 is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_{20}$ aryl, substituted $C_5$-$C_9$ aryl, acyl (C(=O)—H), substituted acyl, a heterocycle radical, a substituted heterocycle radical, $C_1$-$C_6$ aminoalkyl, substituted $C_1$-$C_6$ aminoalkyl or a protecting group. In some aspects, each 4' to 2' bridge is independently —[C(Rc)(Rd)] n-, —[C(Rc)(Rd)]n-O—, —C(RcRd)-N(Re)-O— or —C(ReRd)-O—N(Re)-, wherein each Rc and Rd is independently hydrogen, halogen, substituted or unsubstituted $C_1$-$C_6$ alkyl; and each Re is independently hydrogen or substituted or unsubstituted $C_1$-$C_6$ alkyl. In some aspects, each 4' to 2' bridge is independently a 4'-$(CH_2)_2$-2',4'-$(CH_2)_3$-2',4'-$CH_2$—O-2',4'-$CH(CH_3)$—O-2',4'—$(CH_2)_2$-0-2',4'—$CH_2$—O—N(Re)-2' and 4'-$CH_2$—N(Re)-O-2'-bridge.

In some aspects of the composition, the oligonucleotide comprises terminal dT residues or 3' and/or 5' 2'-O-methyl modifications. The oligonucleotide may comprise a central mismatch (within bases 9-14) with a target sequence comprising said repeating tri-nucleobase sequence, or a mismatch outside of the seed sequence (bases 2-8 within the guide strand complementary to the CUG target sequence). The oligonucleotide may comprise 4, 5, 6 or 7 repeats. The oligonucleotide may comprise nucleotides linked by phosphate internucleoside linkages, such as phosphorothioate linkages. In some aspects, each internucleoside linkage is a phosphorothioate linkage.

The oligonucleotide may comprise DNA nucleobases, RNA nucleobases or a mixture of DNA and RNA nucleobases. The oligonucleotide may comprise a lipid. The oligonucleotide may be administered as a duplex with a complementary lipid-conjugated oligonucleotide. The lipid may be a biocleavable lipid. The biocleavable lipid may be conjugated to the oligonucleotide by a reducible linkage, nuclease-sensitive linkage, or protease-sensitive linkage. The lipid may be tocopheryl. The lipid may be cholesteryl. The lipid may be conjugated to an oligonucleotide by a phosphate, modified phosphate, amide, carbonate, carbamate, or triazole linkage.

Provided herein is a single-stranded or double-stranded oligonucleotide of 15 to 30 nucleotides in length that recruits the RNA interference machinery to target RNA within intron 2 of TCF4 or the 3'-UTR of DMPK. In some aspects, the oligonucleotide sequence is fully complementary to its target in intron 2 of TCF4 or the 3'-UTR of DMPK. In some aspects, the oligonucleotide comprises a sequence containing 1-3 mismatched nucleotides relative to its target in intron 2 of TCF4 or the 3'-UTR of DMPK.

The oligonucleotide may be hybridized to a complementary lipid-conjugated oligonucleotide. The oligonucleotide or oligonucleotide analog may comprise one or more chemically modified nucleobases, such as those to render the oligonucleotide nuclease-resistant, such as with a modified sugar moiety (i.e. a high-affinity sugar modification such as a bicyclic sugar moiety or a 2'-modified sugar moiety) or a modified internucleoside linkage. In some aspects, a bicyclic sugar moiety is a 4' to 2' bicyclic sugar moiety (such as a 4'-$CH_2$—O-2' or 4'-$CH(CH_3)$—O-2' bicyclic sugar moiety), a tricyclic moiety, or a morpholino moiety (such as a phosphorodiamidate morpholino moiety). Each 4' to 2' bridge may independently comprise from 2 to 4 linked groups independently selected from —[C(Ra)(Rb)]y-, —C(Ra)=C(Rb)—, —C(Ra)=N—, —C(=NRa)—, —C(=O)—, —C(=S)—, —O—, —Si(Ra)2-, —S(=O)x-, and —N(R1)-; wherein x is 0, 1, or 2; y is 1, 2, 3, or 4; each Ra and Rb is, independently, H, a protecting group, hydroxyl, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_9$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ1, NJ1J2, SJ1, N3, COOJ1, acyl (C(=O)—H), substituted acyl, CN, sulfonyl $(S(=O)_2$-J1), or sulfoxyl $(S(=O)$-J1); and each J1 and J2 is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_{20}$ aryl, substituted $C_5$-$C_9$ aryl, acyl (C(=O)—H), substituted acyl, a heterocycle radical, a substituted heterocycle radical, $C_1$-$C_6$ aminoalkyl, substituted $C_1$-$C_6$ aminoalkyl or a protecting group. In some aspects, each 4' to 2' bridge is independently —[C(Rc)(Rd)] n-, —[C(Rc)(Rd)]n-O—, —C(RcRd)-N(Re)-O— or —C(ReRd)-O—N(Re)-, wherein each Rc and Rd is independently hydrogen, halogen, substituted or unsubstituted $C_1$-$C_6$ alkyl; and each Re is independently hydrogen or substituted or unsubstituted $C_1$-$C_6$ alkyl. In some aspects, each 4' to 2' bridge is independently a 4'-$(CH_2)_2$-2',4'-$(CH_2)_3$-2',4'-$CH_2$—O-2',4'-$CH(CH_3)$—O-2',4'-$(CH_2)_2$-0-2', 4'-$CH_2$—O—N(Re)-2' and 4'-$CH_2$—N(Re)-O-2'-bridge.

In some aspects of the composition, the oligonucleotide comprises terminal dT residues or 3' and/or 5' 2'-O-methyl modifications. The oligonucleotide may comprise a central mismatch (within bases 9-14) with a target sequence comprising said repeating tri-nucleobase sequence, or a mismatch outside of the seed sequence (bases 2-8 within the guide strand complementary to the CUG target sequence). The oligonucleotide may comprise 4, 5, 6 or 7 repeats. The oligonucleotide may comprise nucleotides linked by phosphate internucleoside linkages, such as phosphorothioate linkages. In some aspects, each internucleoside linkage is a phosphorothioate linkage.

The oligonucleotide may comprise DNA nucleobases, RNA nucleobases or a mixture of DNA and RNA nucleobases. The oligonucleotide may comprise a lipid. The oligonucleotide may be administered as a duplex with a complementary lipid-conjugated oligonucleotide. The lipid may be a biocleavable lipid. The biocleavable lipid may be conjugated to the oligonucleotide by a reducible linkage, nuclease-sensitive linkage, or protease-sensitive linkage. The lipid may be tocopheryl. The lipid may be cholesteryl. The lipid may be conjugated to an oligonucleotide by a phosphate, modified phosphate, amide, carbonate, carbamate, or triazole linkage.

Provided herein is a gene editing guide sequence of 30 to 120 nucleotides in length that binds within the genomic region corresponding to intron 2 of TCF4 or the 3'-UTR of DMPK. Gene editing guide sequences may also be used as a set of two gene editing guide sequences of 30 to 120 nucleotides in length that flank repeat sequences in the genomic region corresponding to intron 2 of TCF4 or the 3'-UTR of DMPK. Said gene editing guide sequence analog may comprise one or more chemically modified nucleobases. The gene editing guide sequence may be hybridized to a complementary lipid-conjugated oligonucleotide. The gene editing guide sequence may comprise one or more chemically modified nucleobases, such as those to render the gene editing guide sequence nuclease-resistant, such as with a modified sugar moiety (i.e. a high-affinity sugar modification such as a bicyclic sugar moiety or a 2'-modified sugar moiety) or a modified internucleoside linkage. In some aspects, a bicyclic sugar moiety is a 4' to 2' bicyclic sugar moiety (such as a 4'-$CH_2$—O-2' or 4'-$CH(CH_3)$—O-2' bicyclic sugar moiety), a tricyclic moiety, or a morpholino moiety (such as a phosphorodiamidate morpholino moiety). Each 4' to 2' bridge may independently comprise from 2 to 4 linked groups independently selected from —[C(Ra)(Rb)]y-, —C(Ra)=C(Rb)—, —C(Ra)=N—, —C(=NRa)—, —C(=O)—, —C(=S)—, —O—, —Si(Ra)2-, —S(=O)x-, and —N(R1)-; wherein x is 0, 1, or 2; y is 1, 2, 3, or 4; each Ra and Rb is, independently, H, a protecting group, hydroxyl, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_9$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ1, NJ1J2, SJ1, N3, COOJ1, acyl (C(=O)—H), substituted acyl, CN, sulfonyl (S(=O)2-J1), or sulfoxyl (S(=O)-J1); and each J1 and J2 is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_{20}$ aryl, substituted $C_5$-$C_9$ aryl, acyl (C(=O)—H), substituted acyl, a heterocycle radical, a substituted heterocycle radical, $C_1$-$C_6$ aminoalkyl, substituted $C_1$-$C_6$ aminoalkyl or a protecting group. In some aspects, each 4' to 2' bridge is independently —[C(Rc)(Rd)]n-, —[C(Rc)(Rd)]n-O—, —C(RcRd)-N(Re)-O— or —C(ReRd)-O—N(Re)-, wherein each Rc and Rd is independently hydrogen, halogen, substituted or unsubstituted $C_1$-$C_6$ alkyl; and each Re is independently hydrogen or substituted or unsubstituted $C_1$-$C_6$ alkyl. In some aspects, each 4' to 2' bridge is independently a 4'-$(CH_2)_2$-2',4'-$(CH_2)_3$-2',4'-$CH_2$—O-2',4'-$CH(CH_3)$—O-2',4'-$(CH_2)_2$-0-2', 4'-$CH_2$—O—N(Re)-2' and 4'-$CH_2$—N(Re)-O-2'-bridge.

In some aspects of the composition, the gene editing guide sequence comprises terminal dT residues or 3' and/or 5' 2'-O-methyl modifications. The gene editing guide sequence may comprise a central mismatch (within bases 9-14) with a target sequence comprising said repeating tri-nucleobase sequence, or a mismatch outside of the seed sequence (bases 2-8 within the guide strand complementary to the CUG target sequence). The gene editing guide sequence may comprise 4, 5, 6 or 7 repeats. The gene editing guide sequence may comprise nucleotides linked by phosphate internucleoside linkages, such as phosphorothioate linkages. In some aspects, each internucleoside linkage is a phosphorothioate linkage.

The gene editing guide sequence may comprise DNA nucleobases, RNA nucleobases or a mixture of DNA and RNA nucleobases. The gene editing guide sequence may comprise a lipid. The gene editing guide sequence may be administered as a duplex with a complementary lipid-conjugated oligonucleotide. The lipid may be a biocleavable lipid. The biocleavable lipid may be conjugated to the gene editing guide sequence by a reducible linkage, nuclease-sensitive linkage, or protease-sensitive linkage. The lipid may be tocopheryl. The lipid may be cholesteryl. The lipid may be conjugated to an gene editing guide sequence by a phosphate, modified phosphate, amide, carbonate, carbamate, or triazole linkage.

Provided herein is a repeat-RNA-targeting guide sequence comprising at least 2 CAG repeats that binds to CUG repeat RNA corresponding to intron 2 of TCF4 or the 3'-UTR of DMPK. The repeat-RNA-targeting guide sequence may further comprise an RNA-targeting construct, such as a CRISPR construct. The CRISPR construct may be a Cas9 or Cas12a construct, or a nuclease deficient mutant thereof. The RNA-targeting construct may be separate from the repeat-RNA-targeting guide sequence, such as present as a separate DNA molecule, mRNA, or protein.

Repeat-RNA-targeting guide sequences may also be used as a set of two repeat-RNA-targeting guide sequences of 30 to 120 nucleotides in length that flank repeat sequences in the genomic region corresponding to intron 2 of TCF4 or the 3'-UTR of DMPK. Said repeat-RNA-targeting guide sequence may comprise one or more chemically modified nucleobases. The repeat-RNA-targeting guide sequence may be hybridized to a complementary lipid-conjugated oligonucleotide. The repeat-RNA-targeting guide sequence may comprise one or more chemically modified nucleobases, such as those to render the repeat-RNA-targeting guide sequence nuclease-resistant, such as with a modified sugar moiety (i.e. a high-affinity sugar modification such as a bicyclic sugar moiety or a 2'-modified sugar moiety) or a modified internucleoside linkage. In some aspects, a bicyclic sugar moiety is a 4' to 2' bicyclic sugar moiety (such as a 4'-$CH_2$—O-2' or 4'-$CH(CH_3)$—O-2' bicyclic sugar moiety), a tricyclic moiety, or a morpholino moiety (such as a phosphorodiamidate morpholino moiety). Each 4' to 2' bridge may independently comprise from 2 to 4 linked groups independently selected from —[C(Ra)(Rb)]y-, —C(Ra)=C(Rb)—, —C(Ra)=N—, —C(=NRa)—, —C(=O)—, —C(=S)—, —O—, —Si(Ra)2-, —S(=O)x-, and —N(R1)-; wherein x is 0, 1, or 2; y is 1, 2, 3, or 4; each Ra and Rb is, independently, H, a protecting group, hydroxyl, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_9$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ1, NJ1J2, SJ1, N3, COOJ1, acyl (C(=O)—H), substituted acyl, CN, sulfonyl $(S(=O)_2$-J1), or sulfoxyl (S(=O)-J1); and each J1 and J2 is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_5$-$C_{20}$ aryl, substituted $C_5$-$C_9$ aryl, acyl (C(=O)—H), substituted acyl, a heterocycle radical, a substituted heterocycle radical, $C_1$-$C_6$ aminoalkyl, substituted $C_1$-$C_6$ aminoalkyl or a protecting group. In some aspects, each 4' to 2' bridge is independently —[C(Rc)(Rd)]n-, —[C(Rc)(Rd)]n-O—, —C(RcRd)-N(Re)-O— or —C(ReRd)-O—N(Re)-, wherein each Rc and Rd is independently hydrogen, halogen, substituted or unsubstituted $C_1$-$C_6$ alkyl; and each Re is independently hydrogen or substituted or unsubstituted $C_1$-$C_6$ alkyl. In some aspects, each 4' to 2' bridge is independently a 4'-$(CH_2)_2$-2', 4'-$(CH_2)_3$-2',4'-$CH_2$—O-2',4'-$CH(CH_3)$—O-2',4'-$(CH_2)_2$-0-2',4'-$CH_2$—O—N(Re)-2' and 4'-$CH_2$—N(Re)-O-2'-bridge.

In some aspects of the composition, the repeat-RNA-targeting guide sequence comprises terminal dT residues or 3' and/or 5' 2'-O-methyl modifications. The repeat-RNA-targeting guide sequence may comprise a central mismatch (within bases 9-14) with a target sequence comprising said repeating tri-nucleobase sequence, or a mismatch outside of the seed sequence (bases 2-8 within the guide strand complementary to the CUG target sequence). The repeat-RNA-targeting guide sequence may comprise 4, 5, 6 or 7 repeats. The repeat-RNA-targeting guide sequence may comprise nucleotides linked by phosphate internucleoside linkages, such as phosphorothioate linkages. In some aspects, each internucleoside linkage is a phosphorothioate linkage.

The repeat-RNA-targeting guide sequence may comprise DNA nucleobases, RNA nucleobases or a mixture of DNA and RNA nucleobases. The repeat-RNA-targeting guide sequence may comprise a lipid. The repeat-RNA-targeting guide sequence may be administered as a duplex with a complementary lipid-conjugated oligonucleotide. The lipid may be a biocleavable lipid. The biocleavable lipid may be conjugated to the repeat-RNA-targeting guide sequence by a reducible linkage, nuclease-sensitive linkage, or protease-sensitive linkage. The lipid may be tocopheryl. The lipid may be cholesteryl. The lipid may be conjugated to an repeat-RNA-targeting guide sequence by a phosphate, modified phosphate, amide, carbonate, carbamate, or triazole linkage.

It is contemplated that any embodiment discussed in this specification can be implemented with respect to any method or composition of the disclosure, and vice versa. Furthermore, compositions of the disclosure can be used to achieve methods of the disclosure.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment, the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIGS. 1A-B) Scheme showing TCF4 pre-mRNA and antisense transcripts with the location of the expanded CUG and CAG repeat regions. (FIG. 1C) FISH images of $CUG^{exp}$ RNA foci in two patient-derived FECD endothelial cell lines (F35T, F45) compared with a healthy control endothelial cell line (Zante). A $(CAG)_6CA$ RNA probe was used for detecting the sense $CUG^{exp}$ foci. (FIG. 1D) Representative images of sense $CUG^{exp}$ or antisense $CAG^{exp}$ RNA foci in one FECD patient corneal tissue compared with a healthy control endothelial tissue. A $(CUG)_6CU$ RNA probe was used for detecting the antisense $CAG^{exp}$ foci.

FIGS. 2A-I. Quantitative analysis of sense and antisense foci in FECD. (FIG. 2A) Summary table of patient corneal endothelial tissue samples. Sample 2014-1670 is a healthy control. CA052 is a FECD tissue without CTG expansion (negative control). Twenty FECD samples are with CTG expansions. Sense foci were found in 84.0% of cells (standard deviation (SD)=10.4) compared to the antisense foci found in 10.6% of the cells (SD=9.1) (P=2.1×10$^{-24}$). Foci are not numerous, with 1.8 sense foci (SD=4.7) and 0.13 antisense foci per cell (SD=0.13), (P=2.9×10$^{-13}$). n=300-500 cells evaluated per patient sample. (FIG. 2B) Graphs show significant negative correlation between % or number of sense RNA foci and age of subject. (FIG. 2C) There is a trend towards a positive correlation between sense foci and triplet repeat allele length. (FIG. 2D) Copy number of GAPDH, TCF4 intron 2, TCF4 exon 2/3, TCF4 exon 18 transcripts measured with qPCR in F35T cell line. (FIG. 2E) Analysis of sense foci in F35T cells. (FIG. 2F) Analysis of foci in F35T cells. (FIG. 2G) Analysis of foci copy number per F35T cell. (FIG. 2H) Analysis of foci copy number per cell in control tissue. (FIG. 2I) Analysis of foci copy number per cell in FECD tissue.

(FIG. 3A) List of CUG repeat-targeting LNA-ASOs. LNA base: bold; DNA base: normal caps; All oligomers are fully phosphorothioate backbones. $T_m$ was detected by equal amount (1 µM each) of LNAs with complementary DNAs. LNA 1=SEQ ID NO: 26; LNA 2=SEQ ID NO: 27; LNA 3=SEQ ID NO: 28; LNA 4=SEQ ID NO: 29. (FIG. 3B) Effect of LNAs on inhibition of $CUG^{exp}$ RNA foci in F35T cells. CM: non-complementary negative control duplex RNA; LC: LNA analog of CM. (FIG. 3C) Effect of LNAs on inhibition of $CUG^{exp}$ foci in F45 cells. Error bars represent SEM. *p<0.05; p<0.01; *p<0.001 compared with control LC. At least one hundred cells were analyzed for each experiment. (FIG. 3D) Effect of COL5A1 mRNA after treatment with 25 nM of LNA-ASOs.

FIGS. 4A-E. LNA effectively reduced $CUG^{exp}$ foci and reversed mis-splicing in ex vivo human FECD corneas. (FIG. 4A) Scheme outlining the experiment in ex vivo human corneas. Pairs of corneas from FECD-patient donors and control donors were obtained from eye bank and were treated with ASOs. Corneas from right eyes were used to assess $CUG^{exp}$ foci. Corneas from corresponding left eyes were used to assess splicing events. (FECD Tissue 1 from 54 year-old FECD-patient donor, 17/110 CTG repeat; FECD Tissue 2 from 51 year-old FECD-patient donor, 13/130 CTG repeat). (FIG. 4B) FISH images of FECD corneal endothelial tissue 1 treated with control LNA-LC and LNA 1. (FIG. 4C) Effect of LNA 1 on inhibition of $CUG^{exp}$ foci in two FECD corneas (FIG. 4D) RT-PCR gel images showing effect of LNA 1 on the splicing of INF2, MBNL1, and ADD3 in FECD corneal endothelial tissues. Flanking RT-PCR primers were used to assess exon inclusion or exon exclusion. (FIG. 4E) Averaged quantitative bar graphs of splicing events shown in FIG. 4D. ImageJ was used to compare density of bands on gel. Error bars represent SEM.

FIGS. 5A-D. Verification of TCF4 antisense transcript by sequence-specific PCR in F35T patient-derived endothelial cells. (FIG. 5A) Scheme showing sequence-specific RT primers for cDNA generation and PCR primers. (FIG. 5B)

Sequences of primers for reverse transcription and PCR reactions. (FIG. 5C) Image of PCR products after sequence-specific RT reaction for antisense transcript. (FIG. 5D) Sanger sequencing of PCR amplicons.

(FIG. 6A) There is no significant correlation between antisense foci and patient age. (FIGS. 6B-C) Graphs showing that there is little correlation between sense or antisense foci with patient sex.

FIGS. 11A-C. Demographics data of ex vivo human corneas. (FIG. 11A) Summary table of FECD-patient and control donors. (FIGS. 11B-C) Specular microscopy imaging of corneal endothelium. Dark spots correlate to focal excrescences (guttae) of Descemet's membrane, the basement membrane of the endothelium, which are diagnostic of FECD.

FIGS. 12A-D. Inhibition of $CUG^{exp}$ RNA foci by repeat-targeting duplex RNAs in F35T (CUG 22/1500) or F45 (CUG16/71) endothelial cell line evaluated by fluorescent microscopy. (FIG. 12A) List of duplex RNAs. Mismatched base is shown in bold and underlined. 2'-O-Me modified RNA base is in lowercase. dT, DNA base T. CM: non-complementary negative control siRNA. (FIG. 12B) Effect of fully complementary duplex RNAs on inhibition of $CUG^{exp}$ RNA foci in F35T cells. (FIG. 12C) Effect of fully complementary duplex RNAs on inhibition of $CUG^{exp}$ RNA foci in F45 cells. (FIG. 12D) Duplex RNAs with central mismatches inhibit $CUG^{exp}$ RNA foci in F35T cell line. Error bars represent SEM. *p<0.05; p<0.01; *p<0.001 compared with control CM. At least one hundred cells were analyzed for each experiment.

FIGS. 13A-B. Inhibition of $CUG^{exp}$ foci by LNA-gapmers in F35T (CUG 22/1500) endothelial cell line. (FIG. 13A) List of LNA-gapmers. LNA base: Bold; DNA base: normal caps; All oligomers are fully phosphorothioate backbones. (FIG. 13B) Effect of LNA-gapmers on inhibition of CUG RNA foci in F35T cells. Error bars represent SEM. *p<0.05; p<0.01; *p<0.001 compared with control LC. At least one hundred cells were analyzed for each experiment.

FIG. 14A-B. Effect of duplex RNAs or LNA-gapmers on TCF4 expression in F35T (CUG 22/1500) endothelial cell line. (FIG. 14A) Quantitative PCR showing effect of duplex RNAs on TCF4 mRNA & intron 2 levels. E19: duplex RNA targeting the TCF4 exon 19. (FIG. 14B) Quantitative PCR showing effect of LNA-gapmers on levels of TCF4 transcript.

(FIG. 17A) Detection of CUG RNA foci by RNA-FISH in F35T cells transfected with dCas9-GFP and CUG1 sgRNA. (FIG. 17B) Cell number of GFP- and GFP+ in F35T cells transfected with plasmids are shown. Results are shown as the mean±SD. Two independent experiments were performed. According to this result, average transfection efficiency of F35T cells is calculated as 25/153=16.3%. For each experiment, at least 10 images were analyzed. (FIG. 17C) Quantification of percentage of cells contain RNA foci in FIG. 17A. As shown in FIG. 17B, in transfected F35T cells, GFP- cells and GFP+ cells were analyzed separately. Results are shown as the mean±SD. n=2 independent experiments. (FIG. 17D) Quantification of number of foci per cell in (A). Data were analyzed as FIG. 17C. Results are shown as the mean±SD. n=2 independent experiments.

FIGS. 18A-D. Inhibition of Mahal expression by LNA-gapmers. (A) List of LNA-gapmers. LNA base: Bold; DNA base: normal caps; All oligomers are fully phosphorothioate backbones. (B) Effect on inhibition of Malat1 by 25 or 5 nM concentrations of LNA-gapmers in F35T cells. Error bars represent SEM. (C-D) Effect on inhibition of Malat1 by 5 μM concentrations of LNA-gapmers in two human corneas.

DETAILED DESCRIPTION

Figure 1A:
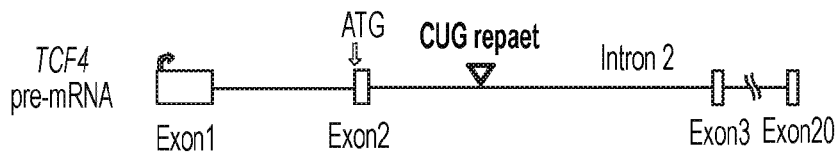
FIGS. 1A-D. Sense and antisense RNA foci are detected in FECD corneal endothelial cells by fluorescent microscopy.
Figure 1B:
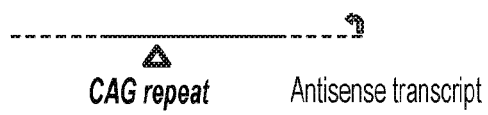

Fuchs' endothelial corneal dystrophy (FECD) is an age-related disorder impacting 5% of whites over the age of 40 years and is the leading indication of corneal transplantation in the United States. A CTG expansion in intron 2 of the TCF4 gene (CTG18.1) forms expanded CUG repeat RNA foci and is associated with 70% of FECD cases in whites making it the most common repeat expansion disorder. The present inventors sought to test duplex RNA and single-stranded antisense oligonucleotide inhibitors of $CUG^{exp}$ foci formation. The present inventors also sought to test CUG repeat RNA targeting Cas9 small guide RNA inhibitors of $CUG^{exp}$ foci formation.

Using a patient-derived endothelial cell culture model system, the inventors assessed the efficacy of synthetic nucleic acids to abrogate $CUG^{exp}$ foci formation. Anti-CUG repeat constructs targeting the repeat reduce $CUG^{exp}$ RNA foci after double transfection. Thus, the inventors demonstrate the feasibility of inhibitors of $CUG^{exp}$ foci in FECD. Additionally, the high prevalence of disease and relative accessibility of the eye to small molecules make the triplet repeat expansion in FECD an ideal therapeutic target for engineered synthetic nucleic acids. These and other aspects of the disclosure are discussed in detail below.

Synthetic nucleic acids were were also designed in the form of sgRNAs to perform dual sgRNA-guided excision of the (CTG,CAG)n DNA tract in the TCF4 gene responsible for Fuchs' endothelial corneal dystrophy (FECD) with CRISPR/Cas9 technology. Additionally, the inventors designed, tested, and demonstrate the proficiency of sgRNAs to target and eliminate CUG repeat RNA foci in FECD corneal endothelial cells with the CTG triplet repeat expansions in the TCF4 gene using RNA-targeting Cas9 system.

I. DEFINITIONS

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Certain such techniques and procedures may be found for example in "Carbohydrate Modifications in Antisense Research" Edited by Sangvi & Cook, American Chemical Society, Washington D.C., 1994; "Remington's Pharmaceutical Sciences," Mack Publishing Co., Easton, Pa., 21.sup.st edition, 2005; "Antisense Drug Technology, Principles, Strategies, and Applications" Edited by Stanley T. Crooke, CRC Press, Boca Raton, Fla.; and Sambrook et al., "Molecular Cloning, A laboratory Manual," 2nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-F ANA" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. In some embodiments, the modified sugar moiety may also include additional rings, such as a third ring. In certain such embodiments, a bridge may connect the 3'-carbon and the 4'-carbon of a deoxyribofuranosyl sugar, and a second bridge may connect the 5'-carbon of the deoxyribofuranosyl group with an atom of the first bridge.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e., no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "tricyclic nucleoside" means a nucleoside comprising a tricyclic nucleoside. The term "tcDNA" is used to describe a DNA structure comprising at least one tricyclic nucleoside. Bicyclic nucleosides and tricyclic nucleosides may be present in the same nucleic acid molecule.

As used herein, "constrained ethyl nucleoside" or "cEt" means a nucleoside comprising a bicyclic sugar moiety comprising a 4'-CH(CH$_3$)—O-2' bridge.

As used herein, "locked nucleic acid nucleoside" or "LNA" means a nucleoside comprising a bicyclic sugar moiety comprising a 4'-CH$_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 2'-endo furanosyl nucleosides and RNA surrogates.

As used herein, "2'-endo-furanosyl nucleoside" means an RNA-like nucleoside that comprises a substituted sugar moiety that has a 2'-endo conformation. 2'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "phosphorous moiety" refers to a to monovalent P(V) phosphorus radical group. In certain embodiments, a phosphorus moiety is selected from: a phosphate, phosphonate, alkylphosphonate, vinylphosphonate, aminoalkyl phosphonate, phosphorothioate, phosphoramidite, alkylphosphonothioate, phosphorodithioate, thiophosphoramidate, phosphotriester and the like.

The term "phosphate moiety" as used herein, refers to a terminal phosphate group that includes unmodified phosphates (—O—P(=O)(OH)OH) as well as modified phosphates. Modified phosphates include but are not limited to phosphates in which one or more of the O and OH groups is replaced with H, O, S, N(R), alkyl, alkenyl, or alkynol where R is H, an amino protecting group or unsubstituted or substituted alkyl.

As used herein, "phosphate stabilizing modification" refers to a modification that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phophate group includes but is not limited to resistance to removal by phosphatases. Phosphate stabilizing modifications include, but are not limited to, modification of one or more of the atoms that binds directly to the phosphorus atom, modification of one or more atoms that link the phosphorus to the 5'-carbon of the nucleoside, and modifications at one or more other positions of the nucleoside that result in stabilization of the phosphate. In certain embodiments, a phosphate stabilizing modification comprises a carbon linking the phosphorous atom to the 5'-carbon of the sugar. Phosphate moieties that are stabilized by one or more phosphate stabilizing modification are referred to herein as "stabilized phosphate moieties."

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids.

As used herein, "terminal group" means one or more atom(s) attached to either, or both, the 3' end or the 5' end of an oligonucleotide. In certain embodiments a terminal group is a conjugate group. In certain embodiments, a terminal group comprises one or more terminal nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "single-stranded" means an oligomeric compound that is not hybridized to its complement and which lacks sufficient self-complementarity to form a stable self-duplex.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity is a reduction of a gain-of-function of an expanded repeat-containing nucleic acid. In certain embodiments, antisense activity is a correction of a loss-of-function of an expanded repeat-containing nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenylation, addition of 5'-cap), and translation.

As used herein, "target nucleic acid" means a nucleic acid molecule to which an antisense compound hybridizes.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, the term "expanded repeat-containing RNA" means a mutant RNA molecule having a nucleobase sequence that includes a repeat region having a predetermined number of nucleobases repeats, wherein the presence or length of the repeat region affects the normal processing, function, or activity of the RNA or corresponding protein.

As used herein, the term "corresponding wild-type RNA" means the non-mutant version of the expanded repeat-containing RNA having normal function and activity. Typically, corresponding wild-type RNA molecules comprise a repeat region which is shorter than that of an expanded repeat-containing RNA.

As used herein, "selectivity" refers to the ability of an antisense compound to exert an antisense activity on a target nucleic acid to a greater extent than on a non-target nucleic acid.

As used herein, "mutant selective" refers to a compound that has a greater effect on a mutant nucleic acid than on the corresponding wild-type nucleic acid. In certain embodiments, the effect of a mutant selective compound on the mutant nucleic acid is 2, 3, 4, 5, 6, 7, 8, 9, 10, 15, 20, 25, 30, 35, 40, 50, 100 or more than 100 times greater than the effect of the mutant selective compound on the corresponding wild-type nucleic acid. In certain embodiments, such selectivity results from greater affinity of the mutant selective compound for the mutant nucleic acid than for the corresponding wild-type nucleic acid. In certain embodiments, selectivity results from a difference in the structure of the mutant compared to the wild-type nucleic acid. In certain embodiments, selectivity results from differences in processing or sub-cellular distribution of the mutant and wild-type nucleic acids. In certain embodiments, some selectivity may be attributable to the presence of additional target sites in a mutant nucleic acid compared to the wild-type nucleic acid. For example, in certain embodiments, a target mutant allele comprises an expanded repeat region comprising more repeats than the wild-type allele. Thus, the wild-type allele has fewer sites available for hybridization of an antisense compound targeting the repeat region. In certain embodiments, a mutant selective compound has selectivity greater than the selectivity predicted by the increased number of target sites. In certain embodiments, the ratio of inhibition of a mutant allele to a wild-type allele is equal to or greater than the ratio of the number of repeats in the mutant allele to the wild-type allele. In certain embodiments, the ratio of inhibition of a mutant allele to a wild-type allele is greater than the ratio of the number of repeats in the mutant allele to the wild-type allele.

As used herein, "gain-of-function activity" means a biological activity attributed to an expanded repeat-containing RNA. For example, an expanded repeat-containing RNA may gain the ability to sequester RNA-binding proteins in a manner that impairs normal cellular function, such as the normal action of RNA processing in the nucleus (see Cooper, T. (2009) Cell 136, 777-793; O'Rourke, J R (2009) J. Biol. Chem. 284 (12), 7419-7423).

As used herein, "nucleobase complementarity" or "complementarity" when in reference to nucleobases means a nucleobase that is capable of standard Watson-Crick base pairing with another nucleobase. For example, adenine (A) is complementary to thymine (T) or uracil (U), and cytosine is complementary to guanine. In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type of modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline. In certain embodiments, such sterile saline is buffered saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)Raa), carboxyl (—C(O)O—Raa), aliphatic groups, alicyclic groups, alkoxy, substituted oxy (—O—Raa), aryl, aralkyl, heterocyclic radical, heteroaryl, heteroarylalkyl, amino (—N(Rbb)(Rcc)), imino(=NRbb), amido (—C(O)N(Rbb)(Rcc) or —N(Rbb)C(O)Raa), azido (—N3), nitro (—NO2), cyano (—CN), carbamido (—OC(O)N(Rbb)(Rcc) or —N(Rbb)C(O)ORaa), ureido (—N(Rbb)C(O)N(Rbb)(Rcc)), thioureido (—N(Rbb)C(S)N(Rbb)-(Rcc)), guanidinyl (—N(Rbb)C(=NRbb)N(Rbb)(Rcc)), amidinyl (—C(=NRbb)N(Rbb)(Rcc) or —N(Rbb)C(=NRbb)(Raa)), thiol (—SRbb), sulfinyl (—S(O)Rbb), sulfonyl (—S(O)2Rbb) and sulfonamidyl (—S(O)2N(Rbb)(Rcc) or —N(Rbb)S—(O)2Rbb), wherein each Raa, Rbb and Rcc is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C1-C12 alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between inventorsen an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted C1-C12 alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a C1-C12 alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "parenteral administration," means administration through injection or infusion. Parenteral administration includes, but is not limited to, subcutaneous administration, intravenous administration, or intramuscular administration.

As used herein, "systemic administration" means administration to an area other than the intended locus of activity. Examples or systemic administration are subcutaneous administration and intravenous administration, and intraperitoneal administration.

As used herein, "subcutaneous administration" means administration just below the skin.

As used herein, "intravenous administration" means administration into a vein.

As used herein, "cerebrospinal fluid" or "CSF" means the fluid filling the space around the brain and spinal cord.

As used herein, "administration into the cerebrospinal fluid" means any administration that delivers a substance directly into the CSF.

As used herein, "intracerebroventricular" or "ICV" mean administration into the ventricular system of the brain.

As used herein, "intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

As used herein, "intracameral" means administration directly into the anterior chamber of the eye.

As used herein, "intravitreal" means administration directly to the intravitreal compartment of the eye.

As used herein, "topical" means administration directly to the ocular surface of the eye.

II. FUCHS' ENDOTHELIAL CORNEAL DYSTROPHY

Fuchs' dystrophy, also known as Fuchs' corneal endothelial dystrophy or FCD, also known as Fuchs' endothelial corneal dystrophy or FECD, is a slowly progressing corneal dystrophy that usually affects both eyes and is slightly more common in women than in men. Although doctors can often see early signs of Fuchs' dystrophy in people in their 30s and 40s, the disease rarely affects vision until people reach their 50s and 60s. The condition was first described by Austrian ophthalmologist Ernst Fuchs (1851-1930), after whom it is named. Cross-sectional studies suggest a relatively higher prevalence of disease in European countries relative to other areas of the world.

Fuchs' endothelial corneal dystrophy (FECD) is a degenerative disease of the corneal endothelium with accumulation of focal outgrowths called guttae (drops) and thickening of Descemet's membrane, leading to corneal edema and loss of vision. Corneal endothelial cells are the major "pump" cells of the cornea to allow for stromal clarity. In FECD, Descemet's membrane is grossly thickened with accumulation of abnormal wide-spaced collagen and numerous guttae. Corneal endothelial cells in end-stage FECD are reduced in number and appear attenuated, causing progressive stromal edema. Progressive endothelial cell loss causes relative influx of aqueous humor into the cornea, leading to swelling (corneal stromal edema), which results in distorted vision. Eventually, the epithelium also becomes edematous, resulting in more severe visual impairment. Focal areas or blisters of epithelial edema ("bullae") may be particularly painful.

The inheritance of FCED is autosomal dominant with genetic and environmental modifiers such as increased prevalence in the elderly and in females. Endothelial cell loss may be aggravated or accelerated by intraocular trauma or surgery. A common scenario involves excessive corneal swelling or edema following cataract surgery or other types of ocular surgery. Hence, patients with a history of Fuchs' dystrophy may be at a greater risk of corneal edema after ocular surgery as they have fewer functioning endothelial cells.

FECD is classified into four stages, from early signs of guttae formation to end-stage subepithelial scarring. Traditional diagnosis is made by biomicroscopic examination. Other modalities, such as corneal pachymetry, confocal biomicroscopy, and specular microscopy can be used in conjunction.

Exact pathogenesis is unknown but factors include endothelial cell apoptosis, sex hormones, inflammation, and aqueous humor flow and composition. Mutations in collagen VIII, a major component of Descemet's membrane secreted by endothelial cells, have been linked to the early-onset FCED.

At first, a person with symptomatic Fuchs' dystrophy will awaken with blurred vision and complaints of glare that gradually improve during the day. This occurs because the cornea is normally thicker in the morning; it retains fluids during sleep due to eyelids being closed, and that fluid in the cornea evaporates while one is awake. As the disease worsens, this swelling will remain persistent and reduce vision throughout the day. Researchers are finding that Fuchs' dystrophy is a genetically heterogeneous disease. Expanded trinucleotide repeats at the intronic CTG18.1 locus in intron 2 of TCF4 are associated with FECD in a majority of whites with the disorder (Wieben et al., 2012; Mootha et al., 2014). Certain genetic lesions have been correlated with more severe disease and earlier onset. Therefore some individuals may experience symptoms of the disease at a much earlier age, while others may not experience symptoms until late in life.

Medical treatment of FECD is utilized to treat symptoms of early disease. Medical management includes topical hypertonic saline, the use of a hairdryer to dehydrate the precorneal tear film, and therapeutic soft contact lenses. In using a hairdryer, the patient is instructed to hold a hairdryer at an arm's length or directed across the face, to dry out the epithelial blisters. This can be done two or three times a day. It has also been reported that botulinum toxin can produce improvement lasting several months. Definitive treatment, however, (especially with increased corneal edema) is surgical in the form of corneal transplantation.

Since 1998, new surgical modalities in the treatment of FECD have been developed, initially by Melles et al. These procedures, called posterior lamellar keratoplasty or endothelial keratoplasty, were initially popularized as deep lamellar endothelial keratoplasty (DLEK) and Descemet's stripping with endothelial keratoplasty (DSEK). DLEK and DSEK avoid some of the surgical complications of PKP such as wound dehiscence and high postoperative astigmatism. Since 2004, DSEK has become the dominant procedure for patients with corneal disease restricted to the endothelium. It can be technically easier for the surgeon compared to DLEK, and may provide superior visual results. With DSEK, patients must remain supine (face up positioning) for 24 or more hours following the procedure while the transplanted tissue adheres to the overlying cornea.

Improved surgical instrumentation for DSEK, such as DSEK graft injectors, and technical improvements in the surgical technique have facilitated reduced complications and the potential to perform DSEK through very small (3 mm) sutureless incision.

Recently, endothelial keratoplasty has been further refined to Descemet Membrane Endothelial Keratoplasty (DMEK), in which only a donor Descemet membrane and its endothelium is transplanted. With DMEK, 90% of cases achieve a best spectacle corrected visual acuity 20/40 or better, and 60% of cases 20/25 or better within 1-3 months, although complications such as graft failure and detachment remain challenges for the patient and surgeon.

More speculative future directions in the treatment of FECD include in vitro expansion of human corneal endothelial cells for transplantation, artificial corneas (keratoprosthesis), and genetic modification.

A greater understanding of FECD pathophysiology may assist in the future with the development of treatments to prevent progression of disease. Although much progress has been made in the research and treatment of FECD, many questions remain to be answered. The exact causes of illness, the prediction of disease progression and delivery of an accurate prognosis, methods of prevention and effective nonsurgical treatment are all the subject of inquiries that necessitate an answer. Increased attention must be given to research that can address the most basic questions of how disease develops: what is the biomolecular pathway implicated in disease, and what genetic or environmental factors contribute to its progression? In addition to shaping the understanding of FECD, identification of these factors would be essential for the prevention and management of this condition.

III. NUCLEIC ACIDS AND METHODS OF MODULATING GENE EXPRESSION

A. Oligonucleotide Agents

The oligonucleotide agents of the present disclosure bind to target sequences. More particularly, these are oligonucleotides and oligonucleotide analogs that target a repeating tri-nucleotide sequence comprising CAG/CUG. Alternatively, the oligonucleotide may target the CTG18.1 triplet repeat polymorphism in the TCF4 gene or intronic sequences flanking the CTG18.1 repeat. Alternatively, the oligonucleotide may target the 3' UTR CTG triplet repeat polymorphism in the DMPK or flanking sequences.

The length of the oligonucleotide may be 10-50 bases, and more specifically 13-30 bases, such as 13, 14, 15, 16, 17, 18, 19, 20, 21, 22, 23, 24, 25, 26, 27, 28, 29, or 30 nucleobases. The oligonucleotide or oligonucleotide analog may, in particular, be RNA and include one or more modified and/or non-natural nucleobases. The oligonucleotide or oligonucleotide analog may contain DNA as well as RNA nucleobases, such as terminal thymidine residues.

Particularly contemplated sequences include, but are not limited to, the following:

CAGCAGCAGCAGCAGCAGCdTdT (SEQ ID NO: 1)
dTdTCUCGUCGUCGUCGUCGUCG (SEQ ID NO: 3)
AGCAGCAGCAGCAGCAGCAdTdT (SEQ ID NO: 2)
dTdTUCGUCGUCGUCGUCGUCGU (SEQ ID NO: 4)

A design consideration is the placement of 1, 2, 3, 4 or 5 "mismatches" in the oligonucleotide or oligonucleotide analog as compared to the target sequence. In one embodiment, the mismatches are generally "centrally located" in the oligonucleotide or oligonucleotide analog, i.e., not located within the first two or last two bases of the oligonucleotide or oligonucleotide analog. A more restrictive definition of centrally located would be the center 3-4 bases, or in the center base (for an odd number of bases) or one or both of the center bases (for an even number of bases). More particularly, on a nucleic acid of at least 15 residues in length, there should be at least 7 residues flanking each side of the mismatch base, or on a nucleic acid of at least 16 residues in length, there should be at least 7 residues flanking two adjacent mismatched bases. Though any mismatch is useful, of particular interest are purine mismatches, such as introducing an adenosine base into the guide strand.

Another consideration is to avoid multiple changes in the "seed" sequence of the oligonucleotide or oligonucleotide analog, i.e., the first 8 bases. Thus, in a double-stranded RNA of at least 19 bases, there would be zero or one mismatch in 2-8 bases, and 1-5 mismatches in bases 9-14, or in bases 15 to the 3'-terminus. In other words, with respect to multiple mismatches, these can be either in the guide strand, or in both strands, and only one mismatch should occur in the seed region. In addition, to mismatches, it is contemplated that the guide strand may contain a base insertion with respect to the passenger strand.

The oligonucleotide or oligonucleotide analog may be double-stranded or single-stranded, including ds-RNAs and ss-siRNAs.

While ds-RNAs have been employed for some time, ss-RNAs are a new approach to gene silencing in which single-stranded RNA is chemically modified to enable it to be stable in vivo while retaining the ability to engage the RNAi machinery (Lima et al., 2012). The inventors have previously shown that anti-repeat ss-siRNAs can be active towards inhibiting expression of repeat containing genes in cell culture and the central nervous system of HD model mice. ss-siRNAs are attractive candidates for testing because, in contrast to duplex RNA, they are single-stranded and may possess better biodistribution and activity in vivo. Thus, the inventors contemplate the application of ss-siRNAs as CAG/CUG repeat targeting agents.

Another modification of oligonucleotides involved their conjugation to lipids, which are commonly used for modifying oligonucleotides. From a therapeutic point of view, lipid-oligonucleotide conjugates (LOCs) have emerged as an alternative to cationic particles in order to reduce toxicity and improve biodistribution. Oligonucleotide entry into cells normally takes place through receptor-mediated endocytosis by binding with high affinity to cell surface receptors. However, this uptake efficiency could change when modified oligonucleotides are internalized into the cell, but the use of biocleavable lipids can help mitigate any such effects if observed. Many synthetic strategies have been reported in recent years for obtaining oligonucleotides covalently linked to a variety of lipophilic moieties. The conjugation of these units can occur at either the nucleoside or the nucleotide level, giving rise to the corresponding amphiphilic-based compounds. Other strategies have incorporated lipid moieties through a phosphodiester bond in order to obtain LOC conjugates with better pharmacokinetic behaviors and improved cellular uptake. In general, the oligonucleotide ends (3'- and 5'-termini) are the most accessible conjugation sites for lipophilic units.

The use of lipid-containing formulations and lipid-based conjugates may increase uptake in the eye after administration of eye drops. Lipid conjugates or other types of conjugates may improve binding to particular cell types within the eye. Embodiments of our invention include such formulations and conjugates.

In the case of conjugates, a chemical moiety may be included on one end, on both ends, or on one or more central positions within an ASO or siRNA. In another embodiment, a chemical moiety can be conjugated to a complementary oligonucleotide that binds to the ASO rather than to the ASO itself (Nishina et al., 2015). If the oligonucleotide is a double-stranded RNA, the conjugate may be placed on either strand. In a preferred embodiment the conjugate is placed on the sense strand of double-stranded RNA.

Said chemical moiety may serve to improve cellular uptake or pharmacokinetic parameters, or may improve uptake by a particular cell type (Winkler, 2013). For example, this invention includes conjugates that show improved uptake in corneal endothelial cells. This in turn allows delivery to the cornea by administration of topical eyedrops, intracameral injection, or by intravitreal injection.

In one embodiment of the invention, the conjugated moiety is a lipid or other hydrophobic group. In other embodiments, the moiety comprises a peptide, carbohydrate or nucleic acid. Many moieties suitable for use in oligonucleotide conjugates are well known in the art (Winkler, 2013; Juliano, 2016). In some embodiments, the conjugated moiety may improve pharmacokinetics and uptake by increasing hydrophobicity. In other embodiments, the conjugated moiety may improve pharmacokinetics and uptake by interacting with specific proteins.

Conjugating a lipid group on one end of an oligonucleotide can lead to the assembly of micellar structures (Pendergraff et al., 2017). In some cases, these structures can be sufficient to trigger enhanced or optimal uptake. In other cases, the use of compounds containing multiple conjugate groups may be preferred, as this approach can be used to display groups in a way that increases binding to cells or proteins of interest, pharmacokinetic properties, and/or potency.

In some cases, the conjugated moiety can be attached to the oligonucleotide through a linkage designed to cleave inside cells, such as a reducible linkage, a nuclease-sensitive linkage, or a protease-sensitive linkage. In other embodiments, the conjugated moiety can be attached to the non-active strand of a duplex (such as the sense strand of a siRNA or a complementary RNA strand). In still other embodiments, the conjugate may be permanently attached to the active strand.

Table 1 shows a series of lipid conjugates based on tocopherol and cholesterol. A person of ordinary skill in the art will be able to envision other conjugate structures and designs.

TABLE 1

Illustrative lipid-conjugated ASOs, heteroduplex oligonucleotides and siRNAs suitable for targeting the expanded triplet repeat of TCF4.

| SEQ ID NO: | Sequence Code | Sequence | Mol. Wt. |
| --- | --- | --- | --- |
| SEQ ID NO: 59 | ASO_C1 | 5'-(Toc)AsGsCsGsCsGsCsGsCsGsCsGsCsGsCsGsCsGsCsGsCsA | 7025.0 |
| SEQ ID NO: 60 | ASO_C2 | 5'-(Toc)TTAsGsCsGsCsGsCsGsCsGsCsGsCsGsCsGsCsGsCsA | 7633.4 |
| SEQ ID NO: 61 | ASO_C3 | 5'-(Toc)TTAsGsCsGsCsGsCsGsCsGsCsGsCsGsCsGsCsATT(Toc) | 8940.7 |
| SEQ ID NOs 62 & 63 | HDO_C1 | 5'-AsGsCsGsCsGsCsGsCsGsCsGsCsGsCsA (SEQ ID NO: 62)<br>3'-(Toc)mUsmCsrGrUrCrGrUrCrGrUrCrGrUrCrGrUrCrGrUrCsmGsmU (SEQ ID NO: 63) | 6326.1<br>6802.8 |
| SEQ ID NOs: 64 & 65 | siRNA_C1 | 5'-rArGrCrArGrCrArGrCrArGrUrUrGrCrArGrCrArGrCrArGrCsmUsmU (SEQ ID NO: 64)<br>3'-(Chol)rUrCrGrUrCrGrUrCrGrUrCrArArCrGrUrCrGrUrCrGrUrCrG (SEQ ID NO: 65) | 6466.1<br>6324.4 |
| SEQ ID NOs: 66 & 67 | siRNA_C2 | 5'-mAsfsmCsmAmGmCmAmGmCmUmUmGmCmAsfGsmCsmAsmGsmCsmUsmU (SEQ ID NO: 66)<br>3'-(Chol)mUsmCsmGmUmCmGmUmCmAmAmCmGmUsmCsmG (SEQ ID NO: 67) | 6823.0<br>5642.5 |

Codes and modifications used:
Normal capital letters: deoxyribonucleotides;
rN: ribonucleotides
mN: 2'-O-methylribonucleotides;
fN: 2'-fluoro-2'-deoxyribonucleotides
Bold, underlined letters: locked nucleotides (LNA);
Toc: tocopheryl;
Chol: cholesteryl
PO linkages not explicitly shown;
PS linkages indicated as subscript "s"

Figure 8:
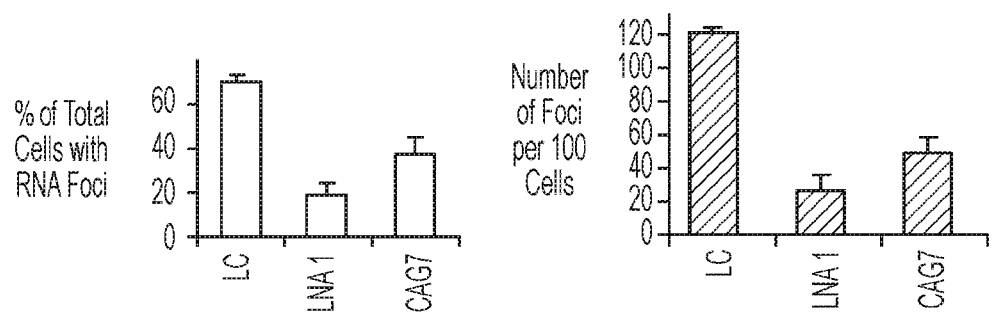
FIG. 8. Comparison of inhibition potency of CUG repeat-targeting antisense oligomers in F35T endothelial cell line. Effect on inhibition of CUG RNA foci by LNA 1, single-strand ASO CAG7 (21-mer 2-OMe modified ASO).

Single-stranded antisense oligonucleotides (ASOs) may bind directly to the CUG repeat. ASOs will not require the RNAi machinery and are a different strategy for silencing gene expression. The inventors contemplate ASOs substituted with locked nucleic acids (LNAs). LNA nucleotides are constrained by a bond between the 2' and 4' positions of the ribose ring (FIG. 8). This constraint "locks" the nucleotide into a position that is ideal for base-pairing and the introduction of a handful of LNA nucleotides into an ASO can tailor the affinity of an ASO for optimal success in many applications. Other modifications may be used to tailor ASO affinity for desired applications, including 2'-O-methoxyethyl RNA and tricycloDNA. A person of skill in the art will understand additional modifications that can be used to tailor ASO binding affinity and nucleobase stability. Thus, the inventors also contemplate the application of ASOs as CUG repeat containing targeting agents.

Commercially available equipment routinely used for the support-media-based synthesis of oligomeric compounds and related compounds is sold by several vendors including, for example, Biolytic (Fremont, Calif.), Bioautomation (Irving, Tex.), General Electric, as well as others. Suitable solid phase techniques, including automated synthesis techniques, are described in Scozzari and Capaldi, "Oligonucleotide Manufacturing and Analytic Processes for 2'-O-(2-methoxyethyl-Modified Oligonucleotides" in Crooke, S. T. (ed.) Antisense Drug Technology: Principles, Strategies, and Applications, Second Edition (2007).

Each of these technologies is described in greater detail below.

B. RNAi

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity. Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene. It is generally accepted that RNAi acts post-transcriptionally, targeting RNA transcripts for degradation. It appears that both nuclear and cytoplasmic RNA can be targeted.

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 20 to 23 nucleotides in length are most effective. This length reflects the lengths of digestion products resulting from the processing of much longer RNAs as described above. siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Several further modifications to siRNA sequences have been suggested in order to alter their stability or improve their effectiveness. It has been suggested that synthetic complementary 21-mer RNAs having di-nucleotide overhangs (i.e., 19 complementary nucleotides+3' non-complementary dimers) may provide the greatest level of suppression. These protocols may use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang. More recently, it has been suggested that it may be preferable for the overhangs to use 2'-OMe-uridine (2'-OMe-U). It may also be preferable to use a single 3' overhang in the antisense strand, and have no overhang in the sense strand.

Short hairpin RNA (shRNA) is a sequence of RNA that makes a tight hairpin turn that can be used to silence gene expression. shRNA is transcribed by RNA polymerase III. shRNA production in a mammalian cell can sometimes cause the cell to mount an interferon response as the cell seeks to defend itself from what it perceives as viral attack. Paddison et al. (2002) examined the importance of stem and loop length, sequence specificity, and presence of overhangs in determining shRNA activity. The authors found some interesting results. For example, they showed that the length of the stem and loop of functional shRNAs could vary. Stem lengths could range anywhere from 25 to 29 nt and loop size could range between 4 to 23 nt without affecting silencing activity. Presence of G-U mismatches between the 2 strands of the shRNA stem did not lead to a decrease in potency. Complementarity between the portion of the stem that binds to the target mRNA (antisense strand) and the mRNA, on the other hand, was shown to be critical. Single base mismatches between the antisense strand of the stem and the mRNA abolished silencing. It has been reported that presence of 2 nt 3'-overhangs is critical for siRNA activity. Presence of overhangs on shRNAs, however, did not seem to be important. Some of the functional shRNAs that were either chemically synthesized or in vitro transcribed, for example, did not have predicted 3' overhangs.

dsRNA can be synthesized using well-described methods. Briefly, sense and antisense RNA are synthesized from DNA templates using T7 polymerase (MEGAscript, Ambion). After the synthesis is complete, the DNA template is digested with DNaseI and RNA purified by phenol/chloroform extraction and isopropanol precipitation. RNA size, purity and integrity are assayed on denaturing agarose gels. Sense and antisense RNA are diluted in potassium citrate buffer and annealed at 80° C. for 3 min to form dsRNA. As with the construction of DNA template libraries, a procedures may be used to aid this time intensive procedure. The sum of the individual dsRNA species is designated as a "dsRNA library."

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA.

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

Several groups have developed expression vectors that continually express siRNAs in stably transfected mammalian cells. Some of these plasmids are engineered to express shRNAs lacking poly (A) tails. Transcription of shRNAs is initiated at a polymerase III (pol III) promoter and is believed to be terminated at position 2 of a 4-5-thymine transcription termination site. shRNAs are thought to fold into a stem-loop structure with 3' UU-overhangs. Subsequently, the ends of these shRNAs are processed, converting the shRNAs into ~21 nt siRNA-like molecules. The siRNA-like molecules can, in turn, bring about gene-specific silencing in the transfected mammalian cells.

More generally, most any oligo- or polynucleotide may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described in U.S. Pat. No. 5,705,629, each incorporated herein by reference. In the methods of the present disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

C. Antisense

In some embodiments, the nucleic acid comprises one or more antisense segments which inhibit(s) expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) or uracil (A:U). Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

D. CRISPR

1. CRISPR and Nucleases

CRISPR regions (clustered regularly interspaced short palindromic repeats) are DNA loci containing short repetitions of base sequences. Each repetition is followed by short segments of "spacer DNA" from previous exposures to a virus. CRISPR regions are found in approximately 40% of sequenced eubacteria genomes and 90% of sequenced archaea. CRISPR regions are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and silence these exogenous genetic elements like RNAi in eukaryotic organisms.

Repeats were first described in 1987 for the bacterium *Escherichia coli*. In 2000, similar clustered repeats were identified in additional bacteria and archaea and were termed Short Regularly Spaced Repeats (SRSR). SRSR were renamed CRISPR in 2002. A set of genes, some encoding putative nuclease or helicase proteins, were found to be associated with CRISPR repeats (the Cas, or CRISPR-associated genes).

In 2005, three independent researchers showed that CRISPR spacers showed homology to several phage DNA and extrachromosomal DNA such as plasmids. This was an indication that the CRISPR/Cas system could have a role in adaptive immunity in bacteria. Koonin and colleagues proposed that spacers serve as a template for RNA molecules, analogously to eukaryotic cells that use a system called RNA interference.

In 2007, Barrangou & Horvath (food industry scientists at Danisco) and others showed that they could alter the resistance of *Streptococcus thermophilus* to phage attack with spacer DNA. Doudna and Charpentier had independently been exploring CRISPR-associated proteins to learn how bacteria deploy spacers in their immune defenses. They jointly studied a simpler CRISPR system that relies on a protein called Cas9. They found that bacteria respond to an invading phage by transcribing spacers and palindromic DNA into a long RNA molecule that the cell then uses tracrRNA and Cas9 to cut it into pieces called crRNAs.

CRISPR was first shown to work as a genome engineering/editing tool in human cell culture by 2012. It has since been used in a wide range of organisms including baker's yeast (*S. cerevisiae*), zebrafish, nematodes (*C. elegans*), plants, mice, and several other organisms. Additionally CRISPR has been modified to make programmable transcription factors that allow scientists to target and activate or silence specific genes. Libraries of tens of thousands of guide RNAs are now available.

The first evidence that CRISPR can reverse disease symptoms in living animals was demonstrated in March 2014, when MIT researchers cured mice of a rare liver disorder. Since 2012, the CRISPR/Cas system has been used for gene editing (silencing, enhancing or changing specific genes) that even works in eukaryotes like mice and primates. By inserting a plasmid containing Cas genes and specifically designed CRISPR guide sequences, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (Cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (*E coli*, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (~30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype *E coli*) proteins (called CasA-E in *E. coli*) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in *E. coli* requires Cascade and Cas3, but not Cas1 and Cas2. The Cmr (Cas RAMP module) proteins found in *Pyrococcus furiosus* and other prokaryotes form a functional complex with small CRISPR RNAs that recognizes and cleaves complementary target RNAs. RNA-guided CRISPR enzymes are classified as type V restriction enzymes.

Cas9 is a nuclease, an enzyme specialized for cutting DNA, with two active cutting sites, one for each strand of the double helix. The team demonstrated that they could disable one or both sites while preserving Cas9's ability to home located its target DNA. Jinek et al. (2012) combined tracrRNA and spacer RNA into a "single-guide RNA" molecule that, mixed with Cas9, could find and cut the correct DNA targets. Jinek et al. (2012) proposed that such synthetic guide RNAs might be able to be used for gene editing.

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of *Francisella novicida* uses a unique, small, CRISPR/Cas-associated RNA (scaRNA) to repress an endogenous transcript encoding a bacterial lipoprotein that is critical for *F. novicida* to dampen host response and promote virulence. Wang et al. (2013) showed that coinjection of Cas9 mRNA and sgRNAs into the germline (zygotes) generated mice with mutations. Delivery of Cas9 DNA sequences also is contemplated.

See also U.S. Patent Publication 2014/0068797, which is incorporated by reference in its entirety.

Clustered Regularly Interspaced Short Palindromic Repeats from *Prevotella* and *Francisella* 1 or CRISPR/Cpf1 is a DNA-editing technology analogous to the CRISPR/Cas9 system. Cpf1, now named Cas12a according to systemic nomenclature, is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

CRISPR/Cpf1 was found by searching a published database of bacterial genetic sequences for promising bits of DNA. Its identification through bioinformatics as a CRISPR system protein, its naming, and a hidden Markov model (HMM) for its detection were provided in 2012 in a release of the TIGRFAMs database of protein families. Cpf1 appears in many bacterial species. The ultimate Cpf1 endonuclease that was developed into a tool for genome editing was taken from one of the first 16 species known to harbor it. Two candidate enzymes from *Acidaminococcus* and *Lachnospiraceae* display efficient genome-editing activity in human cells.

Alternative CRISPR nucleases are routinely being discovered and developed for use. For example, additional Cas9 proteins with promising properties for therapeutic use include those from *Geobacillus, N meningitides, C. jejuni*, and *S. aureus*. Additional evolved or derived versions with properties such as enhanced specificity and altered PAM motifs include Cas9-HF, eCas9, HypaSpCas9 and xCas9.

The CRISPR/Cas systems are separated into three classes. Class 1 uses several Cas proteins together with the CRISPR RNAs (crRNA) to build a functional endonuclease. Class 2 CRISPR systems use a single Cas protein with a crRNA. Cpf1 has been recently identified as a Class 2, Type V CRISPR/Cas systems containing a 1,300 amino acid protein.

The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alpha-helical recognition lobe of Cas9.

Cpf1 CRISPR-Cas domain architecture shows that Cpf1 is functionally unique, being classified as Class 2, type V CRISPR system. The Cpf1 loci encode Cas1, Cas2 and Cas4 proteins more similar to types I and III than from type II systems. Database searches suggest the abundance of Cpf1-family proteins in many bacterial species.

Functional Cpf1 doesn't use a tracrRNA; only a single ~42-nt guide (crRNA) is required. This benefits genome editing because Cpf1 is not only smaller than Cas9, but also it has a smaller sgRNA molecule (approximately half as many nucleotides as Cas9).

The Cpf1-crRNA complex cleaves target DNA or RNA by identification of a protospacer adjacent motif 5'-YTN-3' (where "Y" is a pyrimidine and "N" is any nucleobase) or 5'-TTN-3', in contrast to the G-rich PAM targeted by Cas9. After identification of PAM, Cpf1 introduces a sticky-end-like DNA double-stranded break of 4 or 5 nucleotides overhang.

The CRISPR/Cpf1 system consist of a Cpf1 enzyme and a guide RNA that finds and positions the complex at the correct spot on the double helix to cleave target DNA. CRISPR/Cpf1 systems activity has three stages:

Adaptation, during which Cas1 and Cas2 proteins facilitate the adaptation of small fragments of DNA into the CRISPR array;

Formation of crRNAs: processing of pre-cr-RNAs producing of mature crRNAs to guide the Cas protein; and Interference, in which the Cpf1 is bound to a crRNA to form a binary complex to identify and cleave a target DNA sequence.

A recent study has demonstrated the feasibility of the CRISPER/Cas9 technology to excise the CTG triplet repeat expansion in the DMPK gene responsible for myotonic dystrophy type 1 by inducing a pair of double stranded breaks flanking the triplet repeat expansion followed by DNA repair (van Angtmaal et al., 2017). However, simultaneous induction of a pair of breaks flanking the CTG repeat expansion followed by DNA repair in the absence of the repeat was not realized with adequate efficiency in that study.

A nuclear localization signal-tagged nuclease-deficient Cas9-GFP fusion (dCas9-GFP) with appropriate sgRNAs can target and track mRNAs in live cells (Nelles et al., 2016). This RNA-targeting Cas9 system has been modified to efficiently degrade expanded repeat RNA in the repeat expansion disorders of mytonic dystrophy 1, myotonic dystrophy 2, C9orf72-linked amyotrophic lateral sclerosis, and polyglutamine disorders (Batra et al., 2017).

2. sgRNA

As an RNA guided protein, Cas9 requires a single guide RNA (sgRNA) to direct the recognition of DNA targets (Mali et al., 2013a). CRISPR sequences in bacteria are expressed in multiple RNAs and then processed to create guide strands for RNA (Bikard et al., 2013). Because eukaryotic systems lack some of the proteins required to process CRISPR RNAs the synthetic construct sgRNA was created to combine the essential pieces of RNA for Cas9 targeting into a single RNA expressed with the RNA polymerase type III promoter U6 (Mali et al., 2013b,c). Synthetic sgRNAs are typically just over 100 bp and contain a portion which targets the 20 nucleotides immediately preceding the PAM sequence (NGG for *S. pyogenes* Cas9); sgRNAs do not contain a PAM sequence.

E. Nucleic Acid Delivery and Expression

As discussed above, in certain embodiments, expression cassettes are employed to express a gene product, either for subsequent purification and delivery to a cell/subject, or for use directly in a genetic-based delivery approach. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

1. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

2. 2A Protease

The 2A-like self-cleaving domain from the insect virus *Thosea asigna* (TaV 2A peptide) (Chang et al., 2009) has been shown to function across eukaryotes and cause cleavage of amino acids to occur co-translationally within the 2A-like peptide domain. Therefore, inclusion of TaV 2A peptide allows the expression of multiple proteins from a single mRNA transcript. Importantly, the domain of TaV when tested in eukaryotic systems have shown greater than 99% cleavage activity (Donnelly et al., 2001).

3. Delivery of Expression Vectors

There are a number of ways in which expression vectors may introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells. The first viruses used as gene vectors were DNA viruses including the papovaviruses (simian virus 40, bovine papilloma virus, and polyoma) and adenoviruses. These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals.

One set of methods for in vivo delivery involves the use of an adenovirus, or adeno-associated virus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5□-tripartite leader (TPL) sequence which makes them preferred mRNA's for translation.

In one system, recombinant adenovirus is generated from homologous recombination between shuttle vector and pro-virus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

In one format for methods for culturing 293 cells and propagating adenovirus, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/1) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the disclosure. The adenovirus may be of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the disclosure. The polynucleotide encoding the gene of interest may also be inserted in lieu of the deleted E3 region in E3 replacement vectors, or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential as in vivo gene transfer vectors.

Adenovirus vectors have been used in eukaryotic gene expression and vaccine development. Animal studies suggested that recombinant adenovirus could be used for gene therapy. Studies in administering recombinant adenovirus to different tissues include trachea instillation, muscle injection, peripheral intravenous injections and stereotactic inoculation into the brain.

Adeno-associated virus (AAV) is a replication-deficient parvovirus, the single-stranded DNA genome of which is about 4.7 kb in length including 145 nucleotide inverted terminal repeat (ITRs). When AAV infects a host cell, the viral genome integrates into the host's chromosome resulting in latent infection of the cell. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating.

AAV vectors may be derived from an adeno-associated virus serotype, including without limitation, AAV-1, AAV-2, AAV-3, AAV-4, AAV-5, AAVX7, etc., and various AAV serotypes have different tissue specificities. AAV vectors can have one or more of the AAV wild-type genes deleted in whole or part, preferably the rep and/or cap genes (described below), but retain functional flanking ITR sequences (also described below). Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. AAV vectors may be altered to make them replication-defective, but still comprised of an AAV protein shell encapsidating a DNA molecule of interest. This DNA molecule may be flanked on both sides by an ITR sequence. These AAV vectors may then be propagated in a suitable host cell which has had the AAV helper functions and accessory functions introduced. These AAV vectors are suitable for the introduction of foreign DNA into a human cell.

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin. Using antibodies against major histocompatibility complex class I and class II antigens, they demonstrated the infection of a variety of human cells that bore those surface antigens with an ecotropic virus in vitro.

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes. Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination.

Other viral vectors may be employed as expression constructs in the present disclosure. Vectors derived from viruses such as vaccinia virus or herpesviruses may be employed. They offer several attractive features for various mammalian cells.

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present disclosure. These include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection. Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Polyomavirus DNA has been injected in the form of calcium phosphate precipitates into liver and spleen of adult and newborn mice demonstrating active viral replication and acute infection. Direct intraperitoneal injection of calcium phosphate-precipitated plasmids also results in expression of the transfected genes. It is envisioned that DNA encoding a gene of interest may also be transferred in a similar manner in vivo and express the gene product.

In still another embodiment of the disclosure for transferring a naked DNA expression construct into cells may involve particle bombardment. This method depends on the ability to accelerate DNA-coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

Selected organs including the liver, skin, and muscle tissue of rats and mice have been bombarded in vivo. This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are lipofectamine-DNA complexes.

Liposome-mediated nucleic acid delivery and expression of foreign DNA in vitro has been very successful. The feasibility of liposome-mediated delivery and expression of foreign DNA in cultured chick embryo, HeLa and hepatoma cells has been demonstrated, and successful liposome-mediated gene transfer in rats after intravenous injection has been achieved. A reagent known as Lipofectamine 2000™ is widely used and commercially available.

In certain embodiments of the disclosure, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin. A synthetic neoglycoprotein, which recognizes the same receptor as ASOR, has been used as a gene delivery vehicle and epidermal growth factor (EGF) has also been used to deliver genes to squamous carcinoma cells.

IV. MODIFIED NUCLEOTIDES

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In particular embodiments, nucleic acids may be modified with a 5'-vinylphosphonate to increase the stability of the nucleic acid and improve tissue accumulation. In certain embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(Rm)-alkyl; O, S, or N(Rm)-alkenyl; O, S or N(Rm)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(Rm)(Rn) or O—CH$_2$—C(=O)—N(Rm)(Rn), where each Rm and Rn is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, $O(CH_2)_2$—O—$N(CH_3)_2$, —$O(CH_2)_2O(CH_2)_2N(CH_3)_2$, and O—$CH_2$—C(=O)—$N(H)CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—C($R_aR_b$)—N(R)—O— or, —C($R_aR_b$)—O—N(R)—; 4'-$CH_2$-2', 4'-($CH_2$)$_2$-2', 4'-($CH_2$)—O-2' (LNA); 4'-($CH_2$)—S-2; 4'-($CH_2$)$_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya et al., J. Org. Chem., 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=$NR_a$)—, —C(=O)—, —C(=S)—, —Si($R_a$)$_2$—, —S(=O)$_x$—, and —N($R_a$)—; wherein:
x is 0, 1, or 2;
n is 1, 2, 3, or 4;
each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-Cao aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and
each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-($CH_2$)$_3$-2') BNA, and (K) Methoxy(ethyleneoxy) (4'-CH($CH_2OMe$)-O-2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., Nucleic Acids Research, 2003, 21, 6365-6372).

In certain embodiments, substituted sugar moieties comprise one or more non-bridging sugar substituent and one or more bridging sugar substituent (e.g., 5'-substituted and 4'-2' bridged sugars; PCT International Application WO 2007/134181, published on Nov. 22, 2007, wherein LNA is substituted with, for example, a 5'-methyl or a 5'-vinyl group). For example, in certain embodiments, the nucleosides may contain two bridging substitutents, forming a tricyclic structure as found in tricycloDNA (Steffens and Leurmann, 1997). In other embodiments, a constrained structure may also include the phosphorus atom of the internucleotide linkage (Dupouy et al., 2006).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Publication No. 20050130923, published on Jun. 16, 2005) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), altritol nucleic acid (ANA), mannitol nucleic acid (MNA) (see Leumann, C J. Bioorg. & Med. Chem. (2002) 10:841-854), and fluoro HNA (F-HNA).

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO2008/101157 Published on Aug. 21, 2008 for other disclosed 5',2'-bis substituted nucleosides) and replacement of the ribosyl ring oxygen atom with S and further substitution at the 2'-position (see U.S. Patent Publication US20050130923, published on Jun. 16, 2005) or alternatively 5'-substitution of a bicyclic nucleic acid (see PCT International Application WO2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2(3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States Patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, each of which is herein incorporated by reference in its entirety.

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, methylenephosphonates, vinylphosphonates, phosphonoacetates, thiophosphonoacetates, phosphoramidates, and phosphorothioates (P=S). Representative non-phosphorus containing internucleoside linking groups include, but are not limited to, amide, triazole, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids. etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), other amides, formacetyl (3'-O—CH$_2$—O-5'), and thioformacetal (3'-S—CH$_2$—O-5'), and triazole linkages. Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

V. PHARMACEUTICAL FORMULATIONS

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423, incorporated by reference herein. Compositions of the present disclosure comprise an effective amount of the oligonucleotide to cells, dissolved or dispersed in a pharmaceutically acceptable carrier or medium.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Ocular administration includes topical eye drops, intracameral injection, or intravitreal injection to target the cornea including corneal endothelial cell layer. Alternatively, administration may be oral, nasal, buccal, or topical. Alternatively, administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present disclosure may be incorporated with excipients. The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present disclosure is the use of lipid delivery vehicles. Lipid vehicles encompass micelles, microemulsions, macroemulsions, liposomes, and similar carriers. The term micelle refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 µm.

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly (ethylene glycol)$_{2000}$) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio.

Exemplary amounts of lipid constituents used for the production of the liposome include, for instance, 0.3 to 1 mol or 0.4 to 0.6 mol of cholesterol; 0.01 to 0.2 mol or 0.02 to 0.1 mol of phosphatidylethanolamine; 0.0 to 0.4 mol or 0-0.15 mol of phosphatidic acid per 1 mol of phosphatidylcholine.

Liposomes can be constructed by well-known techniques. Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes.

The liposomes can also be formed by extrusion through an asymmetric ceramic filter, such as a Ceraflow Microfilter (commercially available from the Norton Company, Worcester, Mass.).

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present disclosure, liposomes have a size of about 0.05 microns to about 0.5 microns, or having a size of about 0.05 to about 0.2 microns.

VI. DETECTION METHODS

In one aspect, the disclosure provides method for detection of nuclear RNA foci, and the diagnosis of FECD based on the presence of such foci. A variety of different methodologies are available for the detection of foci. In general, one can detect either the expanded repeat RNAs that the inventors have identified in the cornea of patients with FECD. Alternatively, one could detect the proteins associated with the foci.

A. Fluorescence In Situ Hybridization

FISH (fluorescent in situ hybridization) is a cytogenetic technique developed to detect and localize the presence or absence of specific nucleic acid sequences. FISH uses fluorescent probes that bind to targets (e.g., parts of the chromosome with which they show a high degree of sequence complementarity). Fluorescence microscopy can be used to find out where the fluorescent probe is bound. FISH is often used for finding specific features in DNA for use in genetic counseling, medicine, and species identification, but can also be used to detect and localize specific RNA targets (mRNA, lncRNA and miRNA) in cells and tissue samples. In this context, it can help define the spatial-temporal patterns of gene expression within cells and tissues.

FISH is a very general technique. The differences between the various FISH techniques are usually due to variations in the sequence and labeling of the probes; and how they are used in combination. Probes are divided into two generic categories: cellular and acellular. "In situ" in fluorescent in situ hybridization refers to the placement of the probe placed cellularly. These few modifications make possible all FISH techniques.

Probe size is important because longer probes hybridize less specifically than shorter probes. A short strand of DNA or RNA (often 10-25 nucleotides) which is complementary to a given target sequence, it can be used to identify or locate the target. The overlap defines the resolution of detectable features. A variety of other techniques use mixtures of differently colored probes. A range of colors in mixtures of fluorescent dyes can be detected, so that different targets can be identified by a characteristic color and a variety of ratios of colors.

B. Chromogenic In Situ Hybridzation

Chromogenic in situ hybridzation (CISH) enables the gain genetic information in the context of tissue morphology using methods already present in histology labs. CISH allows detection of gene amplification, chromosome translocations and chromosome number using conventional enzymatic reactions under the brightfield microscope on formalin-fixed, paraffin-embedded (FFPE) tissues. U.S. Patent Publication No. 2009/0137412, incorporated herein by reference. The scanning may be performed, for example, on an automated scanner with Fluorescence capabilities (Bioview System, Rehovot, Israel).

C. Immunodetection

In further embodiments, there are immunodetection methods for identifying and/or quantifying FECD foci. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes. It is also possible to perform in vivo assays.

Contacting the chosen biological sample with an antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to foci-related proteins. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241, incorporated by reference herein. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the nuclear foci is added to the wells. After binding and washing to remove non-specifically bound immune complexes, the bound antigen may be detected. Detection may be achieved by the addition of another anti-foci antibody that is linked to a detectable label. This type of ELISA is a simple "sandwich ELISA." Detection may also be achieved by the addition of a second anti-foci antibody, followed by the addition of a third antibody that has binding affinity for the second antibody, with the third antibody being linked to a detectable label.

In another exemplary ELISA, the samples suspected of containing the foci are immobilized onto the well surface and then contacted with anti-foci antibody. After binding and washing to remove non-specifically bound immune complexes, the bound anti-foci antibodies are detected. Where the initial anti-foci antibodies are linked to a detectable label, the immune complexes may be detected directly. Again, the immune complexes may be detected using a second antibody that has binding affinity for the first anti-foci antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the protein and membrane. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

Antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

VII. METHODS OF TREATMENT

A. Therapy

In accordance with the present disclosure, the inventors propose to use oligonucleotides to target nuclear RNA foci in a manner analogous to the work of others working on tri-nucleotide repeat diseases. Some of this work is summarized in the table below.

TABLE 2

Publications on allele-selective inhibition of trinucleotide repeat gene expression

| Publication | Disease gene targeted | Chemistry used |
| --- | --- | --- |
| Hu, 2009 | HTT | PNA, LNA |
| Hu, 2010 | HTT | Duplex RNA |
| Gagnon, 2010 | HTT | LNA, CeNA, other single-stranded oligos |
| Gagnon, 2011 | HTT | Oligonucleotide-spermine conjugates |
| Hu, 2012 | HTT | Duplex RNA |
| Yu, 2012 | HTT | ss-siRNA |
| Liu, 2013 | HTT, ATXN-3 | Chemically modified dsRNA, abasic RNA |

TABLE 2-continued

Publications on allele-selective inhibition
of trinucleotide repeat gene expression

| Publication | Disease gene targeted | Chemistry used |
|---|---|---|
| Liu, 2013 | ATXN-3 | ss-siRNA |
| Aiba, 2013 | HTT, ATXN-3 | UNA |
| Hu, 2014 | HTT | ss-siRNA |
| Hu, 2014 | ATN-1 | dsRNA, Chem. Mod. dsRNA ss-siRNA, abasic RNA, UNA |

The following disclosure provides further information regarding the implementation of an oligonucleotide-based therapeutic approach for targeting RNA foci in subjects with FECD.

B. Delivering Oligonucleotides

In certain embodiments, oligonucleotide compounds and compositions are delivered to the eye of a subject. In certain embodiments, oligonucleotide compounds and compositions are delivered to a subject directly to the eye, such as to target corneal endothelium.

In certain embodiments, delivery of an oligonucleotide compound or composition described herein can affect the pharmacokinetic profile of the oligonucleotide compound or composition. In certain embodiments, delivery of an oligonucleotide compound or composition results in 47% down-regulation of a target mutant expanded repeat RNA, mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a mutant expanded repeat RNA, target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days.

In certain embodiments, an oligonucleotide is delivered once every week, every two weeks, every month, every two months, every 90 days, every 3 months, every 6 months, twice a year or once a year.

VIII. COMBINATION THERAPIES

It is common in many fields of medicine to treat a disease with multiple therapeutic modalities, often called "combination therapies." In the present application, the inventors contemplate using combination therapies to treat FECD. Such combinations will include the oligonucleotides according to the present disclosure, along with one or more "standard" therapeutic modalities.

Thus, to treat FECD, one may contact a target cell in subject with an oligonucleotide and at least one other therapy. These therapies would be provided in a combined amount effective to achieve a reduction in one or more disease parameter. This process may involve contacting the subjects with the both agents/therapies at the same time, e.g., using a single composition or pharmacological formulation that includes both agents, or by contacting the cell/subject with two distinct compositions or formulations, at the same time, wherein one composition includes the oligonucleotide and the other includes the other agent.

Alternatively, the oligonucleotide may precede or follow the other treatment by intervals ranging from minutes to weeks. One would generally ensure that a significant period of time did not expire between each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the oligonucleotide or the other therapy will be desired. Various combinations may be employed, where the oligonucleotide is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. As discussed above, topical hypertonic saline, heat dehydration, and corneal transplantation have been used to treat FECD and can be used in combination with the oligonucleotide therapies described herein.

IX. KITS

Any of the compositions described herein may be comprised in a kit. In a non-limiting example, an oligonucleotide targeting a tri-nucleobase repeat is included in a kit. The kit may further include a sterile buffer to facilitate dilution. The oligonucleotide may be labeled, such as with a fluorescent label. The oligonucleotide may be formulated for delivery to a subject, such as for ocular administration.

In still further embodiments, there kits may be for use with immunodetection methods described above. The kits will thus comprise, in suitable container means, a first antibody that binds to nuclear foci, and optionally an immunodetection reagent. The antibody may be pre-bound to a solid support, such as a column matrix and/or well of a microtitre plate. The antibodies may have detectable labels that are associated with or linked to the given antibody. Detectable labels that are associated with or attached to a secondary binding ligand are also contemplated. Exemplary secondary ligands are those secondary antibodies that have binding affinity for the first antibody.

The kits may further comprise a suitably aliquoted composition of a foci-related antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the oligonucleotides, antibodies and any other reagent containers in close confinement for commercial sale. Such containers may include injection or blow-molded plastic containers into which the desired vials are retained. Instructions may include variations that can be implemented.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

X. EXAMPLES

The following examples are included to demonstrate certain non-limiting aspects of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1—Materials & Methods

Subjects. The study was approved by the institutional review board of the University of Texas Southwestern Medical Center and conducted in adherence with the tenets of the Declaration of Helsinki.

After informed consent, the subjects underwent a complete eye examination including slit lamp biomicroscopy by a cornea fellowship-trained ophthalmologist. Subjects underwent endothelial keratoplasty for FECD severity Krachmer grade 5 (≥5 mm central confluent guttae without stromal edema) or 6 (≥5 mm central confluent guttae with stromal edema) assessed by slit lamp microscopy (Krachmer et al., 1978). Surgically explanted endothelium-Descemet's membrane monolayers were fixed in a 4% phosphate-buffered formaldehyde, equilibrated in a 30% sucrose solution for cytoprotection, and frozen in Tissue-Tek Optimal Cutting Tissue (OCT) compound (Sakura, Torrance, Calif.) for fluorescence in situ hybridization (FISH) studies (Mootha et al., 2015). Genomic DNA was extracted from peripheral blood leukocytes of each study subject using Autogen Flexigene (Qiagen, Valencia, Calif.).

Corneal endothelial samples from post-mortem donor corneas preserved in Optisol GS corneal storage media (Bausch & Lomb, Rochester, N.Y.) were obtained from the eye bank of Transplant Services at UT Southwestern. Certified eye bank technicians screened the donor corneal endothelium with slit lamp biomicroscopy and Cellchek EB-10 specular microscopy (Konan Medical). Donor corneal tissue with FECD was identified by the presence of confluent central guttae. Endothelium-Descemet's membrane monolayers from donor corneas were micro-dissected and stored as previously described (Mootha et al., 2015). DNA from the remaining corneal tissue of each sample was extracted with TRIzol reagent (ThermoScientific).

TCF4 CTG18.1 polymorphism genotyping. Genomic DNA from subjects' peripheral leukocytes or corneal tissue was used for genotyping. The CTG18.1 trinucleotide repeat polymorphism in the TCF4 gene was genotyped using a combination of short tandem repeat (STR) and triplet repeat primed polymerase chain reaction (TP-PCR) assays as the inventors have previously described (Mootha et al/. 2014). For the STR assay, a pair of primers flanking the CTG18.1 locus was utilized for PCR amplification with one primer labeled with FAM on 5' end. The TP-PCR assay was performed using the 5' FAM labeled primer specific for the repeat locus paired with repeat sequence targeted primers for PCR amplification. PCR amplicons were loaded on an ABI 3730XL DNA analyzer (Applied Biosystems, Foster City, Calif., USA) and the results analyzed with ABI GeneMapper 4.0 (Applied Biosystems). Large triplet repeat expansions were sized by Southern blot analysis using digoxigenin labeled probes.[8]

Detection of TCF4 repeat antisense transcript. TCF4 expression was analyzed by quantitative PCR on a 7500 real-time PCR system (Applied Biosystems) using iTaq SYBR Green Supermix (Bio-rad). Data was normalized relative to levels of HPRT1 mRNA. Primers specific for TCF4 exon18 are as follows: F 5'-TGACGAT-GAGGACCTGACAC-3 (SEQ ID NO: 5)'; R 5"-GTCTGGGGCTTGTCACTCTT-3' (SEQ ID NO: 6). Primers for TCF4 intron2: F 5'-GAGAGAGGGAGT-GAAAGAGAGA-3' (SEQ ID NO: 7); R 5'-GGCAATGTC-CATTTCCATCT-3' (SEQ ID NO: 8).

To detect antisense transcript, cDNA was generated from 0.25 μg of total RNA using the SuperScript III system (Invitrogen) with strand specific reverse primers attaching a linker sequence LK. Next, cDNA was amplified by PCR with strand-specific forward and LK primers (FIG. 5B). The PCR products were cloned and Sanger sequenced to verify their specificity.

Human corneal endothelial cell culture. The "Zante" human corneal endothelial cell line derived from a healthy control subject expressing TCF4 transcript with approximately 16-19 CUG repeats was a generous gift of Dr. Danielle Robertson (UT Southwestern) (Sheerin et al., 2012). The F35T corneal endothelial cell line derived from FECD patient expressing TCF4 transcript with approximately 1500 CUG repeats was a generous gift of Dr. Albert Jun (Johns Hopkins). The F45 corneal endothelial cell line derived from FECD patient expressing TCF4 transcript with approximately 71 CUG repeats was a primary culture from a donor cornea obtained from Transplant Services at UT Southwestern. The dissected Descemet's membrane monolayer was incubated with 2 mg/ml collagenase A (Roche) in culture media at 37° C. for 4 hours to dissociate the cells, spun down at 800 g for 5 minutes, and plated on culture dish pre-coated with fibronectin (FNC) (Athena Environmental Sciences). Cells were grown in modified Eagle's minimal essential media (OptiMEM) (ThermoFisher) supplemented with 8% fetal bovine serum, 5 ng/mL human epidermal growth factor (ThermoFisher), 20 ng/mL nerve growth factor (Fisher Scientific), 100 μg/mL bovine pituitary extract (ThermoFisher), 20 μg/mL ascorbic acid (Sigma-Aldrich), 200 mg/L calcium chloride (Sigma-Aldrich), 0.08% chondroitin sulfate (Sigma-Aldrich), 50 μg/mL gentamicin (ThermoFisher), and antibiotic/antimycotic solution (diluted 1/100) (Sigma-Aldrich) (Toyono et al., 2016). Cultures were incubated at 37° C. in 5% $CO_2$ and passed when confluent.

Transcript copy number measurement by qPCR. Transcript copy number measurement was performed essentially as described (Liu et al., 2017). Briefly, standard RNA was made by in vitro transcription with corresponding purified PCR fragment containing SP6 promoter sequence. After checking the quality of the RNA with a Bioanalyzer® (Agilent), a serial dilution of purified standard RNA, ranging from 10 to $10^5$ copies was used to construct standard curve for qPCR efficiency by qPCR following reverse transcription. The qPCR was performed on a CFX Connect Real-Time System (Bio-Rad). Cq values in each dilution were measured in triplicate. To determine transcript copy number per cell, total RNA of cells was extracted and certain amount of RNA was used to do reverse transcription. For each transcript, a serial dilution of cDNA was used. Cq value in each dilution were measured in triplicate. Copy number per cell was calculated by using the standard curve for qPCR efficiency of each transcript. Data were analyzed from two experiments. Results are showed as the mean±SD. Primers used to make PCR product are: GAPDH E1F1 SP6 (5'-ATTTAGGTGACAC-TATAGAACTCTGCTCCTCCTGTTCGAC-3' (SEQ ID NO: 9)), GAPDH E5R1 (5'-TTGATTTTGGAGG-GATCTCG-3' (SEQ ID NO: 10)), TCF4 E2F1 SP6 (5'-ATTTAGGTGACACTATAGAATGCTAAAATGCAT-CACCAACA-3' (SEQ ID NO: 11)), TCF4 E3R1 (5'-GAGCCAGTAAAATGTCCACTTG-3' (SEQ ID NO: 12)), TCF4 intron2dwF1 SP6 (5'-ATTTAGGTGACAC-TATAGAATGTTGCACTTTCTCCATTCG-3' (SEQ ID NO: 13)), TCF4 intron2dwR1 (5'-CAGGAGAGCAATTT-GAAGCA-3' (SEQ ID NO: 14)), TCF4 E18F1 SP6 (5'-ATTTAGGTGACACTATAGAATGACGAT-GAGGACCTGACAC-3' (SEQ ID NO: 15)), TCF4 E18R1 (5'-AGGATCAGGAGCTTGGTCTG-3' (SEQ ID NO: 16)). Primers and probes used for qPCR are: Human GAPDH (GAPDH) Endogenous Control (Thermo Fisher 4310884E), TCF4 E2F2 (5'-TAGGGACGGACAAAGAGCTG-3' (SEQ ID NO: 17)), TCF4 E3R2 (5'-CCACTTGC-CAAAGAAGTTGG-3' (SEQ ID NO: 18)), TCF4 E2/3 probe (5'-TTCACCTCCTGTGAGCAGTG-3' (SEQ ID NO: 19)), TCF4 intron2dwF2 (5'-TTCTCCAT-TCGTTCCTTTGC-3' (SEQ ID NO: 20)), TCF4 intron2dwR2 (5'-CACTCCCTCTCTCTCCAGCA-3' (SEQ ID NO: 21)), TCF4 intron2dw probe (5'-GCTCTGACTCAGGGAAGGTG-3' (SEQ ID NO: 22)), TCF4 E18F2 (5'-ACGATGAGGACCTGACACCA-3' (SEQ ID NO: 23)), TCF4 E18R2 (5'-GGGCTTGTCACTCTT-GAGGT-3' (SEQ ID NO: 24)), TCF4 E18 probe (5'-AGAAGGCAGAGCGTGAGAAG-3' (SEQ ID NO: 25))

Figure 3A:
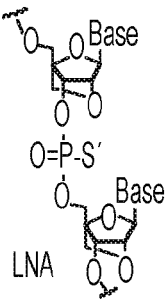
FIGS. 3A-D. Inhibition of CUG"P foci by LNA-ASOs in F35T (CUG 22/1500) and F45 (CUG 16/71) endothelial cell lines.

Synthesis and transfection of oligonucleotides. LNA phosphoramidites were synthesized from the 3'-hydroxyl precursors (Rasayan) and assembled into oligonucleotides as previously described (Pendergraff et al., 2017). ASOs were deprotected using concentrated aqueous ammonia for 16 h at 55° C. and were characterized by LCMS (FIG. 3A). LNA ASOs were transfected into cells with Lipofectamine RNAiMAX (Life Technologies) as previously described (Hu et al., 2009). Cells were plated at a density of 300,000 per well of a 6-well plate and transfected at the same time using an oligonucleotide concentration of 25 µM. After 72 hours, the cells were transfected again as mentioned above and harvested 4 days later to assess the effects for reduction of $CUG^{exp}$ foci using RNA FISH/immunofluorescence.

Fluorescence in-situ hybridization. Cornea endothelial cells post oligonucleotide transfection were harvested by typsine and replated on glass slides. Cells were fixed with 4% formaldehyde in 1× phosphate-buffered saline (PBS) and permeabilized in 70% ethanol at 4° C. overnight. After removing the permabilization solution, cells were washed with buffer (10% formamide in 2× saline sodium citrate buffer [SSC]) for 5 min, and then incubated with prehybridization buffer (40% formamide in 2×SSC) at 45° C. for 20 min. $(CAG)_6CA$-5' Texas red-labeled 2-Omethyl RNA 20-mers probe in hybridization buffer (100 mg/mL dextran sulfate and 40% formamide in 2×SSC) was added. The slides were placed in a humidified chamber and incubated in the dark at 37° C. overnight. On the next day, cells were washed twice with wash buffer at 37° C. for 15 min, and then stained with mounting media with DAPI (H-1500; Vector Labs).

Cells were imaged at 60× magnification using a Widefield Deltavision microscope. Images were processed by blind deconvolution with AutoQuant X3. Visualization of RNA foci were made using ImageJ. For quantification, at least 20 pictures were taken from randomly chosen microscopic fields, containing 100-300 cells for each treatment. Counting of foci was performed by different investigators.

FISH of corneal endothelial tissue monolayers were performed using previously described methods (Mootha et al., 2015).

Ex vivo oligonucleotide treatment of human corneas. Post-mortem human donor corneas were obtained from UT Transplant Services (FIG. 11A). The donor corneas were incubated in Optisol GS corneal storage media with a single stranded anti-sense oligonucleotide LC-Cy5 (final concentration 10 µM) at 37° C. The Descemet's membrane-endothelium monolayers were dissected as previously reported[6] either after 1 day or 7 days of treatment, stained with DAPI (Vector Labs), and imaged at 60× magnification using a Widefield Deltavision microscope.

FECD donor corneas with confluent corneal endothelial guttae on specular microscopy and the TCF4 expansion and control donor corneas were bissected and incubated in Optisol GS corneal storage media with control LNA (LC) or LNA1 (final concentration 10 µM) at 37° C. (FIGS. 11B-C). After treatment for 7 days, RNA FISH analysis was performed on the dissected Descemet's membrane-endothelium monolayers from the right eye from each donor to assess $CUG^{exp}$ sense foci as described above. After treatment for 9 days, the total RNA was extracted from the dissected Descemet's membrane-endothelium monolayers using TRIzol (ThermoScientific) per manufacturer's instructions. Alternative splicing of MBNL1 sensitive exons were assessed by RT-PCR as previously described using endothelial tissue from corresponding left eyes of donors (Du et al., 2015).

Statistical Analysis. Correlation between four foci parameters (percentage of total cells with sense foci, number of sense foci per 100 cells, percentage of total cells with antisense foci, and number of antisense foci per 100 cells) and age, sex and CTG repeat number were examined on the 20 FECD subjects by regression linear models.

Example 2—Results

Because the CTG repeat expansion is outside the protein-encoding region of the TCF4 gene, defining the landscape of RNA synthesis is essential for understanding the molecular basis of FECD. The disease-associated expanded CUG repeat occurs within intron 2 of TCF4 pre-mRNA (FIG. 1A) (Breschel et al., 1997). Many genes, including some with expanded repeats, express transcripts that are in an antisense orientation relative to mRNA and these antisense transcripts have the potential to contribute to disease (Gendron et al., 2013; Zu et al., 2013). The inventors used quantitative strand-specific PCR (qPCR) to evaluate antisense transcription in FECD cells at the TCF4 locus and detected an antisense transcript containing the expanded CAG repeat (FIG. 1B, FIGS. 5A-D).

Figure 1C:
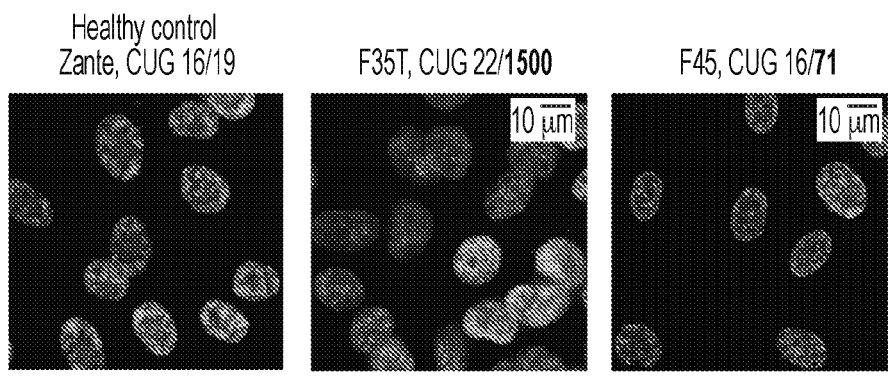
Figure 1D:
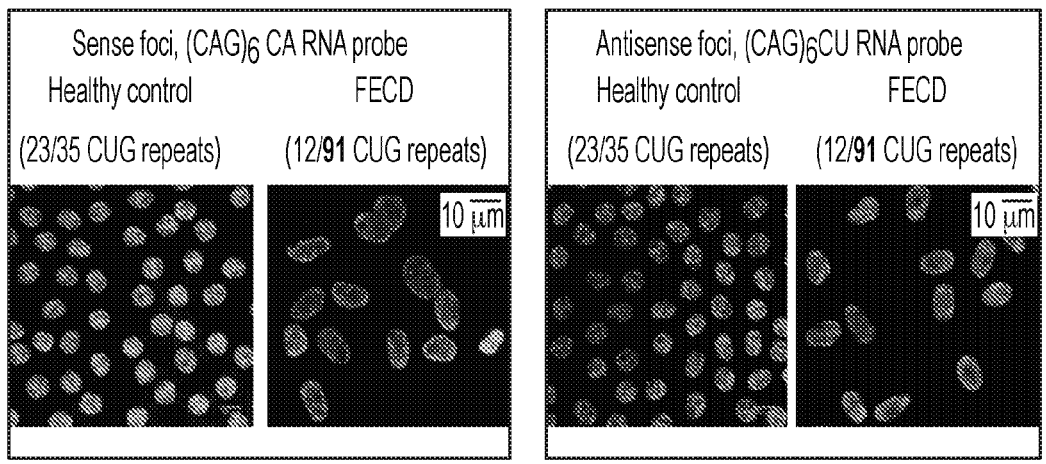

The inventors used FISH to examine the presence of sense or antisense transcript foci within two different corneal endothelial cell lines derived from patients with FECD. For both F35T (1500 CUG repeats) and F45 (71 CUG repeats) cell lines, sense foci were detected (FIG. 1C). No obvious antisense foci were detected. The inventors also used FISH to examine foci in corneal endothelial tissue from a FECD patient with the TCF4 repeat expansion and observed both sense and antisense foci (FIG. 1D). No foci were detected in endothelial cells of control donor cornea endothelial tissue lacking the expansion.

After establishing that both sense and antisense foci were detectable in FECD corneal endothelial tissue, the inventors initiated a quantitative analysis of corneal surgery samples from 20 different FECD patients to assess the impact of RNA expression on disease (FIG. 2A). Tissue samples were used for FISH to evaluate the percentage of endothelial cells with at least one detectable focus and the number of foci per 100 cells.

Both sense and antisense foci were detected in all 20 FECD tissues with the TCF4 triplet repeat expansion (FIG. 2A). Sense foci were found in 62%-95% of cells while the antisense foci found in only 3-27% of the cells. Foci are not numerous, with 1-2.7 sense foci and 0.07-0.6 antisense foci per cell. No foci were observed in a healthy control tissue or a FECD tissue without expansion. Genetic heterogeneity of FECD would account for the lack of foci in endothelial tissue explants from patients without repeat expansions resulting in the same phenotype.

Figure 2B:
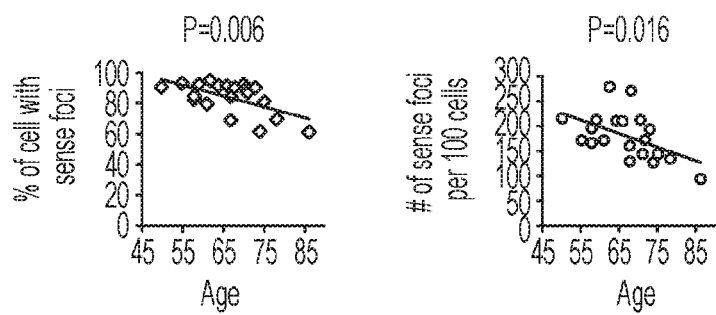
Figure 2C:
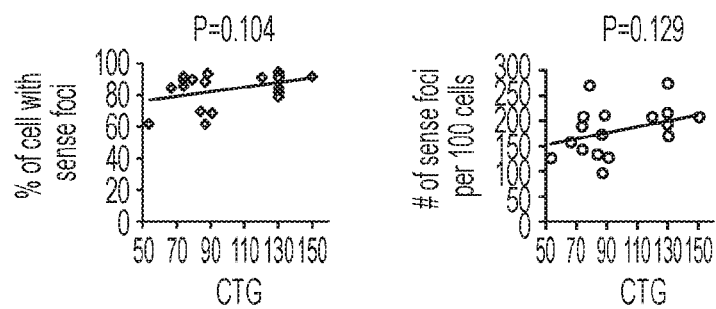
Figure 6A:
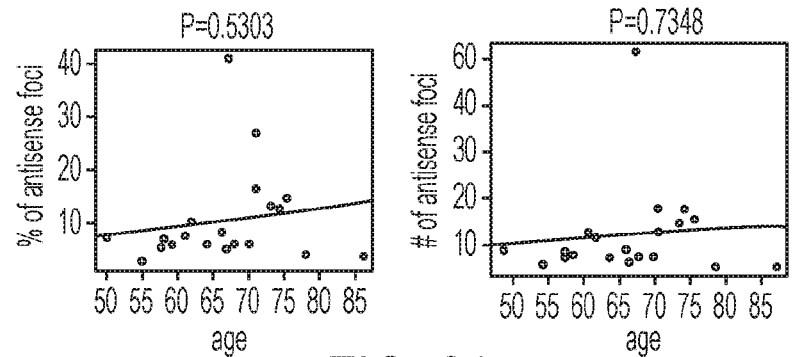
FIGS. 6A-C. Quantitative analysis of sense and antisense foci in FECD patient corneal endothelial tissue samples.
Figure 6B:
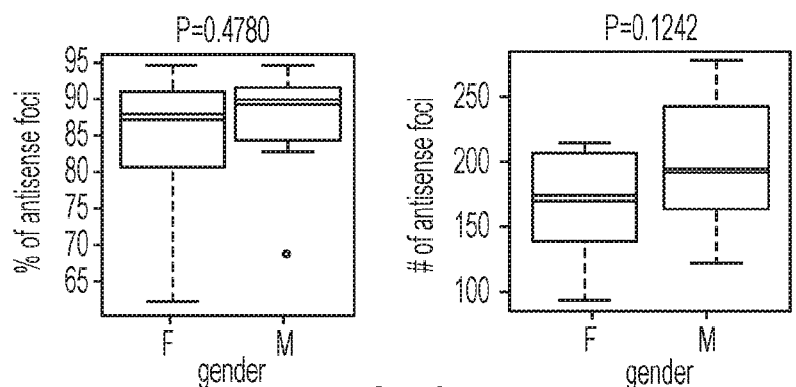
Figure 6C:
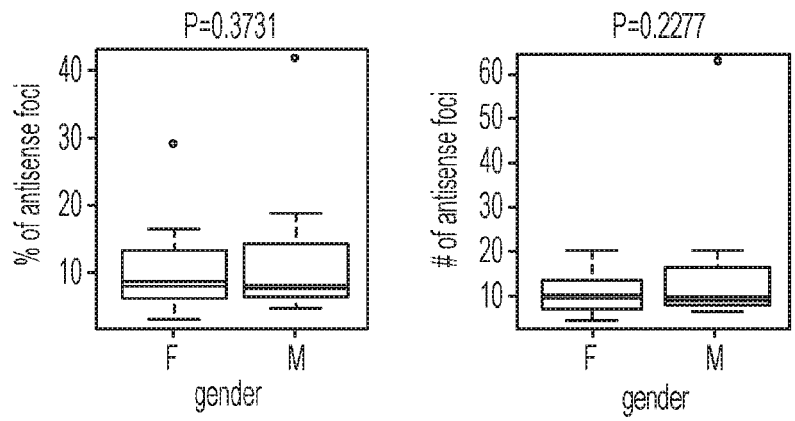

The inventors observed a significant negative correlation between age and both the percentage of cells with sense foci ($P=0.006$) and the number of sense foci per cell ($P=0.016$) (FIG. 2B). Tissues were harvested from patients with late stage disease and the correlation of decreased foci with age may be due to earlier disappearance of cells with relatively large numbers of foci. There was a trend towards a positive correlation between the number of sense foci and the length of the triplet repeat allele, but it did not reach the statistical significance (FIG. 2C). There was no significant correlation between age and foci number for the antisense transcript (FIG. 6A). There was no significant correlation between sex of subjects and foci number. (FIGS. 6B-C).

Figure 2D:
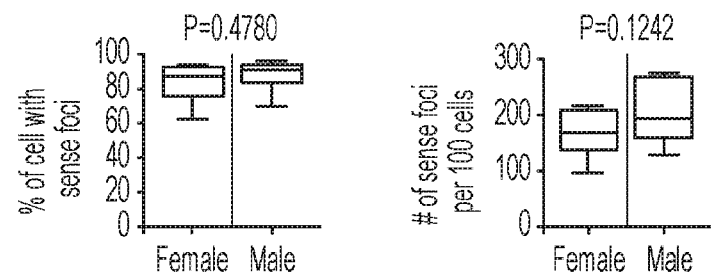
Figure 7:
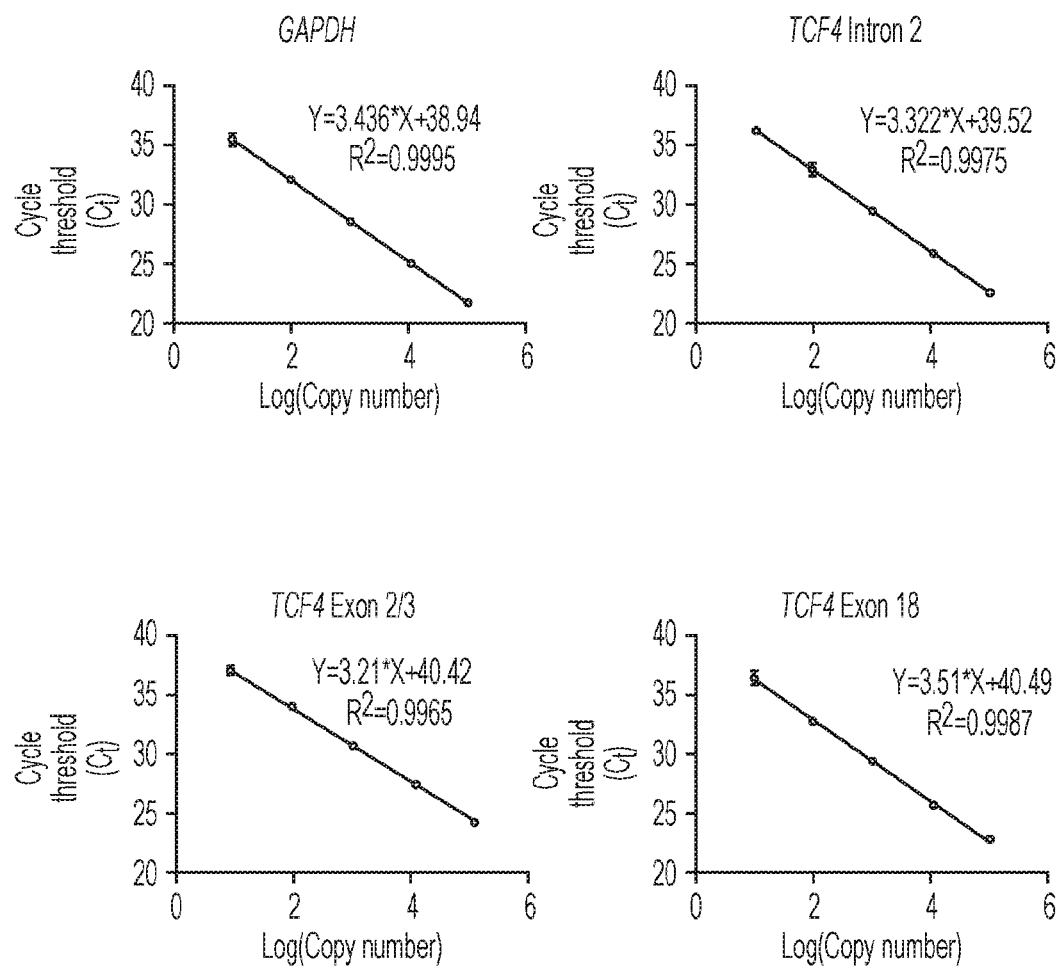
FIG. 7. Standard curve for qPCR efficiency of GAPDH, TCF4 intron 2, TCF4 exon 2/3, TCF4 exon 18. A serial dilution of purified standard RNA, ranging from 10 to 105 copies was used to construct standard curve for qPCR efficiency by qPCR following reverse transcription. Ct value in each dilution were measured in triplicate.

Defining the number of disease-causing molecules is fundamental to understanding of FECD pathology and successful drug development. Using qPCR, the inventors measured a copy number of less than 3 TCF4 intronic transcripts per cell patient tissue samples, control tissue, as well as F35T cells (FIG. 2D; FIGS. 7-8) (Liu et al., 2017). The patient-derived cells used in this study were heterozygous for mutant TCF4 and that these qPCR methods detect both the mutant and wild-type TCF4 intron 2 transcripts, so the number of mutant transcripts is a fraction of the total measured RNA molecules.

Figure 2E:
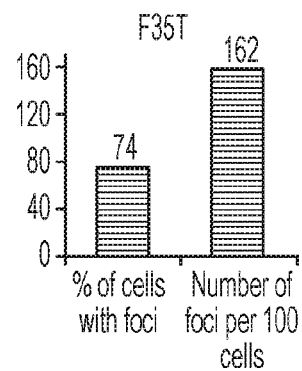
Figure 2F:
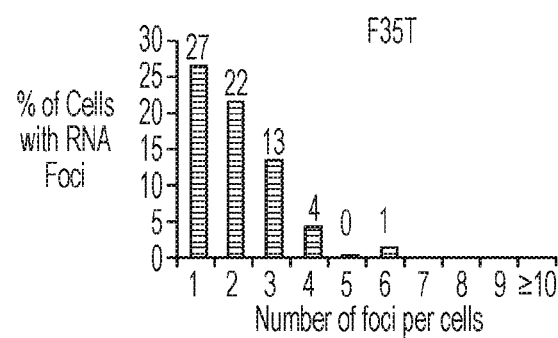
Figure 2G:
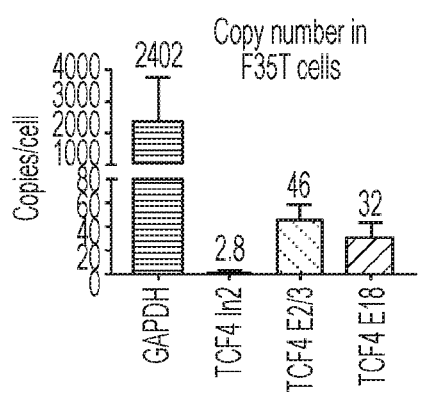
Figure 2H:
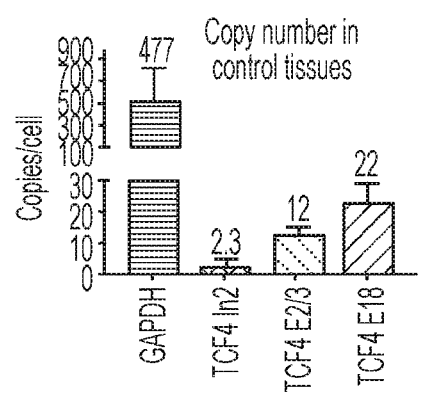
Figure 2I:
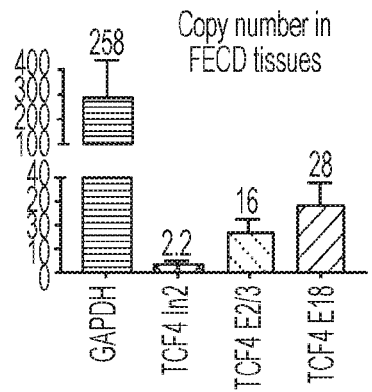

Using FISH, it was determined that most cells have only one or two sense foci (FIGS. 2E-F). Thus, there is an approximately a one-to-one correspondence between mutant intronic RNA transcripts per cell and sense foci per cell, suggesting each focus is a single mutant TCF4 RNA molecule. The inventors' laboratory recently reported that c9orf72 disease-related foci are also each composed of one mutant expanded repeat RNA (Liu et al., 2017). These data cumulatively suggest that small numbers of RNA molecules have a big impact on repeat expansion disease pathogenesis making them ideal therapeutic targets.

Antisense oligonucleotides (ASOs) have several advantages as starting points for FECD drug discovery. ASOs are synthetic nucleic acids that can recognize complementary RNA sequences inside cells and sequence-specifically modulate gene expression in vivo (Khvorova and Watts, 2017). Several ASOs have shown encouraging results in late stage clinical trials, including two recent FDA approvals to alleviate spinal muscular atrophy (Corey, 2017), and muscular dystrophy (Aartsma-Rus and Krieg, 2017).

The inventors chose to test the ability of anti-CUG ASOs to block foci and serve as a starting point for therapeutic development. ASOs targeting the DMPK CUG repeat RNA can reverse cellular phenotypes of myotonic dystrophy (Wojtkowiak-Szlachcic et al., 2015). The inventors and others have shown that synthetic nucleic acids can target expanded CAG repeats within genes causing Huntington's disease, Machado Joseph Disease, and dentatorubral-pallidoluysian atrophy (Hu et al., 2009; Hu et al., 2010; Hu et al., 2014).

FECD sense foci are much more prevalent than antisense foci, making the expanded repeat within the sense transcript the logical target of a molecular therapy. The inventors synthesized locked nucleic acid (LNA) ASOs complementary to the CUG repeat in all three registers relative to the target sequence (FIG. 3A). LNA substitutions were spread through the ASO, creating designs that would not be expected to recruit RNase H to cause degradation of target RNA. LNA is an advantageous chemical modification for drug development because it contains a conformationally restricted ribose that enables high-affinity binding to cellular RNA targets (Braasch and Corey, 2001; Watts, 2013).

Figure 3B:
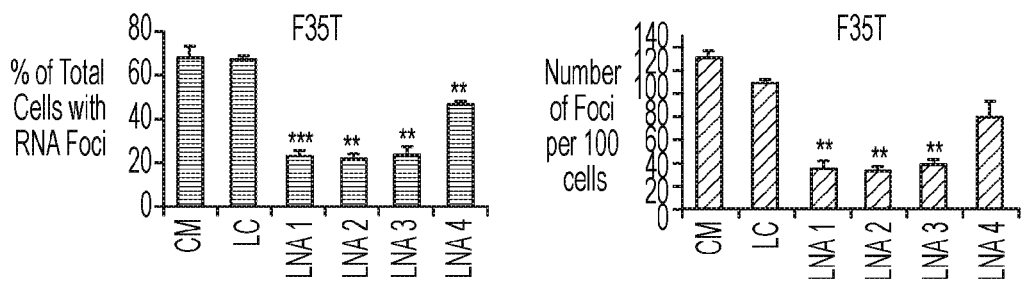
Figure 3C:
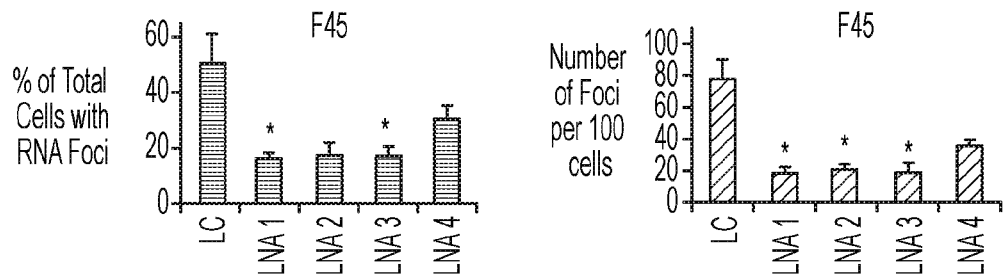
Figure 3D:
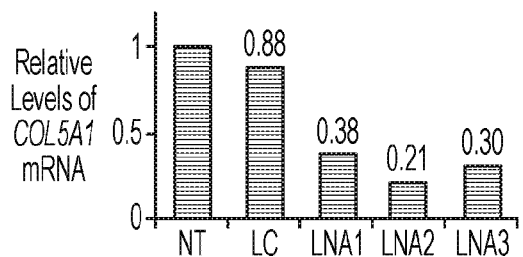
Figure 9:
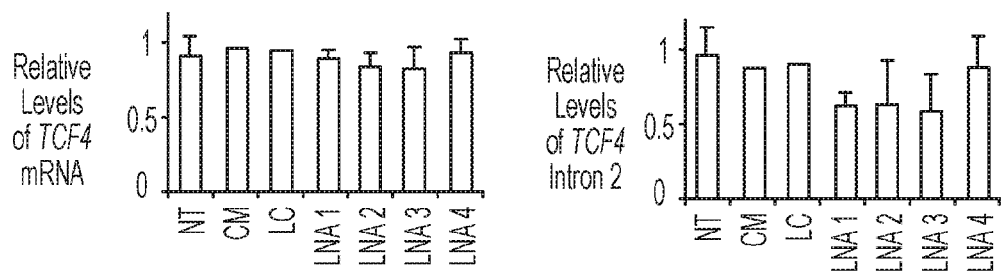
FIG. 9. Effect of LNA-ASOs on TCF4 expression. Quantitative PCR showing that LNAs have little effect on TCF4 mRNA and intron 2 RNA levels.

All three 19-mers (LNA 1-3) were potent inhibitors of CUG foci in F35T or F45 endothelial cell lines (FIGS. 3B-C). The 16-mer LNA 4 is less effective. LNAs 1, 2, and 3 had higher affinities for complementary targets, as measured by melting temperature, than LNA4 (FIGS. 3A-C), probably explaining their greater efficacy. Extracellular matrix proteins are altered in FECD, including an excessive production of Collagen 5A1. All three ASO-LNAs targeting the CUG repeat (LNA1-3) were potent inhibitors of collagen 5A1 (COL5A1) in the FECD corneal endothelial cell line F35T (FIG. 3D). The inventors also tested a 21-mer ASO that was entirely substituted with 2'O-methyl RNA and found that it was less effective (FIG. 8). Transfection of LNAs did not reduce levels of TCF4 RNA (FIG. 9).

Figure 10A:
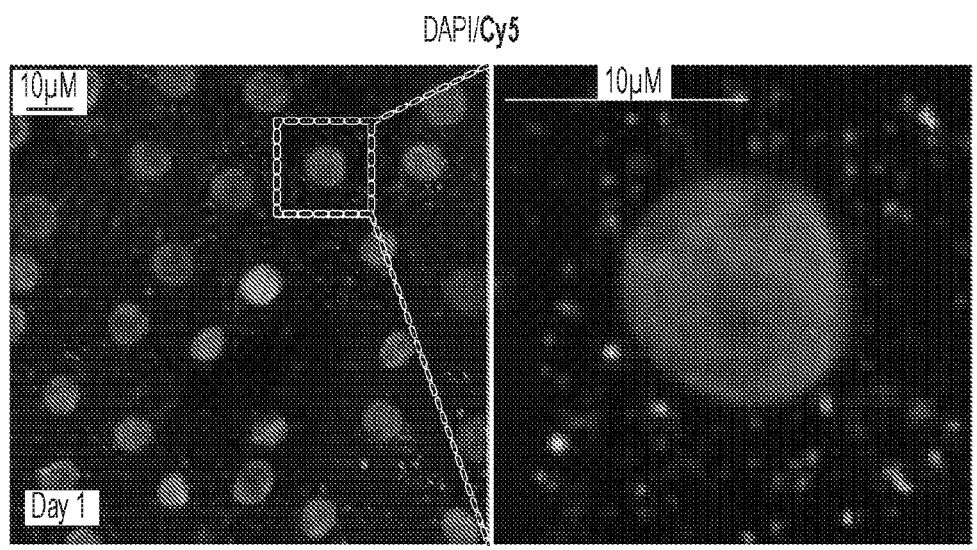
FIGS. 10A-B. Gymnotic delivery of single-strand ASO LC-Cy5 to ex vivo human corneas. Fluorescent images of ex vivo corneal tissue treated with LC-Cy5 (10 μM) for 1 day (FIG. 10A) or 7 day (FIG. 10B). Oligonucleotides were uptake into the cytoplasm and the nucleus of endothelial cells. The nuclei were stained with DAPI. The boxed region were enlarged and shown on the right. The cells were scanned from bottom to the top, about 15 slices of image were taken. Only the middle slices (start from 6 to 10) were used and Z-stacked to generate the pictures.
Figure 10B:
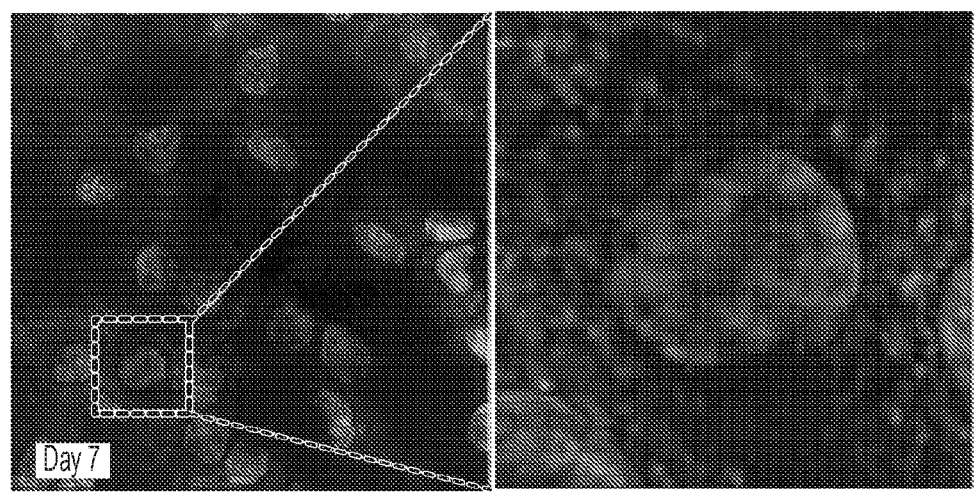

To evaluate whether delivery to corneal tissue was feasible, the inventors first tested "gymnotic" or "naked" (transfection reagent free) uptake of a fluorophore-labeled oligonucleotide into the endothelium of ex vivo human corneas (FIGS. 10A-B) (Stein et al., 2010). Uptake of ASO was observed within both the cytoplasm and nuclei.

Figure 4A:
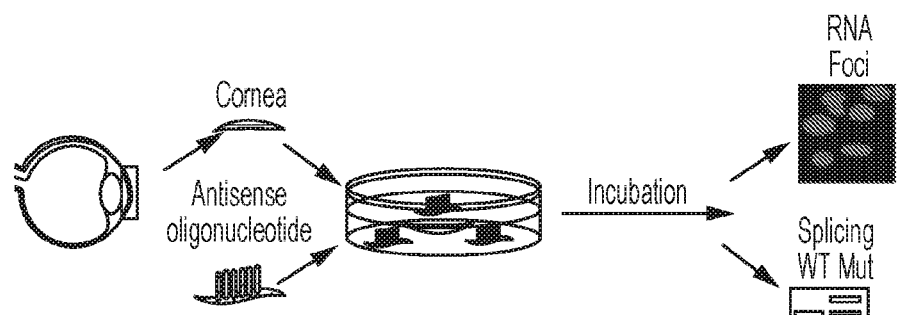
Figure 4B:
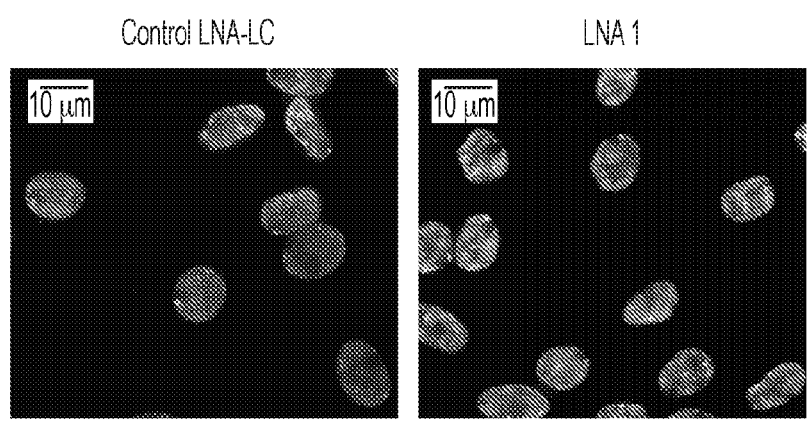
Figure 4C:
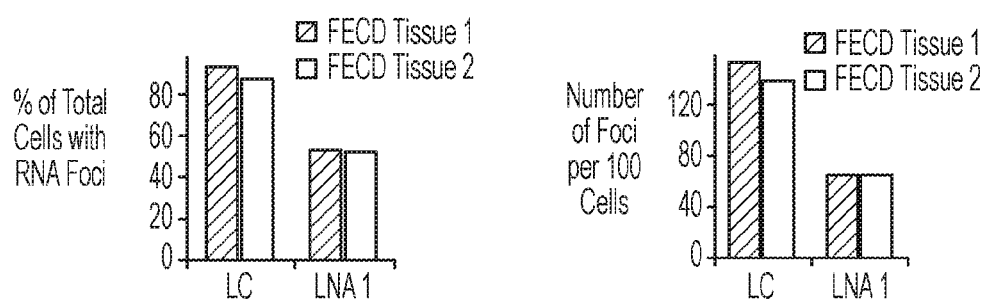

After establishing that ex vivo uptake was possible, the inventors were fortunate to be able to extend their investigation by accessing human corneas deemed unsuitable for transplantation because of findings of FECD and subsequent confirmation of the mutation by genotyping. The inventors treated the corneas of human FECD-patient donors using a non-complementary control (LNA LC) or ASO LNA 1 (FIG. 4A, FIG. 10). After dissection, the Descemet's membrane with endothelium was analyzed by FISH. The inventors found that LNA 1, but not the non-complementary LNA LC, blocked foci formation (FIGS. 4B-C).

The expanded repeat within TCF4 has been shown to affect splicing of MBNL1-sensitive exons in FECD corneal tissue (Du et al., 2015). Binding of the LNAs would block the mutant repeat, preventing the RNA from interacting with MBNL1 or other factors that influence splicing. To determine whether LNA 1 was affecting a cellular phenotype, the inventors examined splicing of INF2, MBNL1, and ADD3, all genes previously identified as being influenced by mutant TCF4. The inventors observed alteration of splicing in all three genes upon administration of LNA 1, partially restoring alternative splicing to that observed in normal corneal tissues (FIGS. 4D-E).

Example 3—Discussion

To the inventors' knowledge, this is the first evidence of correction of a genetic disorder in human corneas. ASOs targeting the mutant TCF4 repeat effectively reduced CUG"P foci formation and pathologic splicing in ex vivo human FECD corneas without transfection reagents. Treatments would likely need to start early in the disease process and continue for an extended period, and will therefore need to be minimally invasive and convenient for patients. Next steps before human clinical trials would be to optimize local delivery protocols. Vitravene, the first ASO drug approved by the FDA, was administered by intraocular (intravitreal) injection for cytomegalovirus retinitis (Geary et al., 2002). Similarly intracameral injection would place an ASO into the anterior chamber of the eye in direct contact with the corneal endothelium. The affected tissue in FECD, however, is only a half-millimeter from the surface of the eye and topical administration by eye drops may be possible. Topical administration of ASO eye drops have already been found to be effective, safe, and well tolerated in phase II FDA trials of aganirsen for keratitis-induced corneal neovascularization Cursiefen et al, 2014). These data provide a rationale of the use of ASOs targeting a handful of mutant TCF4 repeat RNA molecules as a therapeutic strategy to prevent and treat vision loss caused by FECD.

Beyond FECD, the ability to introduce oligonucleotides into corneal tissue suggests the potential to control gene expression associated with many other disorders, such as the group of TGFBI-associated corneal dystrophies and broaden the options for using ASOs in the eye.

Example 4—Materials and Methods

Synthesis and transfection of synthetic nucleic acids. Duplex RNAs were designed and then obtained from IDT (San Jose, Calif.). Double-stranded RNAs were prepared by annealing the two RNA strands in 2.5×PBS solutions. Locked nucleic acid (LNA) phosphoramidites were synthesized from the 3'-hydroxyl precursors (Rasayan) and assembled into ASOs as previously described (Pendergraff et al., 2017). ASOs were deprotected using concentrated aqueous ammonia for 16 h at 55° C. and were characterized by LCMS (FIG. 12A).

Single and double stranded synthetic nucleic acids were transfected into cells with lipid RNAiMAX (Life Technologies) as previously described (Hu et al., 2009). Cells were plated at a density of 300,000 per well of a 6-well plate and transfected at the same time. After 72 hours, the cells were transfected again as mentioned above and harvested 4 days later to assess the effects for reduction of $CUG^{exp}$ foci using RNA FISH/immunofluorescence.

Fluorescence in-situ hybridization. Cornea endothelial cells were harvested by trypsin and replated on glass slides. Cells were fixed with 4% formaldehyde in 1× phosphate-buffered saline (PBS) and permeabilized in 70% ethanol at 4° C. overnight. Cells were washed with wash buffer (10% formamide in 2× saline sodium citrate buffer [SSC]) for 5 min, and then incubated with prehybridization buffer (40% formamide in 2×SSC) at 45° C. for 20 min. $(CAG)_6CA$-5' Texas red-labeled 2-Omethyl RNA 20-mers probe in hybridization buffer (100 mg/mL dextran sulfate and 40% formamide in 2×SSC) was added. The slides were placed in a humidified chamber and incubated in the dark at 37° C. overnight. On the next day, cells were washed twice with wash buffer at 37° C. for 15 min, and then stained with mounting media with DAPI (H-1500; Vector Labs).

Cells were imaged at 60× magnification using a Widefield Deltavision microscope. Images were processed by blind deconvolution with AutoQuant X3. Visualization of RNA foci were made using ImageJ. For quantification, at least 20 pictures were taken from randomly chosen microscopic fields, containing 100-300 cells for each treatment. Counting of foci was performed by different investigators.

Example 5—Results

Efficacy of Synthetic Nucleic Acids to Inhibit Sense Foci in FECD Cell Lines. Antisense oligonucleotides (ASOs) and duplex RNAs (dsRNAs) are synthetic nucleic acids that can recognize complementary RNA sequences inside cells and sequence-specifically modulate gene expression (Khvorova and Watts, 2017). Both ASOs and dsRNAs can function in vivo, providing a basis for the development of drugs to modulate the activities of mutant TCF4 RNA and prevent or treat FECD. Two ASOs were recently approved by the FDA to alleviate spinal muscular atrophy (Corey, 2017), and muscular dystrophy (Aartsma-Rus and Krieg, 2017), and dsRNAs are showing potent and long-lived effects in clinical trials (Ray et al., 2017).

ASOs and dsRNAs recognize RNA by different mechanisms. ASOs bind directly to target RNA without the assistance of clearly defined proteins, while recognition of duplex RNA benefits from the protein machinery of the RNA-induced silencing complex (RISC) (Matsui and Corey, 2017). A CUG repeat within the 3'-untranslated region of the DMPK gene has been shown to cause myotonic dystrophy type 1 (Brook et al., 1992; Mahadevan et al., 1992), and others have previously show ASOs and duplex RNAs targeting this repeat can reverse cellular phenotypes (Wojtkowiak-Szlachcic et al., 2015; and Sobczak et al., 2013). It has been shown that ASOs and duplex RNAs can target expanded CAG repeats within genes causing Huntington disease, Machado Joseph Disease, and Dentatorubral-pallidoluysian atrophy (Hu et al., 2009; Hu et al., 2010; Hu et al., 2014).

The inventors synthesized dsRNAs complementary to the CUG repeat in three different registers (C, A, or G initial base) (FIG. 12A). The dsRNAs were transfected into patient-derived FECD cells using cationic lipid and the effect on $CUG^{exp}$ foci detection was evaluated by FISH after counting approximated one to three hundred cells per experiment. The inventors observed reduced detection of foci in both F35T and F45 patient-derived FECD cell lines (FIGS. 12B-C).

When dsRNAs are fully complementary to their targets, they have the potential to induce cleavage of the target mRNA by argonaute 2 (AGO2) protein (Liu et al., 2004). The potential for this cleavage might increase the likelihood that the dsRNAs might inadvertently affect other genes containing CUG repeats. It is possible to eliminate the potential for RNA-induced cleavage while retaining binding by introducing mismatches relative to target RNA into the center of the dsRNA (FIGS. 1A and 1D) (Wang et al., 2008). The inventors observed that mismatch-containing duplexes were also effective blockers of foci formation, suggesting that the RNAi cleavage function was not necessary for effective inhibition action.

Beside of steric block LNAs, the inventors also designed and synthesized LNA "Gapmers". These ASOs have LNA modifications at 3' and 5' end, clustered around an eight base DNA gap, which capable of recruiting RNase H and cleavage the RNA target (Matsui and Corey, 2017). Gapmers A-G are complementary to TCF4 intron 2 regions upstream or downstream of CUG repeat. Gapmer REP is directly targeted to the CUG repeat. When tested in F35T cell line, all gapmers showed modest reduction of RNA foci (FIGS. 13A-B).

To rigorously test "gymnotic" or "naked" (transfection reagent free) uptake of an oligonucleotide into human corneal endothelium, mature transcripts of Malat1 were tested, as they are known to be retained in the nucleus (Yoshimoto et al., 2016). The efficacy of various LNA-gapmer constructs targeting Malat1 were first screened in F35T corneal endothelial cell line (FIG. 18B). Anti-Malat1 LNA-gapmers (227, 228, 229) were then tested and shown to potently inhibit expression of MALAT1 in ex-vivo human corneas without use of transfection reagents (FIGS. 18C-D).

The tested duplex RNAs and LNA-gapmers targeting the repeat sequence had little impact on expression levels of mature TCF4 mRNA or TCF4 intron 2 suggesting that RNAi cleavage mechanisms are not required for foci reduction (FIGS. 14A-B).

Figure 15:
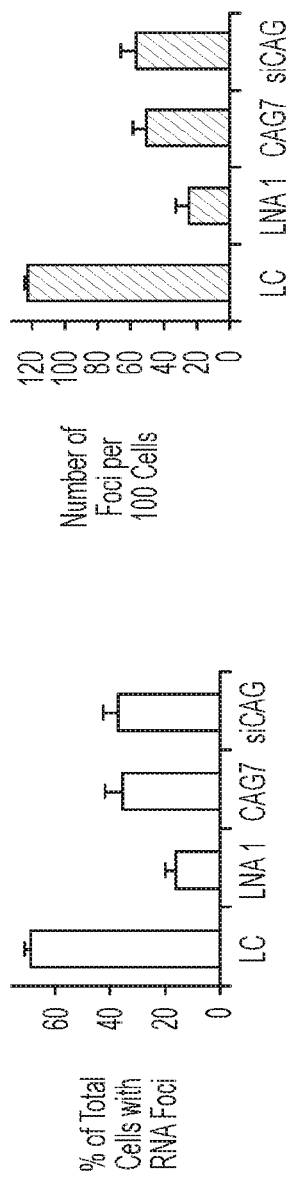
FIG. 15. Comparison of inhibition potency of CUG repeat-targeting oligonucleotides in F35T endothelial cell line. Effect on inhibition of CUG RNA foci by LNA 1, single-strand ASO CAG7 (21-mer 2-OMe modified ASO), and duplex RNA siCAG.

In a comparative study, LNA1 was found to be a more effective inhibitor of foci formation than a dsRNA or a twenty-one base ASO that was entirely substituted with 2'O-methyl targeting the repeat sequence (FIG. 15).

Example 6—Materials and Methods

Figure 16:
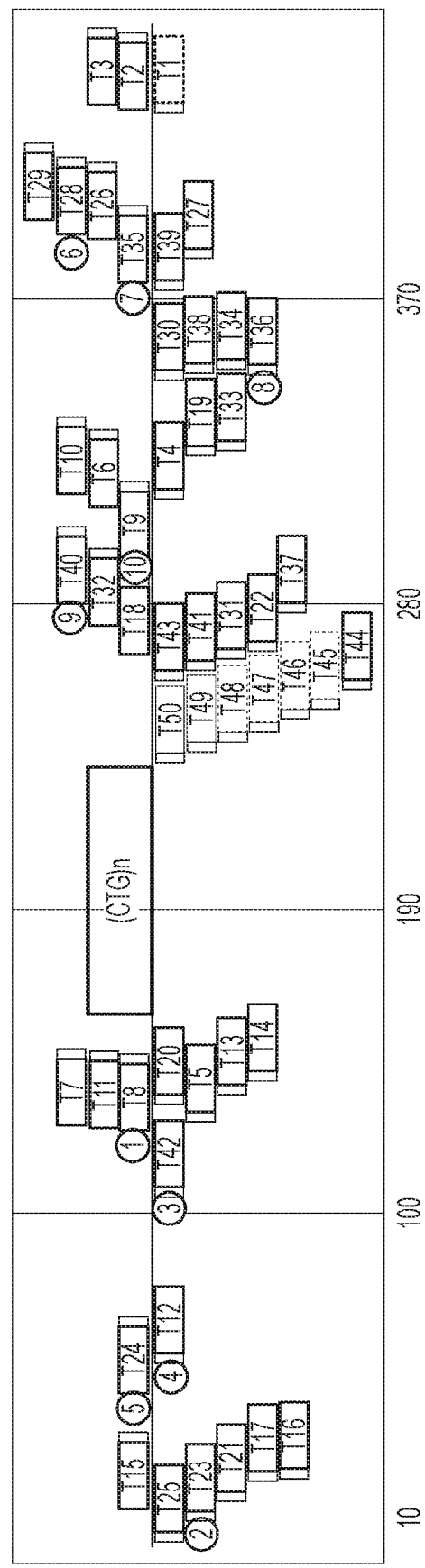
FIG. 16. DNA-targeting CRISPR/Cas9 sgRNA design. Schematic overview of CRISPR/Cas9 target sites across part of the TCF4 intron 2-3 containing the (CTG, CAG)n tract. 50 targets were suggested by the CCTop-CRISPR/Cas9 target online predictor tool. Ten flanking candidate sgRNA targets were selected and marked as ①-⑩.

Dual sgRNA-guided excision of the (CTG,CAG)n DNA tract in TCF4. in silico selection and evaluation of sgRNAs flanking the (CTG,CAG)n tract in the TCF4 gene (FIG. 16) was performed using the CRISPR/Cas9 target online predictor CCTop (Stemmer et al., 2015). The sgRNA constructs were made by ligating sgRNA with pSpCas9(BB)-2A-GFP (px458) using BbsI sites (Addgene). The constructs were validated by Sanger sequencing.

CUG Repeat RNA targeting Cas9 sgRNAs. Six sgRNA constructs targeting the repeat RNA were made by ligating sgRNA with pBluescriptSKII+U6-sgRNA(F+E) empty using BbsI sites (Addgene) (Table 3 and Table 4). CUG1-3 sgRNAs target the expanded CUG repeat RNA (sense foci) and CAG1-3 sgRNAs target the expanded CAG repeat RNA (anti-sense foci). All constructs were validated by Sanger sequencing.

TABLE 3

RNA-targeting CRISPR/Cas9 sgRNA design

| Target | sgRNA spacer sequence | SEQ ID NO: |
|---|---|---|
| CUG1 | GCAGCAGCAGCAGCAGCAGC | SEQ ID NO: 68 |
| CUG2 | GCAGCAGCAGCAGCAGCAGC | SEQ ID NO: 69 |
| CUG3 | CAGCAGCAGCAGCAGCAGCA | SEQ ID NO: 70 |
| CAG1 | CTGCTGCTGCTGCTGCTGCT | SEQ ID NO: 71 |
| CAG2 | TGCTGCTGCTGCTGCTGCTG | SEQ ID NO: 72 |
| CAG3 | GCTGCTGCTGCTGCTGCTGC | SEQ ID NO: 73 |

TABLE 4

Primer sequences for sgRNA cloning and validation.

| Primers | Sequences (5'-3') | Purpose | SEQ ID NO: |
|---|---|---|---|
| CUG1 fwd | CACCGAGCAGCAGCAGCAGCAGCAG | Clone sgRNA into pBlueScriptKSII + U6-sgRNA(F + E) empty | SEQ ID NO: 74 |
| CUG1 rev | AAACCTGCTGCTGCTGCTGCTGCTC | Clone sgRNA into pBlueScriptKSII + U6-sgRNA(F + E) empty | SEQ ID NO: 75 |
| CUG2 fwd | CACCGGCAGCAGCAGCAGCAGCAGC | Clone sgRNA into pBlueScriptKSII + U6-sgRNA(F + E) empty | SEQ ID NO: 76 |
| CUG2 rev | AAACGCTGCTGCTGCTGCTGCTGCC | Clone sgRNA into pBlueScriptKSII + U6-sgRNA(F + E) empty | SEQ ID NO: 77 |
| CUG3 fwd | CACCGCAGCAGCAGCAGCAGCAGCA | Clone sgRNA into pBlueScriptKSII + U6-sgRNA(F + E) empty | SEQ ID NO: 78 |
| CUG3 rev | AAACTGCTGCTGCTGCTGCTGCTGC | Clone sgRNA into pBlueScriptKSII + U6-sgRNA( F+ E) empty | SEQ ID NO: 79 |
| U6 fwd | GAGGGCCTATTTCCCATGATTCC | Send for sequencing to validate the sgRNA construct | SEQ ID NO: 80 |

For RNA-targeting CRISPR/Cas9, pCDNA3.1-dCas9-2xNLS-EGFP (Addgene) and sgRNA constructs were transfected together in a patient-derived FECD corneal endothelial cell line with the TCF4 triplet repeat expansion (F35T cell line, CUG 22/1500) (Generous gift of Albert Jun MD, Johns Hopkins).

For plasmid transfection, reverse transfection was performed in F35T cells in 12-well plate. 500 ng dCas9-GFP plasmid and 500 ng of the appropriate sgRNA plasmid were added to 0.1 mL opti-MEM. Transfection was carried out using Lipofectamine LTX (ThermoFisher Scientific #15338030) according to the manufacturer's instructions. Cells were incubated for 48 hr and then harvested for later experiments.

Expression of plasmids and reduction of RNA foci was assessed by fluorescence microscopy as has previously been described (Hu et al., 2018).

Example 7—Results and Discussion

A recent study has demonstrated the feasibility of the CRISPER/Cas9 technology to excise the CTG triplet repeat expansion in the DMPK gene responsible for myotonic dystrophy type 1 by inducing a pair of double stranded breaks flanking the triplet repeat expansion followed by DNA repair (van Angtmaal et al., 2017). However, simultaneous induction of a pair of breaks flanking the CTG repeat expansion followed by DNA repair in the absence of the repeat was not realized with adequate efficiency in that study.

A nuclear localization signal-tagged nuclease-deficient Cas9-GFP fusion (dCas9-GFP) with appropriate sgRNAs can target and track mRNAs in live cells (Nelles et al., 2016). This RNA-targeting Cas9 system has been modified to efficiently degrade expanded repeat RNA in the repeat expansion disorders of mytonic dystrophy 1, myotonic dystrophy 2, C9orf72-linked amyotrophic lateral sclerosis, and polyglutamine disorders (Batra et al., 2017).

In the study presented herein, synthetic nucleic acids were designed in the form of sgRNAs to perform dual sgRNA-guided excision of the (CTG,CAG)n DNA tract in the TCF4 gene responsible for Fuchs' endothelial corneal dystrophy (FECD) with CRISPR/Cas9 technology. Additionally, the inventors designed, tested, and demonstrate the proficiency of sgRNAs to target and eliminate CUG repeat RNA foci in FECD corneal endothelial cells with the CTG triplet repeat expansions in the TCF4 gene using RNA-targeting Cas9 system.

Dual sgRNA-guided excision of the (CTG,CAG)n DNA tract in TCF4. A summary of 50 candidate sgRNAs flanking the (CTG,CAG)n tract in TCF4 are presented in FIG. 16 and Table 5. The efficacy of each sgRNA was predicted by CRISPRater score. Ten of these sgRNAs (sgRNAs 1-10) were constructed and validated by sequencing.

TABLE 5

List of DNA-targeting CRISPR/Cas9 sgRNAs designed by CCTop
CRISPRater score: LOW efficacy (score <0.56); MEDIUM efficacy
(0.56 <= scpre < 0.74); HIGH efficacy (score >=0.75)

| | Efficacy score by CRISPRater | Genomic Coodinates | Sequence | strand | | SEQ ID NO: |
|---|---|---|---|---|---|---|
| T1 | 0.66 | chr18: 53253170-53253192 | CTCTTCTTCGACGTATCTAGTGG | + | | SEQ ID NO: 81 |
| T2 | 0.48 | chr18: 53253169-53253191 | CACTAGATACGTCGAAGAAGAGG | − | | SEQ ID NO: 82 |
| T3 | 0.59 | chr18: 53253168-53253190 | ACTAGATACGTCGAAGAAGAGGG | − | | SEQ ID NO: 83 |
| T4 | 0.67 | chr18: 53253284-53253306 | CTGCCTAGGGCTACGTTTCCTGG | + | | SEQ ID NO: 84 |
| T5 | 0.56 | chr18: 53253468-53253490 | GCCCCACTTGGAAGGCGGTTTGG | + | | SEQ ID NO: 85 |
| T6 | 0.58 | chr18: 53253287-53253309 | TTGCCAGGAAACGTAGCCCTAGG | − | | SEQ ID NO: 86 |
| T7 | 0.62 | chr18: 53253469-53253491 | TCCAAACCGCCTTCCAAGTGGGG | − | | SEQ ID NO: 87 |
| T8 | 0.74 | chr18: 53253471-53253493 | AATCCAAACCGCCTTCCAAGTGG | − | sgRNA1 | SEQ ID NO: 88 |
| T9 | 0.71 | chr18: 53253302-53253324 | TGGCTTTCGGAAGTTTTGCCAGG | − | sgRNA10 | SEQ ID NO: 89 |
| T10 | 0.64 | chr18: 53253283-53253305 | CAGGAAACGTAGCCCTAGGCAGG | − | | SEQ ID NO: 90 |
| T11 | 0.62 | chr18: 53253470-53253492 | ATCCAAACCGCCTTCCAAGTGGG | − | | SEQ ID NO: 91 |
| T12 | 0.73 | chr18: 53253539-53253561 | CATCTTACACCAAACTCATCTGG | + | sgRNA4 | SEQ ID NO: 92 |
| T13 | 0.57 | chr18: 53253460-53253482 | ATGAAAGAGCCCCACTTGGAAGG | + | | SEQ ID NO: 93 |
| T14 | 0.62 | chr18: 53253456-53253478 | CAGCATGAAAGAGCCCCACTTGG | + | | SEQ ID NO: 94 |
| T15 | 0.65 | chr18: 53253583-53253605 | AACCAAGTCCCAGACATGTCAGG | − | | SEQ ID NO: 95 |

TABLE 5-continued

List of DNA-targeting CRISPR/Cas9 sgRNAs designed by CCTop
CRISPRater score: LOW efficacy (score <0.56); MEDIUM efficacy
(0.56 <= scpre < 0.74); HIGH efficacy (score >=0.75)

| | Efficacy score by CRISPRater | Genomic Coodinates | Sequence | strand | | SEQ ID NO: |
|---|---|---|---|---|---|---|
| T16 | 0.6 | chr18: 53253324-53253346 | AATTCATCTCCTGACATGTCTGG | - | | SEQ ID NO: 96 |
| T17 | 0.65 | chr18: 53253575-53253597 | ATTCATCTCCTGACATGTCTGGG | + | | SEQ ID NO: 97 |
| T18 | 0.62 | chr18: 53253330-53253352 | TCCTCTTCTAGACCTTCTTTTGG | - | | SEQ ID NO: 98 |
| T19 | 0.74 | chr18: 53253271-53253293 | GCTGCAAAGCTGCCTGCCTAGGG | + | | SEQ ID NO: 99 |
| T20 | 0.77 | chr18: 53253463-53253485 | AAAGAGCCCCACTTGGAAGGCGG | + | | SEQ ID NO: 100 |
| T21 | 0.7 | chr18: 53253581-53253603 | CTCCTGACATGTCTGGGACTTGG | + | | SEQ ID NO: 101 |
| T22 | 0.63 | chr18: 53253329-53253351 | TCCAAAAGAAGGTCTAGAAGAGG | + | | SEQ ID NO: 102 |
| T23 | 0.76 | chr18: 53253587-53253609 | ACATGTCTGGGACTTGGTTTAGG | + | sgRNA2 | SEQ ID NO: 103 |
| T24 | 0.69 | chr18: 53253548-53253570 | TTTTTAATGCCAGATGAGTTTGG | | sgRNA5 | SEQ ID NO: 104 |
| T25 | 0.59 | chr18: 53253593-53253615 | CTGGGACTTGGTTTAGGAAAAGG | + | | SEQ ID NO: 105 |
| T26 | 0.72 | chr18: 53253208-53253230 | CTTTTTGCAGGCTCTGACTCAGG | - | | SEQ ID NO: 106 |
| T27 | 0.68 | chr18: 53253214-53253236 | TCAGAGCCTGCAAAAAGCAAAGG | + | | SEQ ID NO: 107 |
| T28 | 0.75 | chr18: 53253207-53253229 | TTTTTGCAGGCTCTGACTCAGGG | - | sgRNA6 | SEQ ID NO: 108 |
| T29 | 0.7 | chr18: 53253203-53253225 | TGCAGGCTCTGACTCAGGGAAGG | - | | SEQ ID NO: 109 |
| T30 | 0.73 | chr18: 53253249-53253271 | AAGTGCAACAAGCAGAAAGGGGG | + | | SEQ ID NO: 110 |
| T31 | 0.57 | chr18: 53253332-53253354 | AAAAGAAGGTCTAGAAGAGGAGG | + | | SEQ ID NO: 111 |
| T32 | 0.46 | chr18: 53253322-53253344 | TAGACCTTCTTTTGGAGAAATGG | - | | SEQ ID NO: 112 |
| T33 | 0.67 | chr18: 53253270-53253292 | GGCTGCAAAGCTGCCTGCCTAGG | + | | SEQ ID NO: 113 |
| T34 | 0.61 | chr18: 53253246-53253268 | AGAAAGTGCAACAAGCAGAAAGG | + | | SEQ ID NO: 114 |
| T35 | 0.75 | chr18: 53253220-53253242 | TTCGTTCCTTTGCTTTTTGCAGG | - | sgRNA7 | SEQ ID NO: 115 |
| T36 | 0.76 | chr18: 53253248-53253270 | AAAGTGCAACAAGCAGAAAGGGG | + | sgRNA8 | SEQ ID NO: 116 |
| T37 | 0.56 | chr18: 53253318-53253340 | AAAGCCATTTCTCCAAAAGAAGG | + | | SEQ ID NO: 117 |
| T38 | 0.62 | chr18: 53253247-53253269 | GAAAGTGCAACAAGCAGAAAGGG | + | | SEQ ID NO: 118 |
| T39 | 0.45 | chr18: 53253223-53253245 | GCAAAAAGCAAAGGAACGAATGG | + | | SEQ ID NO: 119 |

TABLE 5-continued

List of DNA-targeting CRISPR/Cas9 sgRNAs designed by CCTop
CRISPRater score: LOW efficacy (score <0.56); MEDIUM efficacy
(0.56 <= scpre < 0.74); HIGH efficacy (score >=0.75)

| | Efficacy score by CRISPRater | Genomic Coodinates | Sequence | strand | | SEQ ID NO: |
|---|---|---|---|---|---|---|
| T40 | 0.72 | chr18: 53253315-53253337 | TCTTTTGGAGAAATGGCTTTCGG | − | sgRNA9 | SEQ ID NO: 120 |
| T41 | 0.63 | chr18: 53253335-53253357 | AGAAGGTCTAGAAGAGGAGGAGG | + | | SEQ ID NO: 121 |
| T42 | 0.74 | chr18: 53253490-53253512 | GATTTTATTTGTGTGTTTTGTGG | + | sgRNA3 | SEQ ID NO: 122 |
| T43 | 0.49 | chr18: 53253338-53253360 | AGGTCTAGAAGAGGAGGAGGAGG | + | | SEQ ID NO: 123 |
| T44 | 0.62 | chr18: 53253341-53253363 | TCTAGAAGAGGAGGAGGAGGAGG | + | | SEQ ID NO: 124 |
| T45 | 0.62 | chr18: 53253347-53253369 | AGAGGAGGAGGAGGAGGAGAAGG | + | | SEQ ID NO: 125 |
| T46 | 0.69 | chr18: 53253350-53253372 | GGAGGAGGAGGAGGAGAAGGAGG | + | | SEQ ID NO: 126 |
| T47 | 0.76 | chr18: 53253353-53253375 | GGAGGAGGAGGAGAAGGAGGAGG | + | | SEQ ID NO: 127 |
| T48 | 0.68 | chr18: 53253356-53253378 | GGAGGAGGAGAAGGAGGAGGAGG | + | | SEQ ID NO: 128 |
| T49 | 0.68 | chr18: 53253359-53253381 | GGAGGAGAAGGAGGAGGAGGAGG | + | | SEQ ID NO: 129 |
| T50 | 0.61 | chr18: 53253362-53253384 | GGAGAAGGAGGAGGAGGAGGAGG | + | | SEQ ID NO: 130 |

T45-T50 have offtarget sites with MM = 0

Figure 17A:
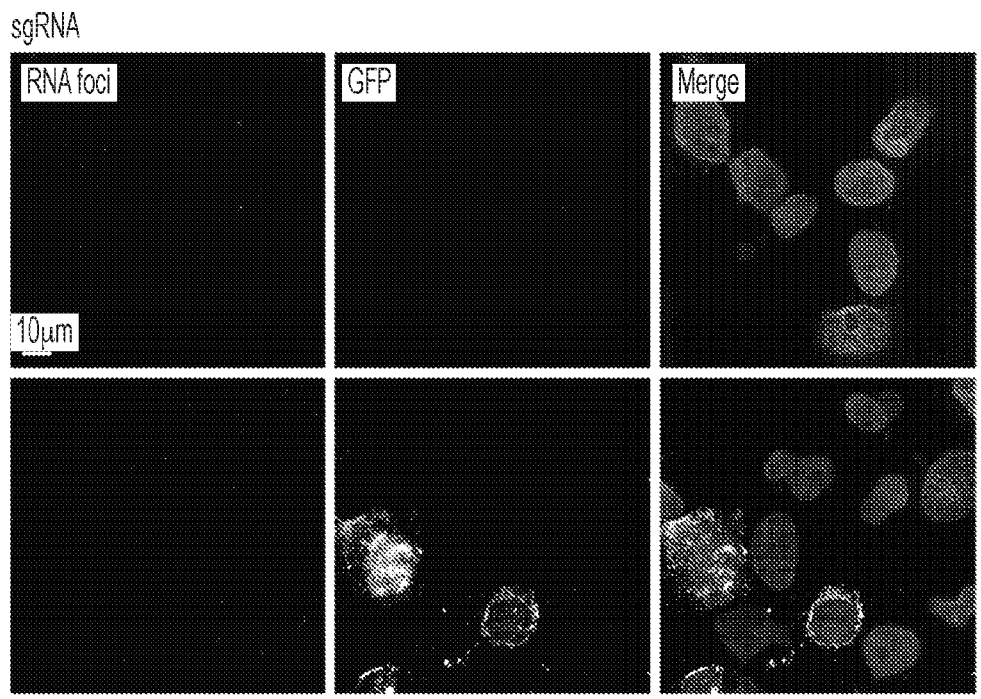
FIGS. 17A-D. RNA-targeting CRSPR/Cas9 in FECD corneal endothelial cell line (F35T, CUG 22/1500).
Figure 17B:
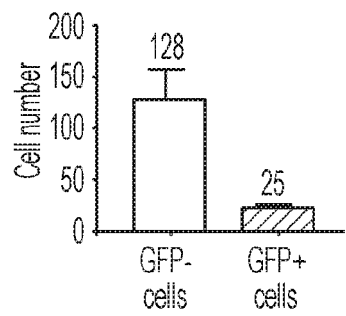

CUG repeat RNA targeting Cas9 sgRNAs. With the described transfection protocol, 16.3% of the F35T cells were transfected with the dCas9-GFP (FIGS. 17A and 17B) as assessed by fluorescence microscopy.

Figure 17C:
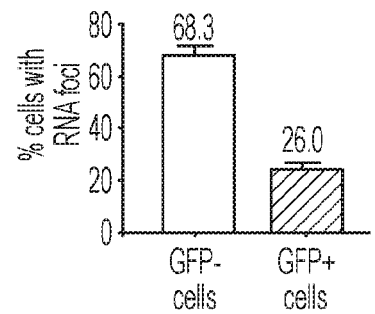
Figure 17D:
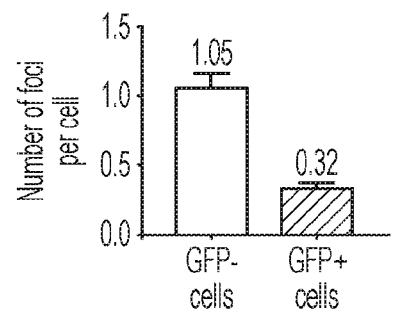

When F35T were co-transfected with both dCas9-GFP and the CUG1 sgRNA, 68.3% of the GFP negative cells had one or more CUG repeat RNA sense foci compared to 26.0% of GFP positive cells (FIG. 17C). There was also a decrease in the number of foci per cell in the GFP positive cells (FIG. 17D).

In silico evaluation of the (CTG,CAG)n tract in TCF4 reveals numerous flanking sgRNAs which can each be tested individually for cutting efficiency using the T7 endonuclease assay (van Agtmaal et al., 2017). The best pairs of flanking sgRNAs can then be tested to determine efficiency of dual sgRNA-guided excision of the (CTG,CAG)n tract in the TCF4 gene in corneal endothelial cell lines and in human corneal endothelial tissue.

Recent studies on myotonic dystrophy type 1 suggest that elimination of toxic microsatellite repeat expansion RNA by RNA-targeting Cas9 may be a more efficient approach than excising the microsatellite repeat expansion DNA using the CRISPR-Cas9 technology (Batra et al., 2017). Therefore, this study sought to validate sgRNAs that target the toxic CUG repeat RNA in FECD.

This is the first proof of concept that a CUG repeat targeting sgRNA (CUG1) can be used to eliminate toxic RNA foci in patient-derived FECD corneal endothelial cells using a RNA-targeting dCas9 targeting system. sgRNA constructs CUG2 and CUG3 are also promising constructs to test since they also target the CUG repeat RNA in different registers (Tables 3 and 4).

It has been reported that the CUG repeat sense RNA foci predominate over the CAG repeat anti-sense foci in FECD corneal endothelial tissue samples of subjects with the TCF4 repeat expansion (Hu et al., 2018). However, it is hypothesized that sgRNA constructs CAG1-3 can be used to target the less common CAG repeat antisense foci in FECD as adjuvant molecular therapies. Further optimization of the transfection efficiency of the CUG repeat RNA Cas9 targeting system may make this an ideal therapeutic approach to prevent or treat FECD.

Example 8—Conclusion

The inventors found both duplex RNAs and LNA gapmer ASOs to be effective inhibitors of RNA foci. Further, it was found that the CRISPR/Cas9 system could used with two sgRNA guides to inhibit focus formation. Thus, single- and double-stranded synthetic nucleic acids targeting the TCF4 triplet repeat expansion are promising therapeutic strategies to prevent and treat FECD, as well as guide CRISPR-Cas9 mediated excision of the TCF4 triplet repeat expansion or CUG repeat RNA targeting Cas9 sgRNAs.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

XI. REFERENCES

The following references, to the extent that they provide exemplary procedural or other details supplementary to those set forth herein, are specifically incorporated herein by reference.

Aartsma-Rus & Krieg, *Nucleic Acid Ther.*, 27: 1-3, 2017.
Aiba et al., *Biochemistry* 52, 9329-9338, 2013.
Amiel et al., *American Journal of Human Genetics*, 80:988-993, 2007.
Cursiefen et al., *Ophthalmology*, 121: 1683-1692, 2014.
Batra et al., *Cell*, 170: 899-912 e810, 2017.
Braasch & Corey, *Chem Biol.*, 8: 1-7, 2001.
Breschel et al., *Human molecular genetics* 6:1855-1863, 1997.
Brockschmidt et al., *Human Molecular Genetics*, 16:1488-1494, 2007.
Brook et al., *Cell*, 68: 799-808, 1992.
Chang et al., *Stem Cells.*, 27:1042-1049, 2009.
Chi et al., *American Journal of Ophthalmology*, 45:518-535, 1958.
Corey, *Nat Neurosci*, 20: 497-499, 2017.
Donnelly et al., *J. Gen. Virol.* 82, 1027-1041, 2001.
Du et al., *The Journal of Biological Chemistry*, 290(10): 5979-90, 2015.
Dupouy et al., *Angew. Chem. Int. Ed.*, 46: 3623-3627, 2006.
EP 266 032
Evers et al., *Plos One* 6, E24308, 2011.
Eye Banking Statistical Report Washington, D.C.: Eye Bank Association of America; 2013.
Fiszer et al., *Nucleic Acids Res.* 39, 5578-5585, 2011.
Gagnon, et al., *Biochemistry* 49, 10166-10178, 2010.
Gagnon et al., *J. Am. Chem. Soc.* 133, 8484-8407, 2011.
Geary et al., *Clin Pharmacokinet.*, 41: 255-260, 2002.
Gendron et al., *Acta Neuropathol.*, 126: 829-844, 2013.
Hogan et al., *American Journal of Ophthalmology*, 78:363-383, 1974.
Hu et al., *Biochemistry* 53, 4510-4518, 2014.
Hu et al., *Chem. Biol.* 17, 1183-1188, 2010.
Hu et al., *Chem. Biol.* 22: 1505-1511, 2015.
Hu et al., *Human Molecular Genetics*, 2018.
Hu et al., *Nat. Biotechnol.* 27, 478-484, 2009.
Hu et al., *Nucleic Acid Therapeutics* 24, 199-209, 2014.
Hu et al., *Nucleic Acids Res.* 40, 11270-11280, 2012.
Juliano et al., *Nucleic Acids Res.* 44:6518-6548, 2016.
Khvorova & Watts, *Nature biotechnology*, 35: 238-248, 2017.
Krachmer et al., *Archives of Ophthalmology*, 96:2036-2039, 1978.
Laing et al., *Archives of Ophthalmology*, 99:80-83, 1981.
Lima et al., *Cell* 150, 883-894, 2012.
Liu et al., *Cell Chem Biol.*, 24: 141-148, 2017.
Liu et al., *Nucleic Acids Res.* 41, 9570-9583, 2013.
Liu et al., *Nucleic Acids Res.* 41, 8788-8801, 2013.
Liu et al., *Nucl. Acid Therapeutics* 25: 113-120, 2015.
Liu et al., *Science* 305, 1437-1441, 2004.
Lorenzetti et al., *American Journal of Ophthalmology*, 64:1155-1158, 1967.
Mahadevan et al., *Science*, 255: 1253-1255, 1992.
Matsui & Corey, *Nat. Rev. Drug Discov.*, 16: 167-179, 2017.
Mootha et al., *Investigative Ophthalmology & Visual Science*, 55:33-42, 2014.
Mootha et al., *Investigative Ophthalmology & Visual Science*, 56(3):2003-11, 2015.
Mootha et al., *Investigative Ophthalmology & Visual Science*, 58: 4579-4585, 2017.
Nishina et al., *Nature Communications*, 6:7969, 2015.
PCT International Applications Nos. PCT/US2008/066154.
PCT International Applications Nos. PCT/US2008/068922.
PCT International Applications Nos. PCT/US2008/064591.
Pendergraff et al., *Molecular Therapy—Nucleic Acids*, 8: 158-168, 2017.
Ray et al., *The New England Journal of Medicine*, 376: 1430-1440, 2017.
Sepp et al., *Human Molecular Genetics*, 21:2873-2888, 2012.
Sheerin et al., *Aging Cell*, 11: 234-240, 2012.
Sobczak et al., *Molecular Therapy: The Journal of the American Society of Gene Therapy.* 21(2):380-387, 2013.
Soliman et al., *JAMA Ophthalmol.*, 133(12):1386-91, 2015.
Steffens and Leurmann, *J. am. Chem. Soc.*, 119: 11548-11549, 1997.
Stein et al., *Nucleic acids research*, 38: e3, 2010.
Stemmer et al., *PloS one*, 10: e0124633, 2015.
Szoka and Papahadjopoulos, *Proc Natl Acad Sci USA*, September; 75(9):4194-8, 1978.
Toyono et al., *Cornea*, 35: 1466-1470, 2016.
U.S. Pat. No. 3,687,808
U.S. Pat. No. 4,587,044
U.S. Pat. No. 4,605,735
U.S. Pat. No. 4,667,025
U.S. Pat. No. 4,762,779
U.S. Pat. No. 4,789,737
U.S. Pat. No. 4,824,941
U.S. Pat. No. 4,828,979
U.S. Pat. No. 4,835,263
U.S. Pat. No. 4,845,205
U.S. Pat. No. 4,876,335
U.S. Pat. No. 4,904,582
U.S. Pat. No. 4,948,882
U.S. Pat. No. 4,958,013
U.S. Pat. No. 5,082,830
U.S. Pat. No. 5,082,830
U.S. Pat. No. 5,109,124
U.S. Pat. No. 5,112,963
U.S. Pat. No. 5,112,963
U.S. Pat. No. 5,118,802
U.S. Pat. No. 5,130,302
U.S. Pat. No. 5,134,066
U.S. Pat. No. 5,138,045
U.S. Pat. No. 5,175,273
U.S. Pat. No. 5,214,136
U.S. Pat. No. 5,214,136
U.S. Pat. No. 5,218,105
U.S. Pat. No. 5,245,022
U.S. Pat. No. 5,254,469
U.S. Pat. No. 5,258,506
U.S. Pat. No. 5,262,536
U.S. Pat. No. 5,272,250
U.S. Pat. No. 5,292,873
U.S. Pat. No. 5,317,098
U.S. Pat. No. 5,367,066

U.S. Pat. No. 5,371,241
U.S. Pat. No. 5,391,723
U.S. Pat. No. 5,414,077
U.S. Pat. No. 5,416,203
U.S. Pat. No. 5,432,272
U.S. Pat. No. 5,451,463
U.S. Pat. No. 5,457,187
U.S. Pat. No. 5,459,255
U.S. Pat. No. 5,484,908
U.S. Pat. No. 5,486,603
U.S. Pat. No. 5,502,177
U.S. Pat. No. 5,510,475
U.S. Pat. No. 5,512,439
U.S. Pat. No. 5,512,667
U.S. Pat. No. 5,514,785
U.S. Pat. No. 5,525,465
U.S. Pat. No. 5,525,711
U.S. Pat. No. 5,541,313
U.S. Pat. No. 5,545,730
U.S. Pat. No. 5,552,538
U.S. Pat. No. 5,552,540
U.S. Pat. No. 5,565,552
U.S. Pat. No. 5,567,810
U.S. Pat. No. 5,574,142
U.S. Pat. No. 5,578,717
U.S. Pat. No. 5,578,718
U.S. Pat. No. 5,580,731
U.S. Pat. No. 5,580,731
U.S. Pat. No. 5,585,481
U.S. Pat. No. 5,587,371
U.S. Pat. No. 5,587,469
U.S. Pat. No. 5,591,584
U.S. Pat. No. 5,594,121
U.S. Pat. No. 5,595,726
U.S. Pat. No. 5,596,091
U.S. Pat. No. 5,597,696
U.S. Pat. No. 5,599,923
U.S. Pat. No. 5,599,928
U.S. Pat. No. 5,608,046
U.S. Pat. No. 5,614,617
U.S. Pat. No. 5,645,985
U.S. Pat. No. 5,681,941
U.S. Pat. No. 5,688,941
U.S. Pat. No. 5,750,692
U.S. Pat. No. 5,763,588
U.S. Pat. No. 5,830,653
U.S. Pat. No. 6,005,096
U.S. Pat. No. 6,268,490
U.S. Pat. No. 6,525,191
U.S. Pat. No. 6,670,461
U.S. Pat. No. 6,770,748
U.S. Pat. No. 6,794,499
U.S. Pat. No. 7,034,133
U.S. Pat. No. 7,053,207
U.S. Pat. No. 7,399,845
U.S. Pat. No. 5,795,715
U.S. Pat. No. 6,506,559
U.S. Pat. No. 6,573,099
U.S. Pat. No. 5,795,715

U.S. Pat. No. 4,659,774
U.S. Pat. No. 4,816,571
U.S. Pat. No. 5,141,813
U.S. Pat. No. 5,264,566
U.S. Pat. No. 4,959,463
U.S. Pat. No. 5,428,148
U.S. Pat. No. 5,554,744
U.S. Pat. No. 5,574,146
U.S. Pat. No. 5,602,244
U.S. Pat. No. 5,705,629
U.S. Pat. No. 4,683,202
U.S. Pat. No. 4,682,195
U.S. Pat. No. 5,645,897
U.S. Patent Publication No. US2005/0130923
U.S. Patent Publication No. US2007/0287831
U.S. Patent Publication No. US2008/0039618
U.S. Patent Publication No. US2004/0171570
U.S. Patent Publication No. US2003/0051263
U.S. Patent Publication No. US2003/0055020
U.S. Patent Publication No. US2004/0265839
U.S. Patent Publication No. US2002/0168707
U.S. Patent Publication No. US2003/0159161
U.S. Patent Publication No. US2004/0064842
U.S. Ser. No. 12/129,154
U.S. Ser. No. 60/989,574
U.S. Ser. No. 61/026,995
U.S. Ser. No. 61/026,998
U.S. Ser. No. 61/056,564
U.S. Ser. No. 61/086,231
U.S. Ser. No. 61/097,787
U.S. Ser. No. 61/099,844
van Agtmaal et al., Molecular therapy: the journal of the American Society of Gene Therapy, 25:24-43, 2017.
Wang et al., Nature, 456: 921-926, 2008.
Watts, J. K., Chem Commun (Camb), 49: 5618-5620, 2013.
Wieben et al., Investigative Ophthalmology & Visual Science, 55:6101-6107, 2014.
Wieben et al., PloS One, 7:e49083, 2012.
Winkler et al., Therapeutic delivery, 4:791-809, 2013.
WO 1994/14226
WO 2004/106356
WO 2005/021570
WO 2007/134181
WO 99/32619
WO 01/68836
WO 00/44914
WO 01/36646
Wojciechowska and Krzyzosiak, Human Molecular Genetics, 20:3811-3821, 2011.
Wojtkowiak-Szlachcic et al., Nucleic Acids Research 43(6): 3318-31, 2015.
Xing et al., Investigative Ophthalmology & Visual Science 55(11):7073-7078, 2014.
Yoshimoto et al., Biochimica et biophysica acta, 1859: 192-199, 2016.
Yu et al., Cell 150, 895-908, 2012.
Zu et al., Proceedings of the National Academy of Sciences of the United States of America, 110: E4968-4977, 2013.
Zweier et al., American Journal of Human Genetics, 80:994-1001, 2007.

What is claimed:

1. A method of reducing expanded CUG repeat RNA nuclear foci in a corneal endothelial cell comprising contacting a corneal endothelial cell having an expanded CUG repeat region with a double-stranded (ds) ribonucleic acid (RNA) of 13 to 120 nucleotides in length and having a repeating tri-nucleobase sequence comprising CAG or targeting intron 2 of TCF4.

2. A method of treating a subject with Fuchs endothelial corneal dystrophy, comprising administering at least one double-stranded ds ribonucleic acid RNA of 13 to 120 nucleotides in length and having a repeating tri-nucleobase sequence comprising CAG or targeting intron 2 of TCF4 to the subject.

3. The method of claim 1, wherein said dsRNA comprises one or more chemically-modified nucleobases.

4. The method of claim 3, wherein said one or more chemically-modified nucleobases is a nuclease-resistant modification.

5. The method of claim 4, wherein said nuclease-resistant modification is a modified sugar moiety or a modified internucleoside linkage.

6. The method of claim 4, wherein said nuclease-resistant modification is a modified sugar moiety and wherein said modified sugar moiety is a high-affinity sugar modification; or wherein the modified sugar moiety is a tricyclic moiety, a morpholino moiety, or a 4' to 2' bicyclic sugar moiety.

7. The method of claim 6, wherein each 4' to 2' bridge is independently —[C(R$_c$)(R$_d$)]$_n$—, —[C(R$_c$)(R$_d$)]$_n$—O—, —C(R$_c$R$_d$)—N(R$_e$)—O— or —C(R$_e$R$_d$)—O—N(R$_e$)—, wherein each R$_e$ and Rd is independently hydrogen, halogen, substituted or unsubstituted C$_1$-C$_6$ alkyl; and each R$_e$ is independently hydrogen or substituted or unsubstituted C$_1$-C$_6$ alkyl.

8. The method of claim 1, wherein said dsRNA:
i) comprises a central mismatch (within bases 9-14) with a target sequence comprising said repeating tri-nucleobase sequence;
ii) comprises at least one ligand or lipid group, and/or
iii) targets repeat CUG RNA or intron 2 of TCF4 with CTG18.1 triplet repeat polymorphism and comprises the sequence of any of SEQ ID NOS: 1-4, and 42-50.

9. The method of claim 1, wherein the double-stranded RNA molecule is selected from the group consisting of SEQ ID NOS: 1/3, 2/42, 2/4, 43/44, 45/46, 47/48 and 49/50.

10. The method of claim 9, wherein the dsRNA is a siRNA or a shRNA, and/or comprises at least one modified nucleotide.

11. The method of claim 8, wherein the dsRNA is a siRNA and wherein the siRNA comprises one strand of 14-19 nucleotides in length and a second strand of 19-22 nucleotides in length, or wherein the siRNA comprises at least one modified nucleotide.

12. The method of claim 11, wherein the at least one modification is selected from the group consisting of 2'-O-methyl-ribonucleotides, 2'-fluoro-ribonucleotides, 5'-vinylphosphonate, phosphorothioate linkage, or lipid conjugation.

13. The method of claim 1, wherein the cell is located in a subject suffering from Fuchs' endothelial corneal dystrophy.

14. The method of claim 1, wherein contacting comprises administering said dsRNA by direct administration into the eye.

15. The method of claim 14, where wherein direct administration to the eye is in an eye drop, by intracameral injection, or by intravitreal injection.

16. The method of claim 14, wherein the eye drop comprises a saline or buffered saline solution.

17. The method of claim 10, wherein the at least one modification is selected from the group consisting of 2'-O-methyl-ribonucleotides, 2'-fluoro-ribonucleotides, 5'-vinylphosphonate, phosphorothioate linkage, or lipid conjugation.

18. The method of claim 6, wherein said high-affinity sugar modification is a bicyclic sugar moiety or a 2'-modified sugar moiety.

19. The method of claim 6, wherein said morpholino moiety is a phosphorodiamidate morpholino moiety.

20. The method of claim 6, wherein said 4' to 2' bicyclic sugar moiety is a 4'-CH$_2$—O-2' or 4'-CH(CH$_3$)—O-2' bicyclic sugar moiety.

21. The method of claim 6, wherein each 4' to 2' bridge independently comprises from 2 to 4 linked groups independently selected from 13 [C(R$_a$)(R$_b$)]$_y$, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_1$)—; wherein x is 0, 1, or 2; y is 1, 2, 3, or 4; each R$_a$ and R$_b$ is, independently, H, a protecting group, hydroxyl, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_9$ aryl, substituted C$_5$-C$_{20}$ aryl, heterocycle radical, substituted heterocycle radical, heteroaryl, substituted heteroaryl, C$_5$-C$_7$ alicyclic radical, substituted C$_{5=\ alicyclic\ radical,\ halogen,\ OJ_1}$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_{20}$ aryl, substituted C$_5$-C$_9$ aryl, acyl (C(=O)—H), substituted acyl, a heterocycle radical, a substituted heterocycle radical, C$_1$-C$_6$ aminoalkyl, substituted C$_1$-C$_6$ aminoalkyl or a protecting group.

22. The method of claim 7, wherein each 4' to 2' bridge is independently a 4'-(CH$_2$)$_2$-2',4'-(CH$_2$)$_3$-2',4'-CH$_2$—O-2',4'-CH(CH$_3$)—O-2',4'—(CH$_2$)$_2$-0-2',4'—CH$_2$—O—N(R$_e$)-2' and 4'-CH$_2$—N(Re)-O-2'-bridge.

* * * * *

UNITED STATES PATENT AND TRADEMARK OFFICE
CERTIFICATE OF CORRECTION

| | | |
|---|---|---|
| PATENT NO. | : 11,512,312 B2 | Page 1 of 1 |
| APPLICATION NO. | : 16/492522 | |
| DATED | : November 29, 2022 | |
| INVENTOR(S) | : Mootha et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 143 days.

Signed and Sealed this
Fourteenth Day of January, 2025

Derrick Brent
*Acting Director of the United States Patent and Trademark Office*